United States Patent
Hekimi et al.

(10) Patent No.: US 12,053,441 B2
(45) Date of Patent: Aug. 6, 2024

(54) FORMULATIONS FOR IMPROVING THE DELIVERY OF HYDROPHOBIC AGENTS

(71) Applicant: THE ROYAL INSTITUTION FOR THE ADVANCEMENT OF LEARNING / MCGILL UNIVERSITY, Montreal (CA)

(72) Inventors: Siegfried Hekimi, Montreal (CA); Ying Wang, Montreal (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 237 days.

(21) Appl. No.: 16/966,212

(22) PCT Filed: Jan. 31, 2019

(86) PCT No.: PCT/CA2019/050120
§ 371 (c)(1),
(2) Date: Jul. 30, 2020

(87) PCT Pub. No.: WO2019/148282
PCT Pub. Date: Aug. 8, 2019

(65) Prior Publication Data
US 2021/0046019 A1    Feb. 18, 2021

Related U.S. Application Data

(60) Provisional application No. 62/624,875, filed on Feb. 1, 2018.

(51) Int. Cl.
| A61K 38/12 | (2006.01) |
| A61K 9/107 | (2006.01) |
| A61K 31/122 | (2006.01) |
| A61K 31/337 | (2006.01) |
| A61K 38/13 | (2006.01) |
| A61K 47/42 | (2017.01) |

(52) U.S. Cl.
CPC ............ *A61K 31/122* (2013.01); *A61K 9/107* (2013.01); *A61K 31/337* (2013.01); *A61K 47/42* (2013.01)

(58) Field of Classification Search
CPC combination set(s) only.
See application file for complete search history.

(56) References Cited

FOREIGN PATENT DOCUMENTS

| EP | 2544663 B1 | 1/2018 |
| WO | 2008101344 A1 | 8/2008 |
| WO | 2010126319 A2 | 11/2010 |
| WO | 2014081443 A1 | 5/2014 |
| WO | 2014152795 A2 | 9/2014 |

OTHER PUBLICATIONS

Bonakdar, R. A., and E. Guarneri, "Coenzyme Q10" American Family Physician (2005), 72(6), pp. 1065-1070. (Year: 2005).*
Golub, T. R et al., "Molecular Classification of Cancer: Class Discovery and Class Prediction by Gene Expression Monitoring", Science (1999), vol. 286, pp. 531-537. (Year: 1999).*
Lala, P. K. and A. Orucevic, "Role of nitric oxide in tumor progression: Lessons from experimental tumors", Cancer and Metastasis Reviews (1998), 17(1), pp. 91-106. (Year: 1998).*
Mandal, S. M., A. Barbosa and O. Franco, "Lipopetides in microbial infection control: Scope and reality for industry", Biotechnology Advances (2013), 31: pp. 338-345. (Year: 2013).*
Hutchinson, J.A., S. Burholt, and I.W. Hamley, "Peptide hormones and lipopeptides: form self-assembly to therapeutic applications", J. Pept. Sci. (2017), 23: pp. 82-94. (Year: 2017).*
Sun J. et al., "Effect of particle size on solubility, dissolution rate, and oral bioavailability: evaluation using coenzyme Q10 as naked nanocrystals", Int. J. Nanomedicine (2012), 7: pp. 5733-5744. (Year: 2012).*
Peng, M., et al.. Primary coenzyme Q deficiency in Pdss2 mutant mice causes isolated renal disease. PLoS Genet, 2008. 4(4): p. e1000061.
Levavasseur, F., et al., Ubiquinone is necessary for mouse embryonic development but is not essential for mitochondrial respiration. J Biol Chem, 2001. 276(49): p. 46160-4.
Ewbank, J.J., et al., Structural and functional conservation of the Caenorhabditis elegans timing gene clk-1. Science, 1997. 275(5302): p. 980-3.
Nakai, D., et al., Mouse homologue of coq7/clk-1, longevity gene in Caenorhabditis elegans, is essential for coenzyme Q synthesis, maintenance of mitochondrial integrity, and neurogenesis. Biochem Biophys Res Commun, 2001. 289(2): p. 463-71.
Wang, Y., D. Oxer, and S. Hekimi, Mitochondrial function and lifespan of mice with controlled ubiquinone biosynthesis. Nat Commun, 2015. 6: p. 6393.
Bhagavan, H.N. and R.K. Chopra, Plasma coenzyme Q10 response to oral ingestion of coenzyme Q10 formulations. Mitochondrion, 2007. 7 Suppl: p. S78-88.
Seo, D.W., et al., Self-microemulsifying formulation-based oral solution of coenzyme Q10. Yakugaku Zasshi, 2009. 129(12): p. 1559-63.

(Continued)

*Primary Examiner* — Amanda L. Aguirre
*Assistant Examiner* — Sagar Patel
(74) *Attorney, Agent, or Firm* — Lavery, De Billy, LLP; S. Serge Shahinian

(57) ABSTRACT

The present disclosure concerns methods and formulations for delivery of hydrophobic agents (such as ubiquinone or poorly soluble drugs) for therapeutic and bioanalytical use. It further concerns use of lipopeptides (e.g. caspofungin) or surfactants to solubilize hydrophobic agents and thus increase their bioavailability. Also described are therapeutic methods for the treatment of conditions that benefit from such hydrophobic agents. The present disclosure further relates to methods of identifying drug candidates for treatment of ubiquinone deficiency.

8 Claims, 31 Drawing Sheets
Specification includes a Sequence Listing.

(56) References Cited

OTHER PUBLICATIONS

Kommuru, T.R., et al., Self-emulsifying drug delivery systems (SEDDS) of coenzyme Q10: formulation development and bioavailability assessment. Int J Pharm, 2001. 212(2): p. 233-46.
Schulz, C., et al., Comparison of the relative bioavailability of different coenzyme Q10 formulations with a novel solubilizate (Solu Q10). Int J Food Sci Nutr, 2006. 57(7-8): p. 546-55.
Chopra, R.K., et al., Relative bioavailability of coenzyme Q10 formulations in human subjects. Int J Vitam Nutr Res, 1998. 68(2): p. 109-13.
Liu, Z.X. and C. Altmann, Relative bioavailability comparison of different coenzyme Q10 formulations with a novel delivery system. Altern Ther Health Med, 2009. 15(2): p. 42-6.
Beg, S., S. Javed, and K. Kohli, Bioavailability enhancement of coenzyme Q10: an extensive review of patents. Recent Pat Drug Deliv Formul, 2010. 4(3): p. 245-55.
Cho, H., J. Gao, and G.S. Kwon, PEG-b-PLA micelles and PLGA-b-PEG-b-PLGA sol-gels for drug delivery. J Control Release, 2016. 240: p. 191-201.
Wang, Y. and S. Hekimi, Molecular genetics of ubiquinone biosynthesis in animals. Crit Rev Biochem Mol Biol, 2013. 48(1): p. 69-88.
Wang, Y. and S. Hekimi, Mitochondrial respiration without ubiquinone biosynthesis. Hum Mol Genet, 2013. 22(23): p. 4768-83).
McCarthy, J.J., et al., Inducible Cre transgenic mouse strain for skeletal muscle-specific gene targeting. Skelet Muscle, 2012. 2(1): p. 8.
Sohal, D.S., et al., Temporally regulated and tissue-specific gene manipulations in the adult and embryonic heart using a tamoxifen-inducible Cre protein. Circ Res, 2001. 89(1): p. 20-5.
Engblom, D., et al., Glutamate receptors on dopamine neurons control the persistence of cocaine seeking. Neuron, 2008. 59(3): p. 497-508.
Hutchinson, J. A. et al. "Peptide Hormones and Lipopeptides: From Self-Assembly to Therapeutic Applications". 2017. J. Pept. Sci. vol. 23, pp. 82-94 ISSN: 1099-1387 (Electronic).
Mandal, S. M. et al. "Lipopeptides in Microbial Infection Control: Scope and Reality for Industry". 2013. Biotechnology Advances. vol. 31, pp. 338-345 ISSN: 1873-1899 (Electronic).
Doimo, M. et al. "Genetics of Coenzyme Q10 Deficiency". 2014. Molecular Syndromology. vol. 5, pp. 156-162 ISSN: 1661-8777 (Electronic).
Ben-Meir, A. et al. "Coenzyme Q10 Restores Oocyte Mitochondrial Function and Fertility During Reproductive Aging". 2015. Aging Cell. vol. 14, pp. 887-895 ISSN: 1474-9726 (Electronic.
Sun, J. et al. "Effect of Particle size on Solubility, Dissolution Rate and Oral Bioavailability: Evaluation Using Coenzyme Q10 as Naked Nanocrystals". 2012. Int. J. Nanomedicine. vol. 7, pp. 5733-5744 ISSN: 1178-2013 (Electronic).
Celik, B. et al. "Design, optimization and characterization of coenzyme Q10-and D-panthenyl triacetate-loaded liposomes". 2017. Int. J. Nanomedicine. vol 12. pp. 4869-4878.
Takada, M. et al. "Targeting of Coenzyme Q10 Solubilized with Soy Lecithin to Heart of Guinea Pigs". 1985. J. Nutr. Sci. Vitaminol., vol. 31. No. 1. pp. 115-120.
PCT International Searching Authority "International Search Report and The Written Opinion". dated 2019. pp. 1-14.
Wang, Y. and Hekimi, S., Micellization of coenzyme Q by the fungicide caspofungin allows for safe intravenous administration to reach extreme supraphysiological concentrations, Redox Biology 36:101680, 2020.
Wang, H. et al., "Coumarins as new matrices for matrix-assisted laser-desorption/ionization Fourier transform ion cyclotron resonance mass spectrometric analysis of hydrophobic compounds", Analytica Chimica Acta, 882:49-57, 2015.
Adams, E.K., "In vitro Synergistic Activity of Caspofungin Plus Polymyxin B Against Fluconazole-Resistant Candida glabrata", The American Journal of the Medical Sciences, 351:265-270, 2016 (Abstract).
Supplementary European Search Report in respect of EP 19746864. 8, Jan. 1, 2022.

* cited by examiner

FORMULATIONS FOR IMPROVING THE DELIVERY OF HYDROPHOBIC AGENTS

CROSS-REFERENCE TO RELATED APPLICATIONS

The present application is a National Stage Application of PCT Application No. PCT/CA2019/050120 filed on Jan. 31, 2019 and published in English under PCT Article 21(2), which claims the benefit of U.S. Provisional Application Ser. No. 62/624,875 filed on Feb. 1, 2018, which is incorporated herein by reference in its entirety.

SEQUENCE LISTING

Pursuant to 37 C.F.R. 1.821(c), a sequence listing is submitted herewith as an ASCII compliant text file named "11168-480-SeqList.txt" created Jul. 29, 2020 and having a size of about 36,000 bytes. The computer readable form is incorporated herein by reference.

FIELD OF THE DISCLOSURE

The present disclosure concerns methods and formulations for improving the delivery of hydrophobic agents, such as, ubiquinone and poorly soluble drugs, and uses thereof, such as therapeutic uses.

BACKGROUND OF THE DISCLOSURE

Many drug and drug candidates are hydrophobic which causes significant problems in producing formulations of a sufficiently high bioavailability and hence hinders their therapeutic and medicinal utility.

Ubiquinone (UQ; 2,3-dimethoxy-5-methyl-6-polyprenyl-1,4-benzoquinone) is a typical representative of these types of compounds. UQ is also known as coenzyme Q (CoQ). It is a large lipophilic molecule found in all organisms that performs oxidative phosphorylation to meet energy demands. In the mitochondrial respiratory chain, it serves as a mobile electron carrier transporting electrons from Complex I and II as well as from other mitochondrial dehydrogenases to Complex III. Additionally, it takes part in a number of other cellular processes. UQ is a source of reactive oxygen species (ROS) when partially reduced and it has also been described to have antioxidant capacity. Furthermore, it participates in extra-mitochondrial electron transport systems and may be involved in the regulation of the mitochondrial permeability transition pore.

UQ is a large molecule composed of a benzoquinone head and a polyisoprenoid tail, whose length is species-specific. Living organisms can contain one or more types of UQ isoforms, but usually a single isoform dominates in abundance. In humans, the predominant UQ species contains a side chain of 10 isoprene units and is designated as ubiquinone-10 ($UQ_{10}$). Rodents have mainly ubiquinone-9 ($UQ_9$) with 9 isoprene unites in the side chain, and also have small amounts of $UQ_{10}$. UQ has practically no solubility in water which greatly limits its therapeutic utility.

UQ is an endogenous compound that is synthesized in all cells and tissues of the body. Its biosynthetic pathway is highly conserved from yeast to humans. So far, at least 10 nuclear (COQ) genes are known to be necessary for UQ biosynthesis in mammals. In humans, such genes include, but are not limited to ADCK3/CABC1, COQ2, COQ3, COQ4, COQ5, COQ6, COQ7, COQ9, PDSS1 and RDSS2. In mouse, such genes include, but are not limited to Pdss1, Pdss2, Coq2, Coq3, Coq4, Coq5, Coq6, Coq7/Mclk1, Coq8, and Coq9. This application mentions in particular 2 genes that are required for 2 different steps in UQ biosynthesis. One is the mouse Pdss2 gene, which is required for an earlier step in UQ biosynthesis, i.e., the synthesis of the polyisoprenyl tail [1]. The other is the Mclk1/Coq7 gene encoding the mitochondrial enzyme that catalyzes the penultimate step of the UQ biosynthetic pathway, the hydroxylation of 6-demethoxyubiquinone (DMQ) to form 6-hydroxyubiquinone [2-4]. In the mouse, full knockout of a UQ biosynthetic gene results in prenatal death [2, 4]. Mclk1 knockout mouse embryonic fibroblasts (MEFs) generated by infecting the MEFs obtained from $Mclk1^{loxP/loxP}$ embryos with a Cre-expressing virus are fully viable under standard (glucose) culture conditions, in spite of the absent UQ production (Wang et al., 2013). They still display some mitochondrial respiration but are unviable in medium containing galactose instead of glucose, because of a need for glycolysis when mitochondrial respiration is as severely impaired as it is by the lack of UQ. Supplementation with UQ molecules of various chain lengths or 2,4-dihydroxybenzoic acid (2,4-DHB) can rescue the cells' survival in galactose medium. 2,4-DHB is a synthetic unnatural analogue of the direct precursor of the UQ benzoquinone ring (4-HB). It structurally differs from 4-HB by having one more hydroxyl group at the position where the MCLK1 enzyme would catalyze the hydroxylation of DMQ. Biochemically, cells can use this alternative precursor for UQ biosynthesis and therefore 2,4-DHB treatment can lead to restoration of endogenous UQ synthesis in Mclk1 knockout cells and animals, resulting in phenotypic rescue [5].

Mutation(s) in any of the COQ genes produces primary deficiency which is often a severe debilitating illness that tends to affect multiple organs and tissues in the body and has a high mortality rate. Most primary UQ deficiency patients are juvenile onset and present with severe mitochondrial disease phenotypes such as encephalomyopathy, nephropathy, cerebellar ataxia, lactic acidosis and seizures. More than 25 distinct pathogenic mutations in 8 different COQ genes have been identified. UQ levels also may be affected by other genetic defects that are not directly involved in the biosynthetic process of UQ. Patients with mutations in these genes are considered to have secondary UQ deficiency. In humans, such genes include, but are not limited to MADD, BRAF, ETFDH, ARTX, BRAF, or MFN2. In addition, as used herein, the term "secondary ubiquinone deficiency" also refers to inadequate (e.g., decreased) levels of UQ that occur in the course of other diseases. For example, UQ deficiency has been reported in patients with a variety of mitochondrial diseases, especially those with mitochondrial DNA deletions, and lower than normal levels of $UQ_{10}$ (the major form of UQ in human) were reported to accompany age-related diseases, such as heart disease and Parkinson's disease. The fundamental role of UQ in mitochondrial function makes it important to correct its deficit in situations where its production and/or function are inadequate. Moreover, effectively boosting cellular UQ content potentially could benefit a variety of other conditions, especially, mitochondrial diseases. Indeed, in clinical populations, UQ has also been recommended as an adjunct treatment for a variety of chronic diseases such as chronic heart failure, muscular dystrophies, allergy, kidney failure, cancer, and diabetes. Ubiquinone is also widely consumed as an anti-aging nutraceutical.

UQ replacement therapy is the only available treatment for UQ deficiency. There are a variety of commercial $UQ_{10}$ formulations available as supplements. Because of its high hydrophobicity, $UQ_{10}$ is typically provided as an oily formulation for oral use. Animal studies demonstrated that dietary UQ is not taken up by most tissues, except by the liver, ovary and brown adipose tissue [5].

In addition to UQ, some derivatives of UQ have also been developed for therapeutic uses, such as idebenone and mitochondrial $CoQ_{10}$ (MitoQ). All of them have also failed to provide strong or significant therapeutic effects, likely because the derivatives do not possess the biological properties of ubiquinone or because of the difficulty in achieving sufficient uptake into the body and its cells.

Other examples of drugs having poor water solubility include paclitaxel, etoposide, camptothecin, carbamazepine, rapamycin, tamoxifen, flunarizine, pimozide, trifluoperazine, mebendazole, phenytoin, and dexamethasone to mention just a few.

There is thus a need for increasing aqueous solubility of poorly soluble drugs and to develop new parenteral formulations of hydrophobic compounds, like UQ, for therapeutic purposes such as the treatment of UQ deficiency.

The present disclosure refers to a number of documents, the content of which is herein incorporated by reference in their entirety.

SUMMARY OF THE DISCLOSURE

The present disclosure concerns methods and formulations for improving the delivery of hydrophobic agents, such as, ubiquinone and poorly soluble drugs, and uses thereof, such as therapeutic uses.

More specifically, in accordance with aspects of the present disclosure, there are provided the following items:

1. A composition comprising a mixture of caspofungin and/or a pharmaceutically or biologically acceptable salt thereof and a hydrophobic agent in an aqueous solution.
2. The composition of item 1, wherein the caspofungin or pharmaceutically or biologically acceptable salt thereof solubilizes the hydrophobic agent in the aqueous solution.
3. The composition of item 1 or 2 comprising a suspension of micelles composed of caspofungin and/or the pharmaceutically or biologically acceptable salt thereof and the hydrophobic agent.
4. The composition of any one of items 1 to 3, wherein the composition is free of liposomes comprising the caspofungin and/or pharmaceutically or biologically acceptable salt thereof and the hydrophobic agent.
5. The composition of any one of items 1 to 4, wherein the pharmaceutically or biologically acceptable salt of caspofungin is caspofungin acetate.
6. The composition of any one of items 1 to 5, wherein the hydrophobic agent is poorly soluble in water.
7. The composition of item 6, wherein the hydrophobic agent has a solubility of less than 30 mg/ml in water at ambient temperature.
8. The composition of item 6 or 7, wherein the hydrophobic agent has a solubility of less than 20 mg/ml in water at ambient temperature.
9. The composition of any one of items 6 to 8, wherein the hydrophobic agent has a solubility of less than 10 mg/ml in water at ambient temperature.
10. The composition of any one of items 6 to 9, wherein the hydrophobic agent has a solubility of less than 5 mg/ml in water at ambient temperature.
11. The composition of any one of items 6 to 10, wherein the hydrophobic agent has a solubility of less than 1 mg/ml in water at ambient temperature.
12. The composition of any one of items 1 to 11, wherein the hydrophobic agent is ubiquinone.
13. The composition of any one of items 1 to 11, wherein the hydrophobic agent is a taxane drug.
14. The composition of any one of items 1 to 11 and 13, wherein the hydrophobic agent is paclitaxel, docetaxel, cabazitaxel, or any combination thereof.
15. The composition of any one of items 1 to 11, 13 and 14, wherein the hydrophobic agent is paclitaxel.
16. The composition of any one of items 1 to 15, wherein the hydrophobic agent is ubiquinone, SN-38, etoposide, paclitaxel, docetaxel, cabazitaxel, campothecin, cisplatin, temsirolimus, teniposide, Cabozantinib, Nintedanib, XAV-939, ICG-001, SANT75, HPI1, rapamycin, Buparlisib, curcumin, luteolin, retinoic acid, dihydroergotamine, lorazepam, propanidid, diazepam, nimodipine, carbamazepine, glipizide, omeprazole, tarazepide, griseofulvin, acyclovir, albendazole, azithromycin, itraconazole, fluconazole, flufenamic acid, aceclofenac, diflunisal, fenofibrate, budesonide, clofazimine, spironolactone, melarsoprol, nifedipine, cyclosporin, piroxicam, finasteride, or any combination thereof.
17. The composition of any one of items 3 to 16, wherein the micelles are less than 200 nm in diameter.
18. A composition comprising a mixture of a lipopeptide compound and/or a pharmaceutically or biologically acceptable salt thereof and a hydrophobic agent in an aqueous solution.
19. The composition of item 18, wherein the lipopeptide compound or pharmaceutically or biologically acceptable salt thereof solubilizes the hydrophobic agent in the aqueous solution.
20. The composition of item 18 or 19 comprising a suspension of micelles composed of the lipopeptide compound and/or the pharmaceutically or biologically acceptable salt thereof and the hydrophobic agent.
21. The composition of any one of items 18 to 20, wherein the composition is free of liposomes comprising the lipopeptide compound and/or pharmaceutically or biologically acceptable salt thereof and the hydrophobic agent.
22. The composition of any one of items 20 to 21, wherein the micelles are less than 200 nm in diameter.
23. The composition of any one of items 18 to 24, wherein the lipopeptide compound is soluble in aqueous solution.
24. The composition of any one of items 18 to 23, wherein the lipopeptide compound comprises a peptide moiety and a hydrophobic moiety.
25. The composition of item 24, wherein the peptide moiety comprises a cyclic peptide.
26. The composition of item 28 or 29, wherein the peptide moiety comprises a peptide comprising 4 to 30, 4 to 25, 4 to 20, 4 to 16, 4 to 14, 4 to 12, 6 to 30, 6 to 25, 6 to 20, 6 to 16, 6 to 14, 6 to 12, 8 to 30, 8 to 25, 8 to 20, 8 to 16, 8 to 14, or 8 to 12 amino acids.
27. The composition of any one of items 24 to 26, wherein the hydrophobic moiety comprises a hydrophobic chain of 6 to 22, 6 to 20, 6 to 18, 6 to 16, 6 to 14, 8 to 20, 8 to 18, 8 to 16, 8 to 14, 10 to 20, 10 to 18, 10 to 16, or 10 to 14 carbons in length.
28. The composition item 27, wherein the hydrophobic chain comprises a linear backbone of 6 to 22, 6 to 20, 6 to 18, 6 to 16, 6 to 14, 8 to 20, 8 to 18, 8 to 16, 8 to 14, 10 to 20, 10 to 18, 10 to 16, or 10 to 14 carbons in length.
29. The composition of item 28, wherein the hydrophobic moiety further comprises one or more alkyl branches attached to the linear backbone.

30. The composition of any one of items 24 to 29, wherein the hydrophobic moiety does not contain 2 or more aromatic rings.
31. The composition of any one of items 18 to 24, wherein the lipopeptide compound is caspofungin, pneumocandin, aculeacin A, surfactin, iturin A, fengycin, lichenysin, daptomycin, viscosin, amphomycin, tsushimycin, friulimicin B, polymyxin, octapeptin, polypeptin, fusaricidin, tridecaptin, kurstakin, amphisin, lokisin, hodersin, tensin, massetolide, viscosinamide, pseudodesmin, pseudophomin, amphisin, syringomycin, syringopeptin, tolaasin, putisolvin, orfamide, syringafactin, entolysin, cichofactins, maribasins, ecomycin, pseudomycins, and/or cormycin A, or a pharmaceutically or biologically acceptable salt thereof.
32. The composition of any one of items 16 to 31, wherein the lipopeptide compound is caspofungin or a pharmaceutically or biologically acceptable salt thereof.
33. The composition of item 32, wherein the pharmaceutically or biologically acceptable salt of caspofungin is caspofungin acetate.
34. The composition of any one of items 18 to 33, wherein the hydrophobic agent is poorly soluble in water.
35. The composition of item 34, wherein the hydrophobic agent has a solubility of less than 30 mg/ml in water at ambient temperature.
36. The composition of item 34 or 35, wherein the hydrophobic agent has a solubility of less than 20 mg/ml in water at ambient temperature.
37. The composition of any one of items 34 to 36, wherein the hydrophobic agent has a solubility of less than 10 mg/ml in water at ambient temperature.
38. The composition of any one of items 34 to 37, wherein the hydrophobic agent has a solubility of less than 5 mg/ml in water at ambient temperature.
39. The composition of any one of items 34 to 38, wherein the hydrophobic agent has a solubility of less than 1 mg/ml in water at ambient temperature.
40. The composition of any one of items 18 to 39, wherein the hydrophobic agent is ubiquinone.
41. The composition of any one of items 18 to 39, wherein the hydrophobic agent is a taxane drug.
42. The composition of any one of items 18 to 39 and 41, wherein the hydrophobic agent is paclitaxel, docetaxel, cabazitaxel, or any combination thereof.
43. The composition of any one of items 18 to 39, 41 and 42, wherein the hydrophobic agent is paclitaxel.
44. The composition of any one of items 18 to 43, wherein the hydrophobic agent is ubiquinone, SN-38, etoposide, paclitaxel, docetaxel, cabazitaxel, campothecin, cisplatin, temsirolimus, teniposide, Cabozantinib, Nintedanib, XAV-939, ICG-001, SANT75, HPI1, rapamycin, Buparlisib, curcumin, luteolin, retinoic acid, dihydroergotamine, lorazepam, propanidid, diazepam, nimodipine, carbamazepine, glipizide, omeprazole, tarazepide, griseofulvin, acyclovir, albendazole, azithromycin, itraconazole, fluconazole, flufenamic acid, aceclofenac, diflunisal, fenofibrate, budesonide, clofazimine, spironolactone, melarsoprol, nifedipine, cyclosporin, piroxicam, finasteride, or any combination thereof.
45. A composition comprising a mixture of a surfactant and a hydrophobic agent in an aqueous solution, wherein the hydrophobic agent is ubiquinone.
46. The composition of item 45, wherein the surfactant solubilizes the hydrophobic agent in the aqueous solution.
47. The composition of item 45 or 46 comprising a suspension of micelles composed of the surfactant and the hydrophobic agent.
48. The composition of any one of items 45 to 47, wherein the composition is free of liposomes comprising the surfactant and the hydrophobic agent.
49. The composition of any one of items 45 to 48, wherein the surfactant is an amphiphilic block copolymer.
50. The composition of item 49, wherein the surfactant is PLGA-PEG-PLGA.
51. The composition of one of items 15 to 48, wherein the surfactant is tetradecyl trimethyl ammonium bromide (TTAB), benzalkonium chloride (BAC) and/or a saponin.
52. The composition of any one of items 1 to 51, which is substantially free of alcohol.
53. The composition of any one of items 1 to 52, which is substantially free of oil or an oil-based compound or oil derivative.
54. The composition of any one of items 1 to 53, which is substantially free of polyethoxylated castor oil.
55. The composition of any one of items 1 to 54, for use in delivering the hydrophobic agent to a cell.
56. The composition for use of item 55, wherein the cell is in vitro.
57. The composition for use of item 55, wherein the cell is in vivo.
58. The composition for use of item 57, wherein the cell is in a human or an animal subject.
59. Use of the composition of any one of items 1 to 54, for delivering the hydrophobic agent to a cell.
60. Use of the composition of any one of items 1 to 54, for the preparation of a formulation for delivering the hydrophobic agent to a cell.
61. The use of item 59 or 60, wherein the cell is in vitro.
62. The use of item 59 or 60, wherein the cell is in vivo.
63. The use of item 62, wherein the cell is in a human or an animal subject.
64. A method of delivering a hydrophobic agent to a cell, the method comprising contacting the composition of any one of items 1 to 54 with the cell.
65. The use of item 64, wherein the cell is in vitro.
66. The use of item 64, wherein the cell is in vivo.
67. The use of item 66, wherein the cell is in a human or an animal subject.
68. A method of preparing the composition of any one of items 1 to 17 and 52 to 54, comprising solubilizing the hydrophobic agent with caspofungin and/or the pharmaceutically or biologically acceptable salt thereof, to provide the composition.
69. The method of item 68, comprising forming a suspension of micelles composed of caspofungin and/or the pharmaceutically or biologically acceptable salt thereof, and the hydrophobic agent.
70. A method of preparing the composition of any one of items 18 to 44 and 52 to 54, comprising solubilizing the hydrophobic agent with the lipopeptide compound and/or the pharmaceutically or biologically acceptable salt thereof, to provide the composition.
71. The method of item 70, comprising forming a suspension of micelles composed of the lipopeptide compound and/or the pharmaceutically or biologically acceptable salt thereof, and the hydrophobic agent.
72. A method of preparing the composition of any one of items 45 to 54, comprising solubilizing the hydrophobic agent with the surfactant, to provide the composition.

73. The method of item 72, comprising forming a suspension of micelles composed of the surfactant and the hydrophobic agent.
74. A composition obtainable by the method of any one of items 68 to 73.
75. A method of treating or alleviating the symptoms of a disease or a condition in a subject in need thereof that would benefit from an increase in intracellular ubiquinone levels, the method comprising administering a therapeutically effective amount of the composition of any one of items 1 to 54 to the subject, wherein the hydrophobic agent is ubiquinone, so as to treat or alleviate the symptoms of the disease or the condition in the subject.
76. The method of item 75, wherein the composition comprises caspofungin or a pharmaceutically or biologically acceptable salt thereof and ubiquinone.
77. The method of item 76, wherein the composition comprises caspofungin acetate and ubiquinone.
78. The method of any one of items 75 to 77, wherein the subject is a human or an animal subject.
79. The method of any one of items 75 to 78, wherein the disease or the condition is associated with mitochondrial dysfunction.
80. The method of item 79, further comprising determining the presence of mitochondrial dysfunction in the subject prior to administering the composition.
81. The method of any one of items 75 to 80, wherein the disease or the condition is a mitochondrial disease, Parkinson's disease, Huntington's disease, Alzheimer's disease, amyotrophic lateral sclerosis, type I diabetes, type II diabetes, cardiac failure, ischemic heart disease, hypertension, coronary artery disease, idiopathic dilated cardiomyopathy, pulmonary arterial hypertension, ataxia, bipolar depression, Duchenne muscular dystrophy, fibromyalgia, cancer, asthenozoospermia, periodontal disease, migraine, pre-eclampsia, Down's syndrome, aging and/or a ubiquinone deficiency.
82. The method of any one of items 75 to 81, wherein the disease or condition is associated with a ubiquinone deficiency.
83. The method of item 82 further comprising determining the presence of ubiquinone deficiency in the subject prior to administering the composition.
84. The method of item 82 or 83, wherein the disease or condition is associated with primary ubiquinone deficiency.
85. The method of item 82 or 83, wherein the disease or condition is associated with secondary ubiquinone deficiency.
86. The composition of any one of items 1 to 54 for use in treating or alleviating the symptoms of a disease or a condition in a subject in need thereof that would benefit from an increase in intracellular ubiquinone levels.
87. The composition for use of item 86, wherein the composition comprises caspofungin or a pharmaceutically or biologically acceptable salt thereof and ubiquinone.
88. The composition for use of item 87, wherein the composition comprises caspofungin acetate and ubiquinone.
89. The composition for use of any one of items 86 to 88, wherein the subject is a human or an animal subject.
90. The composition for use of any one of items 86 to 89, wherein the disease or the condition is associated with mitochondrial dysfunction.
91. The composition for use of item 90, further comprising determining the presence of mitochondrial dysfunction in the subject prior to administering the formulation.
92. The composition for use of any one of items 86 to 91, wherein the disease or the condition is a mitochondrial disease, Parkinson's disease, Huntington's disease, Alzheimer's disease, amyotrophic lateral sclerosis, type I diabetes, type II diabetes, cardiac failure, ischemic heart disease, hypertension, coronary artery disease, idiopathic dilated cardiomyopathy, pulmonary arterial hypertension, ataxia, bipolar depression, Duchenne muscular dystrophy, fibromyalgia, cancer, asthenozoospermia, periodontal disease, migraine, pre-eclampsia, Down's syndrome, aging and/or a ubiquinone deficiency.
93. The composition for use of any one of items 86 to 92, wherein the disease or condition is associated with a ubiquinone deficiency.
94. The composition for use of item 93, further comprising determining the presence of ubiquinone deficiency in the subject prior to administering the composition.
95. The composition for use of item 93 or 94, wherein the disease or condition is associated with primary ubiquinone deficiency.
96. The composition for use of item 93 or 94, wherein the disease or condition is associated with secondary ubiquinone deficiency.
97. Use of the composition of any one of items 1 to 54 for treating or alleviating the symptoms of a disease or a condition in a subject in need thereof that would benefit from an increase in intracellular ubiquinone levels.
98. Use of the composition of any one of items 1 to 54 for the preparation of a medicament for treating or alleviating the symptoms of a disease or a condition in a subject in need thereof that would benefit from an increase in intracellular ubiquinone levels.
99. The use of item 97 or 98, wherein the composition comprises caspofungin or a pharmaceutically or biologically acceptable salt thereof and ubiquinone.
100. The use of item 99, wherein the composition comprises caspofungin acetate and ubiquinone.
101. The use of any one of items 97 to 100, wherein the subject is a human or an animal subject.
102. The use of any one of items 97 to 101, wherein the disease or the condition is associated with mitochondrial dysfunction.
103. The use of item 102, further comprising determining the presence of mitochondrial dysfunction in the subject prior to administering the composition or medicament.
104. The use of any one of items 97 to 103, wherein the disease or the condition is a mitochondrial disease, Parkinson's disease, Huntington's disease, Alzheimer's disease, amyotrophic lateral sclerosis, type I diabetes, type II diabetes, cardiac failure, ischemic heart disease, hypertension, coronary artery disease, idiopathic dilated cardiomyopathy, pulmonary arterial hypertension, ataxia, bipolar depression, Duchenne muscular dystrophy, fibromyalgia, cancer, asthenozoospermia, periodontal disease, migraine, pre-eclampsia, Down's syndrome, aging and/or a ubiquinone deficiency.
105. The use of any one of items 97 to 104, wherein the disease or condition is associated with a ubiquinone deficiency.
106. The use of item 105, further comprising determining the presence of ubiquinone deficiency in the subject prior to administering the composition or medicament.
107. The composition for use of item 105 or 106, wherein the disease or condition is associated with primary ubiquinone deficiency.

108. The composition for use of item 105 or 106, wherein the disease or condition is associated with secondary ubiquinone deficiency.
109. A method of treating cancer or reducing cancer cell proliferation in a subject in need thereof, the method comprising administering a therapeutically effective amount of the composition of any one of items 1 to 54 to the subject, wherein the hydrophobic agent is an anticancer agent.
110. The method of item 109, wherein the composition comprises caspofungin or a pharmaceutically or biologically acceptable salt thereof and the anticancer agent.
111. The method of item 110, wherein the composition comprises caspofungin acetate and the anticancer agent.
112. The method of any one of items 109 to 111, wherein the subject is a human or an animal subject.
113. The method of any one of items 109 to 112, wherein the hydrophobic agent is a taxane drug.
114. The method of item 113, wherein the hydrophobic agent is paclitaxel, docetaxel, cabazitaxel, or any combination thereof.
115. The method of any one of items 109 to 114, wherein the cancer is leukemia, breast cancer, cervical cancer or prostate cancer.
116. The composition of any one of items 1 to 54 for use in treating cancer or reducing cancer cell proliferation in a subject in need thereof, wherein the hydrophobic agent is an anticancer agent.
117. The composition for use of item 116, wherein the composition comprises caspofungin or a pharmaceutically or biologically acceptable salt thereof and the anticancer agent.
118. The composition for use of item 117, wherein the composition comprises caspofungin acetate and ubiquinone.
119. The composition for use of any one of items 116 to 118, wherein the subject is a human or an animal subject.
120. The composition for use of any one of items 116 to 119, wherein the hydrophobic agent is a taxane drug.
121. The composition for use of item 120, wherein the hydrophobic agent is paclitaxel, docetaxel, cabazitaxel, or any combination thereof.
122. The composition for use of any one of items 116 to 121, wherein the cancer is leukemia, breast cancer, cervical cancer or prostate cancer.
123. Use of the composition of any one of items 1 to 54 for treating cancer or reducing cancer cell proliferation in a subject in need thereof, wherein the hydrophobic agent is an anticancer agent.
124. Use of the composition of any one of items 1 to 54 for the preparation of a medicament for treating cancer or reducing cancer cell proliferation in a subject in need thereof, wherein the hydrophobic agent is an anticancer agent.
125. The use of item 123 or 124, wherein the composition comprises caspofungin or a pharmaceutically or biologically acceptable salt thereof and the anticancer agent.
126. The use of item 125, wherein the composition comprises caspofungin acetate and the anticancer agent.
127. The use of any one of items 123 to 126, wherein the subject is a human or an animal subject.
128. The use of any one of items 123 to 127, wherein the hydrophobic agent is a taxane drug.
129. The use of item 128, wherein the hydrophobic agent is paclitaxel, docetaxel, cabazitaxel, or any combination thereof.
130. The use of any one of items 123 to 129, wherein the cancer is leukemia, breast cancer, cervical cancer or prostate cancer.
131. A method of identifying a compound for the treatment or the alleviation of symptoms of a condition associated with a ubiquinone deficiency in a subject in need thereof, the method comprising:
  a) providing a living cells lacking the ability to express a Mclk1 gene or a Mclk1 gene ortholog;
  b) combining the test agent with the Mclk1 knockout cell in a first respiration-dependent medium to provide a first cell culture and determining the ability of the Mclk1 knockout cell to survive in the first cell culture or the rate of respiration of the Mclk1 knockout cell; and
  c) characterizing the test agent as being useful in the treatment or the alleviation of symptoms of the condition associated with the ubiquinone deficiency if the test agent is determined to allow the survival of the Mclk1 knockout cell in the first cell culture or increase the respiration rate of the Mclk1 knockout cell.
132. The method of item 131 wherein the first respiration-dependent medium comprises 2,4-dihydroxybenzoic acid (2,4-DHB) in an amount insufficient to allow survival of the Mclk1 knockout cell in the absence of the test agent.
133. The method of item 131 or 132, further comprising:
  d) providing a living cell lacking the ability to express (i) a Mclk1 gene or a Mclk1 gene ortholog and (ii) a Pdss2 gene or a Pdss2 gene ortholog;
  e) combining the test agent with the Pdss2/Mclk1 double knockout cell in a second respiration-dependent medium to provide a second cell culture and determining the ability of the Pdss2/Mclk1 double knockout cell to survive in the first cell culture; and
  f) characterizing the test agent as being useful in the treatment or the alleviation of symptoms of the condition associated with the ubiquinone deficiency if the test agent is determined to allow the survival of the Pdss2/Mclk1 double knockout cell in the second cell culture.
134. The method of item 133 wherein the second respiration-dependent medium comprises ubiquinone in an amount insufficient to allow survival of the Pdss2/Mclk1 double knockout cell in the absence of the test agent.
135. The method of any one of items 131 to 134, further comprising determining ubiquinone levels in the transgenic cell in the presence and absence of the test compound, optionally in combination with 2,4-DHB or ubiquinone.
136. The method of any one of items 131 to 135, further comprising:
  g) combining the Pdss2/Mclk1 double knockout and/or the Mclk1 single knockout cell with a positive control agent in a third respiration-dependent medium to provide a third cell culture and determining the ability of the Pdss2/Mclk1 double knockout and/or the Mclk1 single knockout cell to survive in the third respiration-dependent medium; and
  h) characterizing the method as being useful for identifying agents for the treatment or the alleviations of symptoms of the condition associated with the ubiquinone deficiency in the subject if the presence of the positive control agent in the third respiration-dependent medium is determined to allow the survival of the Pdss2/Mclk1 double knockout and/or the Mclk1 single knockout cell.

137. The method of item 136, wherein the positive control agent is ubiquinone in an amount sufficient to allow survival of the Pdss2/Mclk1 double knockout and/or the Mclk1 single knockout cell in the absence of the test agent.
138. The method of any one of items 131 to 137 further comprising:
   i) combining the Pdss2/Mclk1 double knockout and/or the Mclk1 single knockout cell with a negative control agent in a fourth respiration-dependent medium to provide a fourth cell culture and determining the ability of the Pdss2/Mclk1 double knockout and/or the Mclk1 single knockout cell to survive in the fourth respiration-dependent medium; and
   j) characterizing the method as being useful for identifying agents for the treatment or the alleviations of symptoms of the condition associated with the ubiquinone deficiency in the subject if the presence of the negative control agent in the fourth respiration-dependent medium is determined to fail to allow the survival of the Pdss2/Mclk1 double knockout and/or the Mclk1 single knockout cell.
139. The method of item 138, wherein the negative control agent is dimethylsulfoxide (DMSO).
140. The method of any one of items 131 to 139, wherein the respiration-dependent medium lacks glucose.
141. The method of item 140, wherein respiration-dependent medium comprises a single carbohydrate source and the single carbohydrate source is galactose.
142. The method of any one of items 131 to 141, wherein survival is determined using a fluorescent or colorimetric assay.
143. The method of any one of items 131 to 142, wherein the Pdss2/Mclk1 double knockout and/or the Mclk1 single knockout cell are mammalian cells.
144. The method of item 143, wherein the mammalian cells are murine cells.
145. The method of any one of items 131 to 144, wherein the Pdss2/Mclk1 double knockout and/or the Mclk1 single knockout cell are located in an animal and the method for comprises administering the test agent to the animal.
146. A cell lacking the ability to express (i) a Mclk1 gene or a Mclk1 gene ortholog and (ii) a Pdss2 gene or a Pdss2 gene ortholog.
147. The cell of item 146, which is a Pdss2/Mclk1 double knockout cell.
148. A transgenic non-human animal bearing the Pdss2/Mclk1 double knockout cell of item 147.
149. A transgenic non-human animal bearing the Mclk1 single knockout cell.
150. A recombinant non-human cell bearing the Pdss2/Mclk1 double knockout.
151. A recombinant non-human cell bearing the Mclk1 single knockout.
152. An isolated recombinant cell bearing the Pdss2/Mclk1 double knockout.
153. An isolated recombinant cell bearing the Mclk1 single knockout.

Other objects, advantages and features of the present disclosure will become more apparent upon reading of the following non-restrictive description of specific embodiments thereof, given by way of example only with reference to the accompanying drawings.

BRIEF DESCRIPTION OF THE DRAWINGS

Having thus generally described the nature of the invention, reference will now be made to the accompanying drawings, showing by way of illustration, a preferred embodiment thereof, and in which.

DESCRIPTION OF ILLUSTRATIVE EMBODIMENTS

Definitions

Figure 1A:
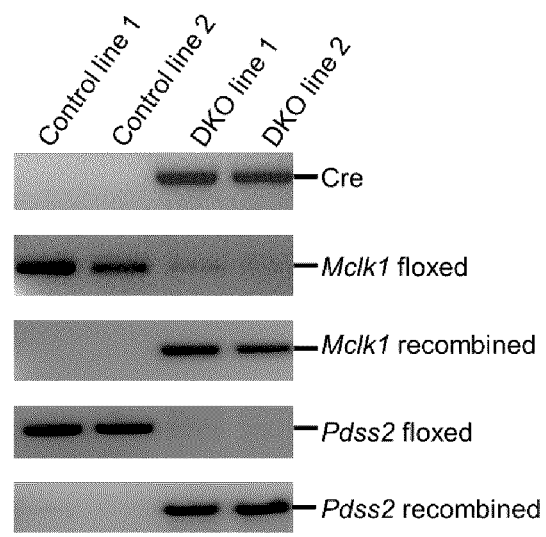
FIGS. 1A and 1B provide a verification of gene knockout and loss of ubiquinone (UQ) in Pdss2/Mclk1 double knockout (DKO) mouse embryonic fibroblasts (MEFs). The Cre-loxP recombination system was used to generate the Pdss2/Mclk1 DKO cells (see Example 1). (A) For both Pdss2 and Mclk1 genes, the recombined knockout allele but not the floxed allele was detected in Pdss2$^{loxP/loxP}$ Mclk1$^{loxP/loxP}$ MEFs after infection with pBabe-puro retroviral vector encoding Cre (pBabe-puro-Cre). RT-PCR analysis of cDNA derived from the DKO cells showed loss of expression for both the targeted genes. Therefore, the conversion of the floxed alleles ("loxP") into the knockout forms ("Δ") was virtually complete. (B) UQ$_9$ is absence in the DKO cells. The controls (Pdss2$^{loxP/loxP}$ Mclk1$^{loxP/loxP}$ MEFs infected with the empty pBabe-puro retroviral vector) contain UQ$_9$. In mice UQ$_9$ is the dominant form of UQ. Shown are HPLC chromatograms of cellular quinone extracts monitored at a wavelength of 275 nm.
Figure 1A:
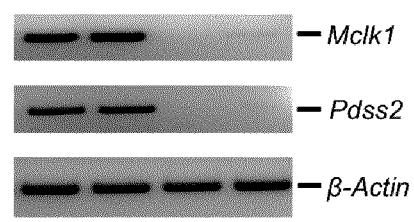

The use of the terms "a" and "an" and "the" and similar referents in the context of describing the technology (especially in the context of the following claims) are to be construed to cover both the singular and the plural, unless otherwise indicated herein or clearly contradicted by context.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods or processes described herein can be performed in any suitable order unless otherwise indicated herein or otherwise clearly contradicted by context. Further, in embodiments various steps may be repeated, to increase recovery and purification.

The use of any and all examples, or exemplary language (e.g., "such as") provided herein, is intended merely to better illuminate the disclosure and does not pose a limitation on the scope of the disclosure unless otherwise claimed.

No language in the specification should be construed as indicating any non-claimed element as essential to the practice of the disclosure.

As used herein when referring to numerical values or percentages, the term "about" has its ordinary meaning, and includes variations due to the methods used to determine the values or percentages, statistical variance and human error. Moreover, each numerical parameter in this application should at least be construed in light of the number of reported significant digits and by applying ordinary rounding techniques. In embodiments, it may mean plus or minus 10% of the numerical value qualified.

Unless otherwise defined, all technical and scientific terms used herein have the same meaning as commonly understood by one of ordinary skill in the art to which this disclosure belongs.

It is to be understood that the present disclosure is not limited to the particular embodiments described herein, as variations of these embodiments may be made and still fall within the scope of the present disclosure. It is also to be understood that the terminology employed is for the purpose of describing particular embodiments; and is not intended to be limiting.

In various aspects, this present disclosure is directed to compounds effective at increasing the aqueous solubility and thus bioavailability of hydrophobic agents such as ubiquinone or poorly soluble drugs. In a broad aspect, it is directed to methods of using a lipopeptide compound to enhance aqueous solubility and thus improve bioavailability of hydrophobic agents, for example for therapeutic or biological applications.

In an aspect, the present disclosure relates to a composition or formulation comprising a mixture of a lipopeptide compound (e.g., caspofungin and/or a pharmaceutically or biologically acceptable salt thereof) and a hydrophobic agent in an aqueous solution. In an embodiment, the lipopeptide compound (e.g., caspofungin and/or a pharmaceutically or biologically acceptable salt thereof) solubilizes the hydrophobic agent in the aqueous solution. In another embodiment, the composition or formulation comprises a suspension of micelles composed of the lipopeptide compound and the hydrophobic agent.

In a further aspect, the present disclosure relates to a composition or formulation comprising a mixture of a lipopeptide compound and/or a pharmaceutically or biologically acceptable salt thereof and a hydrophobic agent in an aqueous solution. In an embodiment the lipopeptide compound or pharmaceutically or biologically acceptable salt thereof solubilizes the hydrophobic agent in the aqueous solution. In an embodiment, the composition or formulation comprises a suspension of micelles composed of the lipopeptide compound and/or the pharmaceutically or biologically acceptable salt thereof and the hydrophobic agent. In an embodiment, the lipopeptide compound is caspofungin. In an embodiment, the salt of the lipopeptide compound is caspofungin acetate.

In a further aspect, the present disclosure relates to a composition or formulation comprising a mixture of a surfactant, a hydrophobic agent, such as ubiquinone, and an aqueous solution. In an embodiment, the surfactant solubilizes ubiquinone in the aqueous solution. In another embodiment, the composition or formulation comprises a suspension of micelles composed of the surfactant and ubiquinone. In another embodiment, the surfactant is caspofungin and/or a pharmaceutically or biologically acceptable salt thereof, such as caspofungin acetate. In an embodiment, the surfactant is an amphiphilic block copolymer, such as PLGA-PEG-PLGA. In further embodiments, the surfactant is tetradecyl trimethyl ammonium bromide (TTAB), benzalkonium chloride (BAC) and/or a saponin.

In embodiments, the micelles as described herein have a diameter of less than about 300, 250, 200, 150, or 100 nm. In embodiments, the micelles as described herein have a diameter of at least about 5, 10, 15, 20, 25, 30, 35, 40, 45 or 50 nm. In embodiments, the micelles described herein have a diameter of about 5 to about 300 nm, about 10 to about 300 nm, about 15 to about 300 nm, about 20 to about 300 nm, about 25 to about 300 nm, about 5 to about 250 nm, about 10 to about 250 nm, about 15 to about 250 nm, about 20 to about 250 nm, about 25 to about 250 nm, about 5 to about 200 nm, about 10 to about 200 nm, about 15 to about 200 nm, about 20 to about 200 nm, about 25 to about 200 nm, about 5 to about 150 nm, about 10 to about 150 nm, about 15 to about 150 nm, about 20 to about 150 nm, about 25 to about 150 nm, about 5 to about 100 nm, about 10 to about 100 nm, about 15 to about 100 nm, about 20 to about 100 nm, or about 25 to about 100 nm. Micelles may be prepared by any methods known in the art, such as sonication, homogenization, shaking, thin-film methods, dissolution, dialysis, emulsion, solvent evaporation, lyophilization or freeze drying, or combinations of such methods. In embodiments, such methods may further comprise filtration and/or centrifugation.

In embodiments, a "lipopeptide compound" as described herein comprises a peptide moiety and a hydrophobic moiety. In an embodiment, the peptide moiety and a hydrophobic moiety are directly attached to each other. In an embodiment, the peptide moiety and hydrophobic moiety are attached via a linker moiety.

In an embodiment, a "peptide moiety" as described herein comprises a linear peptide. In a further embodiment, the peptide moiety comprises a cyclic structure, such as a cyclic peptide. In a further embodiment the linear or cyclic peptide further comprises one or more peptide-containing branches.

In embodiments, a "peptide moiety" as described herein comprises a peptide comprising at least 4, 5, 6, 7, or 8 amino acids. In embodiments, the peptide moiety comprises a peptide comprising at least 4, 5, 6, 7, or 8 amino acids. In embodiments, the peptide moiety comprises a peptide comprising up to 10, 11, 12, 13, 14, 15 or 16, 20, 25 or 30 amino acids. In embodiments, the peptide moiety comprises a peptide comprising 4 to 30, 4 to 25, 4 to 20, 4 to 16, 4 to 14, 4 to 12, 6 to 30, 6 to 25, 6 to 20, 6 to 16, 6 to 14, 6 to 12, 8 to 30, 8 to 25, 8 to 20, 8 to 16, 8 to 14, or 8 to 12 amino acids.

In embodiments, a "hydrophobic moiety" as described herein comprises a hydrophobic chain of at least 6, 7, 8, 9 or 10 carbons in length. In embodiments, the hydrophobic moiety comprises a hydrophobic chain of up to 14, 15, 16, 17, 18, 19, 20, 21 or 22 carbons in length. In embodiments, the hydrophobic moiety comprises a hydrophobic chain of 6 to 22, 6 to 20, 6 to 18, 6 to 16, 6 to 14, 8 to 20, 8 to 18, 8 to 16, 8 to 14, 10 to 20, 10 to 18, 10 to 16, or 10 to 14 carbons in length. In an embodiment, the hydrophobic chain is an acyl chain.

In embodiments, a "hydrophobic chain" as described herein comprises one or more double bonds. In embodiments, the hydrophobic chain comprises a linear backbone of at least 6, 7, 8, 9 or 10 carbons in length. In embodiments, the hydrophobic chain comprises a linear backbone of up to 14, 15, 16, 17, 18, 19, 20, 21 or 22 carbons in length. In embodiments, the hydrophobic chain comprises a linear backbone of 6 to 22, 6 to 20, 6 to 18, 6 to 16, 6 to 14, 8 to 20, 8 to 18, 8 to 16, 8 to 14, 10 to 20, 10 to 18, 10 to 16, or 10 to 14 carbons in length. In embodiments, the hydrophobic moiety further comprises one or more alkyl branches attached to the linear backbone.

In an embodiment, the hydrophobic moiety does not contain 2 or more aromatic rings. In a further embodiment, the hydrophobic moiety does not contain an aromatic ring.

In an embodiment, wherein the lipopeptide compound itself is soluble in aqueous solution.

In embodiments, the lipopeptide compound is caspofungin, pneumocandin, aculeacin A, surfactin, iturin A, fengycin, lichenysin, daptomycin, viscosin, amphomycin, tsushimycin, friulimicin B, polymyxin, octapeptin, polypeptin, fusaricidin, tridecaptin, kurstakin, amphisin, lokisin, hodersin, tensin, massetolide, viscosinamide, pseudodesmin, pseudophomin, amphisin, syringomycin, syringopeptin, tolaasin, putisolvin, orfamide, syringafactin, entolysin, cichofactins, maribasins, ecomycin, pseudomycins, and/or cormycin A, or a pharmaceutically or biologically acceptable salt thereof. In an embodiment, the lipopeptide compound is caspofungin or a pharmaceutically or biologically acceptable salt thereof, such as caspofungin acetate.

In a further aspect, the present disclosure includes a method of delivering a hydrophobic agent to a cell, the method comprising contacting a composition or formulation described herein (comprising a lipopeptide compound (e.g., caspofungin and/or pharmaceutically or biologically acceptable salt thereof), a hydrophobic agent and an aqueous solution) with the cell. In an embodiment, the method further comprises solubilizing the hydrophobic agent with the lipopeptide compound (e.g., caspofungin or and/or pharmaceutically or biologically acceptable salt thereof) to provide the composition or formulation. In another embodiment, the method comprises forming a suspension of micelles composed of the lipopeptide compound (e.g., caspofungin or and/or pharmaceutically or biologically acceptable salt thereof) and the hydrophobic agent to provide the composition or formulation. In further aspects, the present disclosure also relates to a composition or formulation described herein for use in delivering a hydrophobic agent to a cell, as well as to a use of a composition or formulation described herein for delivering a hydrophobic agent to a cell, or to a use of a composition described herein for the preparation of a formulation for delivering a hydrophobic agent to a cell. In an embodiment, the composition or formulation comprises the lipopeptide compound caspofungin and/or its salt thereof caspofungin acetate. In embodiments, the cell is in vitro or in vivo (and can be, for example, in a human or an animal subject). In embodiments, the hydrophobic agent is any hydrophobic agent described herein (e.g. ubiquinone or poorly soluble drugs) and or combinations thereof.

In a further aspect, the present disclosure includes a composition or formulation obtainable/obtained by a method described herein.

In a further aspect, the present disclosure relates to a method of treating or alleviating the symptoms of a disease in a subject in need thereof, that would benefit from the administration of a hydrophobic agent to the subject.

In an embodiment, the disease or a condition is a disease or condition that would benefit from an increase in intracellular ubiquinone levels, the method comprising administering a therapeutically effective amount of a composition or formulation described herein to the subject so as to treat or alleviate the symptoms of the disease or the condition in the subject. In such a case, the hydrophobic agent would be ubiquinone. In an embodiment, the subject is a human or an animal subject. In still another embodiment, the disease or the condition is associated with mitochondrial dysfunction. In yet a further embodiment, the method further comprises determining the presence of mitochondrial dysfunction in the subject prior to administering the formulation. In still another embodiment, the disease or the condition is a mitochondrial disease, Parkinson's disease, Huntington's disease, Alzheimer's disease, amyotrophic lateral sclerosis, diabetes (including type I and II), cardiac failure (including congestive heart failure), ischemic heart disease, hypertension, coronary artery disease, idiopathic dilated cardiomyopathy, pulmonary arterial hypertension, ataxia (including Friedreich's ataxia), bipolar depression, Duchenne muscular dystrophy, fibromyalgia, cancer, asthenozoospermia, periodontal disease, migraine, pre-eclampsia, Down's syndrome, aging and/or a ubiquinone deficiency. In an embodiment, the disease or condition is associated with a ubiquinone deficiency. In yet a further embodiment, the method further comprises determining the presence of ubiquinone deficiency in the subject prior to administering the formulation. In still another embodiment, the disease or condition is associated with primary ubiquinone deficiency and/or with a secondary ubiquinone deficiency.

In a further embodiment, the disease or condition is cancer, and the present disclosure relates to a method of treating cancer or reducing cancer cell proliferation in a subject in need thereof, the method comprising administering a therapeutically effective amount of a composition or formulation described herein to the subject, wherein the hydrophobic agent is a chemotherapeutic or anticancer agent. In embodiments, chemotherapeutic or anticancer agent is a taxane drug, such as paclitaxel, docetaxel, cabazitaxel, or any combination thereof. In embodiments, the cancer is leukemia, breast cancer, cervical cancer or prostate cancer. In these cases, the compounds and formulations of the present disclosure are intended to be used or administered to a subject in need of cancer treatment. A subject in need of such treatment may be a human or a non-human subject. An effective amount for treating cancer will be the amount necessary to inhibit, delay, or slow cancer cell proliferation. When administered to a subjective, effective amounts will depend, of course, on many factors, e.g., the particular condition being treated, individual patient parameters, concurrent treatment and the mode of administration. In embodiments, it is generally preferred that a maximum dose of the individual components or combinations thereof be used, that is, the highest safe dose approved.

In a further aspect, the present disclosure includes a method of identifying a compound for the treatment or the alleviation of symptoms of a condition associated with a ubiquinone deficiency in a subject in need thereof, the method comprising: a) providing a living cells lacking the ability to express a Mclk1 gene or a Mclk1 gene ortholog; b) combining the test agent with the Mclk1 knockout cell in a first respiration-dependent medium to provide a first cell culture and determining the ability of the Mclk1 knockout cell to survive in the first cell culture or the rate of respiration of the Mclk1 knockout cell; and c) characterizing the test agent as being useful in the treatment or the alleviation of symptoms of the condition associated with the ubiquinone deficiency if the test agent is determined to allow the survival of the Mclk1 knockout cell in the first cell culture or increase the respiration rate of the Mclk1 knockout cell. In an embodiment, the first respiration-dependent medium comprises 2,4-dihydroxybenzoic acid (2,4-DHB) in an amount insufficient to allow survival of the Mclk1 knockout cell in the absence of the test agent. In still another embodiment, the method further comprises d) providing a living cell lacking the ability to express (i) a Mclk1 gene or a Mclk1 gene ortholog and (ii) a Pdss2 gene or a Pdss2 gene ortholog; e) combining the test agent with the Pdss2/Mclk1 double knockout cell in a second respiration-dependent medium to provide a second cell culture and determining the ability of the Pdss2/Mclk1 double knockout cell to survive in the first cell culture; and f) characterizing the test agent as being useful in the treatment or the alleviation of symptoms of the condition associated with the ubiquinone deficiency if the test agent is determined to allow the survival of the Pdss2/Mclk1 double knockout cell in the second cell culture. In a further embodiment, the second respiration-dependent medium comprises ubiquinone in an amount insufficient to allow survival of the Pdss2/Mclk1 double knockout cell in the absence of the test agent. In another embodiment, the method further comprises determining ubiquinone levels in the transgenic cell in the presence and absence of the test compound, optionally in combination with 2,4-DHB or ubiquinone. In yet another embodiment, the method further comprises g) combining the Pdss2/Mclk1 double knockout and/or the Mclk1 single knockout cell with a positive control agent in a third respiration-dependent medium to provide a third cell culture and determining the ability of the Pdss2/Mclk1 double knockout and/or the Mclk1 single knockout cell to survive in the third respiration-dependent medium; and h) characterizing the method as being useful for identifying agents for the treatment or the alleviations of symptoms of the condition associated with the ubiquinone deficiency in the subject if the presence of the positive control agent in the third respiration-dependent medium is determined to allow the survival of the Pdss2/Mclk1 double knockout and/or the Mclk1 single knockout cell. In another embodiment, the positive control agent is ubiquinone in an amount sufficient to allow survival of the Pdss2/Mclk1 double knockout and/or the Mclk1 single knockout cell in the absence of the test agent. In a further embodiment, the method further comprises i) combining the Pdss2/Mclk1 double knockout and/or the Mclk1 single knockout cell with a negative control agent in a fourth respiration-dependent medium to provide a fourth cell culture and determining the ability of the Pdss2/Mclk1 double knockout and/or the Mclk1 single knockout cell to survive in the fourth respiration-dependent medium; and j) characterizing the method as being useful for identifying agents for the treatment or the alleviations of symptoms of the condition associated with the ubiquinone deficiency in the subject if the presence of the negative control agent in the fourth respiration-dependent medium is determined to fail to allow the survival of the Pdss2/Mclk1 double knockout and/or the Mclk1 single knockout cell. In yet another embodiment, the negative control agent is dimethylsulfoxide (DMSO). In a further embodiment, the respiration-dependent medium lacks glucose and can comprise, for example, a single carbohydrate source (e.g., galactose). In a further embodiment, survival is determined using a fluorescent or colorimetric assay. In yet another embodiment, the Pdss2/Mclk1 double knockout and/or the Mclk1 single knockout cell are mammalian cells or murine cells. In still a further embodiment, the Pdss2/Mclk1 double knockout and/or the Mclk1 single knockout cell are located in an animal and the method for comprises administering the test agent to the animal. Murine and human Mclk1/COQ7 and Pdss2 nucleotide and polypeptide sequences are shown in the attached sequence listing, with reference to Table 5.

In certain embodiments of the present disclosure, the hydrophobic compound is ubiquinone. In those cases, the present disclosure provides a method of treating or alleviating the symptoms of a condition associated with ubiquinone deficiency in a subject in need thereof or of treating other conditions that would benefit from ubiquinone supplementation. The method comprises mixing caspofungin and/or a salt thereof or its structural analogs with ubiquinone in an aqueous solution, and administering a therapeutically effective amount of the resulting solution to a subject in need thereof so as to treat or alleviate the symptoms of a condition associated with ubiquinone deficiency or to mitigate other conditions that would benefit from ubiquinone supplementation (e.g., mitochondrial dysfunction caused by mitochondrial DNA mutation). In an embodiment, the compound is caspofungin and/or a salt thereof. In yet another embodiment, the condition is associated with primary or secondary ubiquinone deficiency. In yet another embodiment, the condition is not directly related to ubiquinone deficiency but is believed to benefit from increased ubiquinone levels. In still a further embodiment, the method comprises, prior to administering, determining that the subject is afflicted with ubiquinone deficiency or a pathological condition that can be alleviated by ubiquinone supplementation.

The present disclosure is further directed to novel compositions or formulations useful for delivery of bioavailable hydrophobic drugs to cells and organisms. In embodiments, the novel compositions formulations comprise caspofungin or its structural analogs or salts thereof, a hydrophobic agent, and a pharmaceutically acceptable vehicle. In one embodiment, the formulation is micellar. In an particular embodiment, the hydrophobic drug is ubiquinone. This disclosure also provides a method for delivering hydrophobic drugs to cells by exposing cells to the micelle-based compositions or formulations described herein. In one embodiment, a method of exposing cells to hydrophobic drugs is provided, said method comprising culturing said cells in the presence of the formulations of this disclosure thereby facilitating delivery of said hydrophobic compounds to cells. The disclosure further provides a method of delivering hydrophobic compounds to cells in vivo comprising administering to an animal or human the micelle-based compositions or formulations of this disclosure. It is to be understood that the compositions or formulations used for the delivery of hydrophobic compounds to cells in vitro or in vivo may be freshly prepared by admixture or may be prepared earlier or stored prior to their use.

According to a yet other aspect, the present disclosure provides a method of identifying a compound for the treatment or the alleviation of symptoms of a condition associated with a ubiquinone deficiency in a subject in need thereof. Broadly, the method comprises a) providing a genetically-modified single knock-out (SKO) cell lacking the ability to express a Mclk1 gene or a Mclk1 gene ortholog; b) combining the test agent with the genetically-modified SKO cell in a first respiration-dependent medium to provide a first cell culture and determining the ability of the SKO cell to survive in the first cell culture; and c) characterizing the test agent as being useful in the treatment or the alleviation of symptoms of the condition associated with the ubiquinone deficiency if the test agent is determined to allow the survival of the genetically-modified SKO cell in the first cell culture. In an embodiment, a second respiration-dependent medium comprises 2,4-dihydroxybenzoic acid (2,4-DHB) in an amount insufficient to allow survival the SKO cell in the absence of the test agent to provide second cell culture. The test agent is characterized as being useful in the treatment or the alleviation of symptoms of the condition associated with the ubiquinone deficiency if the test agent is determined to allow the survival of the genetically-modified SKO cell in the second cell culture. In another embodiment, the method further comprises d) providing a genetically-modified double knock-out (DKO) cell (i) lacking the ability to express a Mclk1 gene or a Mclk1 gene ortholog and (ii) lacking the ability to express a Pdss2 gene or a Pdss2 gene ortholog; e) combining the test agent with the genetically-modified DKO cell in a third respiration-dependent medium added with a small amount of ubiquinone which in itself insufficient to allow survival of the DKO cells to provide a third cell culture and determining the ability of the DKO cell to survive in the third cell culture; and f) characterizing the test agent as being useful in the treatment or the alleviation of symptoms of the condition associated with the ubiquinone deficiency if the test agent is determined to allow the survival of the genetically-modified DKO cell in the third cell culture. In still another embodiment, the method comprises a) providing the genetically-modified Mclk1 SKO cells; b) combining the test agent with the genetically-modified SKO cell in a fourth respiration-dependent medium to provide a fourth cell culture and determining the respiration rate of the SKO cells by seahorse XF analyser; and c) characterizing the test agent as being useful in the treatment or the alleviation of symptoms of the condition associated with the ubiquinone deficiency if the test agent is determined to increase the respiration rate of the genetically-modified SKO cell in the fourth cell culture. In a further embodiment, the method further comprises determining ubiquinone levels in the genetically-modified cell in the presence and absence of the test compound, optionally in combination with ubiquinone or 2,4-DHB. In still a further embodiment, the respiration-dependent medium lacks glucose. In still a further embodiment, the respiration-dependent medium comprises a single carbohydrate source and the single carbohydrate source is galactose. In still a further embodiment, survival is determined using a fluorescent or colorimetric assay. In an embodiment, the DKO cell and/or the SKO cell are mammalian cells, such as, for example, murine cells. In another embodiment, the DKO cell and/or the SKO cell are located in an animal and the method comprises administering the test agent to the animal.

According to a further aspect, the present disclosure provides a genetically-modified or transgenic cell lacking the ability to express (i) a Mclk1 gene or a Mclk1 gene ortholog and (ii) a Pdss2gene or a Pdss2gene ortholog, such as a double knock-out (DKO) cell.

According to another aspect, the present disclosure provides a genetically-modified or transgenic animal bearing the genetically-modified Mclk1 SKO or Mclk1/Pdss2 DKO cell described herein.

In further embodiments, the present disclosure relates to genetically-modified or transgenic animals and cells. A "genetically-modified" or "transgenic" animal refers to an animal, such as a non-human animal in which one or more of the cells of the animal contain heterologous nucleic acid introduced by way of human intervention, such as by transgenic techniques well known in the art. Transgenic animals and cells in which the presence of the functional gene is controlled or conditional are also contemplated, such as the CRE recombinase constructs described herein. Transgenic cells are also considered to be recombinant cells, i.e. which contain a recombinant construct or modification as a result of human intervention/genetic manipulation. "Non-human animals" include mammals, vertebrates such as rodents, non-human primates, sheep, dog, cow, birds, amphibians, reptiles, etc. In embodiments, the non-human animal is a rodent, such as a mouse or rat, most preferably a mouse. A "transgene" refers to a nucleic acid sequence which is partly or entirely heterologous to the transgenic animal or cell into which it is introduced, or, is homologous to an endogenous gene of the transgenic animal or cell but is designed to be inserted, or is inserted, into the genome in such a way as to alter the genome of the cell into which it is inserted (e.g., its insertion results in a knockout).

Compounds and Methods Thereof for Increasing Aqueous Solubility of Hydrophobic Agents and Hence their, Bioavailability The present disclosure affords compounds and methods for increasing aqueous solubility of hydrophobic agents (including drugs) and hence their bioavailability. As used herein, a hydrophobic agent refers to a compound that is poorly soluble in water. It is meant that for all practical purposes, the solubility of the compound in water is insufficient to make the compound practicably usable without some modification either to increase its solubility or dispersibility in water, so as to increase the compound's bioavailability or avoid the use of excessively large volumes of solvent. In an embodiment, a compound that is poorly soluble in water is a compound having a solubility of less than about 30 mg/ml, in further embodiments equal to or less than about 20, 10, 5, 1, 0.5 or 0.1 mg/mL in water at ambient temperature. As used in the context of the present disclosure, the term "aqueous" refers to a composition in which water is the dissolving medium or solvent in the largest concentration by volume. When a substance is dissolved in a liquid, the mixture is termed a solution. The "aqueous solution" means any water-based liquid composition. In an embodiment, the aqueous solution is a physiologically compatible solution, such as, for example, a physiological saline.

Examples of poorly soluble compounds that may be comprised in the compositions or formulations described herein include the following hydrophobic drugs (solubility in water indicated in parenthesis):

Chemotherapeutic drugs: SN-38 (0.29 mg/mL), etoposide (200 µg/ml), docetaxel (4.93 µg/ml), campothecin (<50 µg/ml), cisplatin (0.25 µg/ml), temsirolimus (20 µg/ml), teniposide (0.0598 mg/ml)

Other anticancer drugs: VEGFR inhibitors (e.g. Cabozantinib, Nintedanib)(<1 mg/mL), Wnt/β-catenin modulators (e.g. XAV-939, ICG-001), Hedgehog inhibitors (e.g. SANT75, HPI1), PI3K/Akt/mTOR modulators (e.g. rapamycin, Buparlisib), 17-AAG (0.1 mg/mL), Repurposed drugs: curcumin (0.011 µg/ml), luteolin (5.72 µg/ml), retinoic acid (<1 mg/ml)

CNS drugs: dihydroergotamine (0.229 mg/ml); lorazepam (80 µg/ml), propanidid (0.229 mg/ml), diazepam (0.05 mg/ml), nimodipine (0.012 mg/ml), Carbamazepine (17.7 mg/L)

Diabetes medicine: glipizide (37.2 mg/l)

Gastrointestinal medications: omeprazole (0.359 mg/ml), tarazepide

Infection treatments: griseofulvin (8.64 mg/l), acyclovir (<2.5 mg/ml), albendazole (insoluble), azithromycin, itraconazole, fluconazole (1 mg/L)

Anti-inflammatory: flufenamic acid (9.09 mg/L), aceclofenac (insoluble), diflunisal (14.5 mg/L)

Others: fenofibrate (0.25 mg/ml), budesonide (10.7 mg/l), clofazimine (0.225 mg/l), spironolactone (22 mg/l), melarsoprol (0.804 mg/ml), nifedipine, cyclosporin, piroxicam (23 mg/L), finasteride (11.7 mg/L)

In an embodiment, the hydrophobic agent is ubiquinone.

In embodiments, the hydrophobic agent is a chemotherapeutic or anticancer drug, in a further embodiment a taxane drug. In embodiments, the hydrophobic agent is paclitaxel, docetaxel, cabazitaxel, or any combination thereof (which are taxanes).

In embodiments, the hydrophobic agent is ubiquinone, SN-38, etoposide, paclitaxel, docetaxel, cabazitaxel, campothecin, cisplatin, temsirolimus, teniposide, Cabozantinib, Nintedanib, XAV-939, ICG-001, SANT75, HPI1, rapamycin, Buparlisib, curcumin, luteolin, retinoic acid, dihydroergotamine, lorazepam, propanidid, diazepam, nimodipine, carbamazepine, glipizide, omeprazole, tarazepide, griseofulvin, acyclovir, albendazole, azithromycin, itraconazole, fluconazole, flufenamic acid, aceclofenac, diflunisal, fenofibrate, budesonide, clofazimine, spironolactone, melarsoprol, nifedipine, cyclosporin, piroxicam, finasteride, or any combination thereof.

Figure 12A:
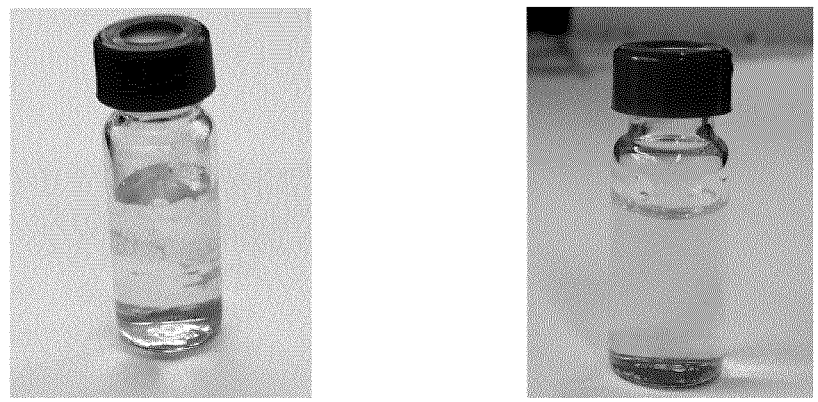
FIG. 12 illustrates an exemplary method of making water soluble $UQ_{10}$ using McC1. Said method comprises the steps of adding $UQ_{10}$ and McC1 into water, sonicating the mixture for 2 min at 4° C., and attaining solubilized $UQ_{10}$ by filtering off undissolved matters using a 0.22 µm nylon membrane syringe filter. (A) Photographs depicting the insolubility of $UQ_{10}$ in water (left) or solubilized $UQ_{10}$ made by the said method (right). (B) A bar chart demonstrating that mixing $UQ_{10}$ and McC1 by sonication results in much higher solubility of $UQ_{10}$. Results are shown as $UQ_{10}$ solubilized (measured as mM) by 5 mM of McC1. Values are mean±SEM (n=3). $p<0.01$; **$p<0.0001$ vs. water control; #$p<0.001$ (one-way ANOVA plus Tukey's post test).
Figure 12B:
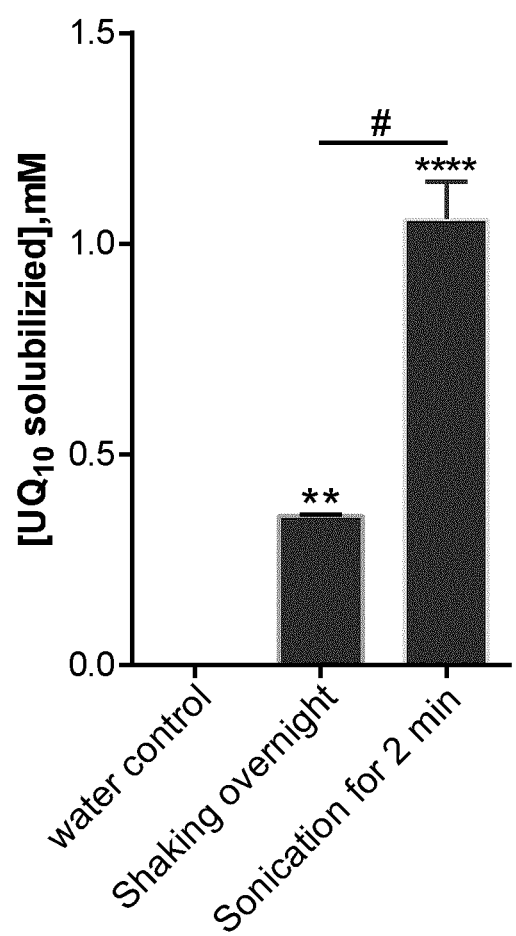

In particular, the utility of a lipopeptide compound (e.g., caspofungin and/or a pharmaceutically or biologically acceptable salt thereof) as a solubilizing agent to improve aqueous solubility of hydrophobic agents and their bioavailability is revealed in the present disclosure. Caspofungin (also referred to as McC1 in the present disclosure) is a semisynthetic lipopeptide that has been licensed for the treatment of invasive fungal infections. The present disclosure reports for the first time its use as a drug delivery vehicle to increase the bioavailability of hydrophobic agents. More specifically, the present disclosure shows that caspofungin/McC1 solubilizes hydrophobic compounds in an aqueous solution. This is specifically demonstrated with $UQ_{10}$ as shown in Example III. The aqueous solubility of $UQ_{10}$ on its own is ~0.7 ng/ml (811 pmol). The $UQ_{10}$ solubility was increased almost to ~1 mM by using 5 mM of caspofungin/McC1 which corresponds to more than 1,200,000-fold increase in aqueous solubility (FIG. 12B). In Example VII, it was further shown that two other hydrophobic compounds, curcumin and Sudan I, can also be effectively solubilized by McC1. Chemotherapy drug paclitaxel is also known for its poor water solubility. Shown in Example VIII, the water solubility of paclitaxel can be greatly increased by addition of McC1.

Formulations for Delivering Hydrophobic Agents

Hydrophobic agents have the potential of exhibiting therapeutic activity if they can be delivered across the cytoplasmic membrane and inside the cell to interact with their respective therapeutic target. The present disclosure provides a formulation for increasing the cellular uptake (also referred to as the delivery) of hydrophobic agents. Advantageously, the compositions or formulations of the present disclosure increase the delivery inside a cell, and in some embodiments, inside a mitochondria of hydrophobic agents, when compared to the delivery of those agents in the absence of a lipopeptide or surfactant.

In embodiments, a "surfactant" refers to compounds that lower the surface tension (or interfacial tension) between the aqueous solution and the solution comprising the hydrophobic agent. In some embodiments, an "aqueous solution" refers to a water-based solution that is biologically suitable for contacting a cell. In an embodiment, the aqueous solution is a physiologically compatible solution, such as, for example, a physiological saline.

In an embodiment, the composition or formulation disclosed herein comprises a lipopeptide compound and/or a pharmaceutically or biologically acceptable salt thereof (e.g., caspofungin and/or a pharmaceutically or biologically acceptable salt thereof), a hydrophobic agent and an aqueous solution. Advantageously, the presence of lipopeptide compound and/or pharmaceutically or biologically acceptable salt thereof in the formulation increases aqueous solubility of hydrophobic agents and enhances the delivery of the said hydrophobic agents inside a cell, when compared to the delivery of those agents in the absence of the lipopeptide compound and/or pharmaceutically or biologically acceptable salt thereof.

As such, references herein to solubilizing/solubilizes, increasing/increases solubility, increasing/increases aqueous solubility, improving/improves solubility, improving/improves aqueous solubility refer to increasing or improving the solubility of a hydrophobic agent in water as a result of using a lipopeptide compound and/or a pharmaceutically or biologically acceptable salt thereof (e.g., caspofungin and/or a pharmaceutically or biologically acceptable salt thereof) or a surfactant as described herein, such that the solubility of the hydrophobic agent in water is improved or increased when mixed with the lipopeptide compound and/or a pharmaceutically or biologically acceptable salt thereof (e.g., caspofungin and/or a pharmaceutically or biologically acceptable salt thereof) or surfactant relative to the solubility of the hydrophobic agent in water in the absence of the lipopeptide compound and/or a pharmaceutically or biologically acceptable salt thereof (e.g., caspofungin and/or a pharmaceutically or biologically acceptable salt thereof) or surfactant. In embodiments, such improved or increased solubility of the hydrophobic agent in water is an increase in solubility of at least about 10-fold, 25-fold, 50-fold, 75-fold, 100-fold, 250-fold, 500-fold, 750-fold or 1000-fold in the presence of the lipopeptide compound and/or a pharmaceutically or biologically acceptable salt thereof (e.g., caspofungin and/or a pharmaceutically or biologically acceptable salt thereof) or surfactant relative to in the absence of the lipopeptide compound and/or a pharmaceutically or biologically acceptable salt thereof (e.g., caspofungin and/or a pharmaceutically or biologically acceptable salt thereof) or surfactant. In an embodiment, such improved or increased solubility of the hydrophobic agent in water means that the hydrophobic agent is present in the aqueous solution such that none or substantially none of the hydrophobic agent is visible (to the naked eye) in particulate or solid form.

In an embodiment, the present disclosure provides a simple mixture of a lipopeptide compound with a hydrophobic agent in an aqueous solution. The formulation can be made simply by a method comprising admixing a lipopeptide compound and/or a pharmaceutically or biologically acceptable salt thereof (e.g., caspofungin and/or a pharmaceutically or biologically acceptable salt thereof) with the hydrophobic agent. As it will be recognized by the person skilled in the art, the mixture can be made using various techniques or ratios between the lipopeptide compound and/or pharmaceutically or biologically acceptable salt thereof and the hydrophobic agent as long as the resulting formulation provides dissolution of the hydrophobic agent and an increase in the cellular uptake of the hydrophobic agent if the said agent is targeted to go inside the cell. In a preferred embodiment, the hydrophobic agent is ubiquinone. In another embodiment, the hydrophobic agent is a poorly soluble drug as described herein.

In an embodiment, the present disclosure further provides a simple mixture of a surfactant with the hydrophobic agent in the aqueous solution. The formulation can be made simply a method comprising admixing the surfactant with the therapeutic agent. As it will be recognized by the person skilled in the art, the mixture can be made using various techniques or ratios between the surfactant and the hydrophobic agent as long as the resulting formulation provides an increase in the cellular uptake of the hydrophobic agent.

In still a further embodiment, the formulation is a micellar formulation, e.g., a suspension of micelles formed by mixing the lipopeptide compound and/or pharmaceutically or biologically acceptable salt thereof and a hydrophobic agent. The term "micelle" refers to any water soluble aggregates which are spontaneously formed from amphiphilic compounds (with both hydrophilic and hydrophobic moieties). The micelles of the formulations of the present disclosure encapsulate and/or entrap the poorly soluble compound within their hydrophobic cores. In one embodiment, the poorly soluble compound is ubiquinone. In another embodiment, the poorly soluble compound is a poorly soluble drug as described herein.

In an embodiment, the compositions or formulations described herein are substantially free of liposomes or bilayer containing structures. In a further embodiment, the compositions or formulations described herein are free of liposomes or bilayer containing structures.

In embodiments, the compositions or formulations described herein are substantially free of alcohol (e.g., ethanol) and/or oil or an oil-based compound or oil derivative (e.g. Cremophor EL™/Kolliphor EL™, which is a polyethoxylated castor oil, and are thus able to solubilize the hydrophobic agent without the addition of such agents. In further embodiments, the compositions or formulations described herein are free of alcohol (e.g., ethanol) and/or oil or an oil-based compound or oil derivative (e.g. Cremophor EL™/Kolliphor EL™, which is a polyethoxylated castor oil.

"Substantially free" as used herein with reference to a compound in a mixture means that it is intended that the compound, if present in a mixture, is present in very low or trace amounts, for example that the compound has not been intentionally added from a heterologous source or included in the mixture. In embodiments, a composition or formulation that is substantially free of a compound contains less than about 1.0%, 0.1%, or 0.01% (w/w) of the compound.

The formulations described herein can be administered to a subject in need thereof by any administration route including but not limited to: intravenous, intramuscular, intraperitoneal, subcutaneous, topical, intradermal, intranasal or transdermal delivery. In a preferred embodiment, the formulations are intended to be administered directly into the general circulation, for example, intravenously. This specific embodiment avoids the rapid metabolism or biotransformation by the gastrointestinal system or the liver prior to entering the bloodstream. It should be further noted that increasing aqueous solubility of poorly soluble drugs is also highly important for development of effective oral dosage forms. Therefore, the formulations of the present disclosure having enhanced solubility and bioavailability could be also useful for formulating into oral delivery forms such as tablets, capsules etc.

Figure 4:
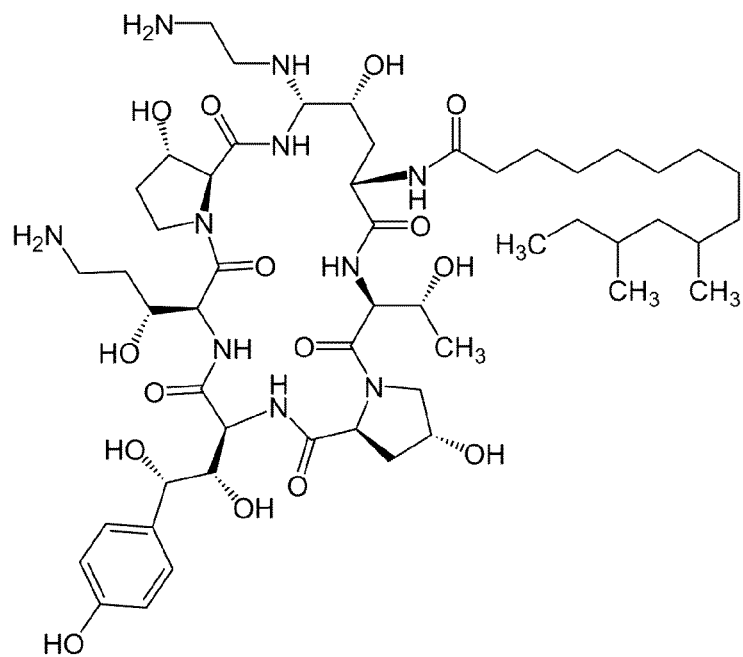
FIG. 4 presents the chemical structure of Caspofungin (also referred to as McC1 in the instant text and figures).

FIG. 4 shows the structure of caspofungin. It consists of a cyclic hexapeptide connected to a fatty acid side chain. In a preferred embodiment, the methods and formulations of the present disclosure use caspofungin or a salt thereof to solubilize hydrophobic compounds and improve their delivery and bioavailability. In another embodiment, the lipopeptide compounds described herein, including structural analogs of caspofungin, and/or salts thereof, can be used in the methods, compositions and formulations of the present disclosure. As used herein, a structural analog of caspofungin refers to a compound that is structurally similar to caspofungin whether or not the compound is functionally similar. In its broadest embodiment, structural analogs of caspofungin are lipopeptides that contain a peptide connected to a hydrophobic (e.g., lipid) moiety and exhibit amphiphilic properties.

Consideration for Selection of Structural Analogs of Caspofungin

Anidulafungin (AFG) and micafungin (MFG), which are structural analogs of McC1 sharing a similar cyclic peptide (see Table 1 for structural comparison), were tested for amphiphilic property and their ability to solubilize $UQ_{10}$.

TABLE 1

Structural comparison of caspofungin, anidulafungin (AFG) and micafungin (MFG)

| Compound name | Structure |
| --- | --- |
| Caspofungin/McC1 | 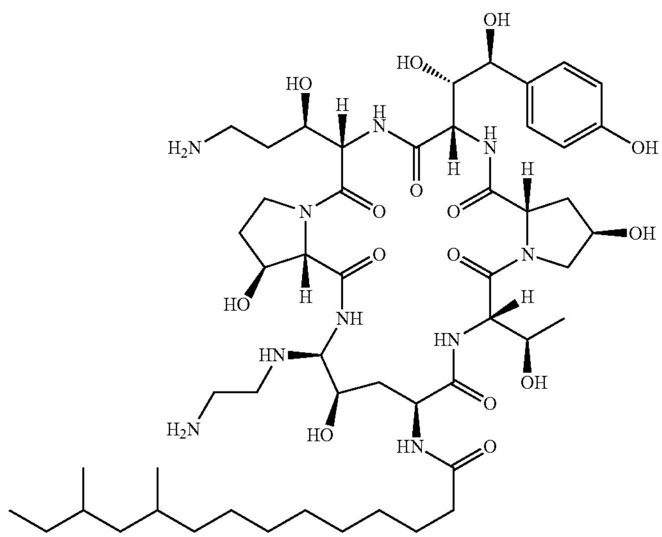 [SMILES: CCC(C)CC(C)CCCCCCCCC(=O)N[C@H]1C[C@@H](O)[C@@H](NCCN)NC(=O)[C@@H]2[C@@H](O)CCN2C(=O)[C@H]([C@H](O)CCN)NC(=O)[C@H]([C@H](O)[C@@H](O)c2ccc(O)cc2)NC(=O)[C@@H]2C[C@@H](O)CN2C(=O)[C@H]([C@@H](C)O)NC1=O] |
| Anidulafungin | 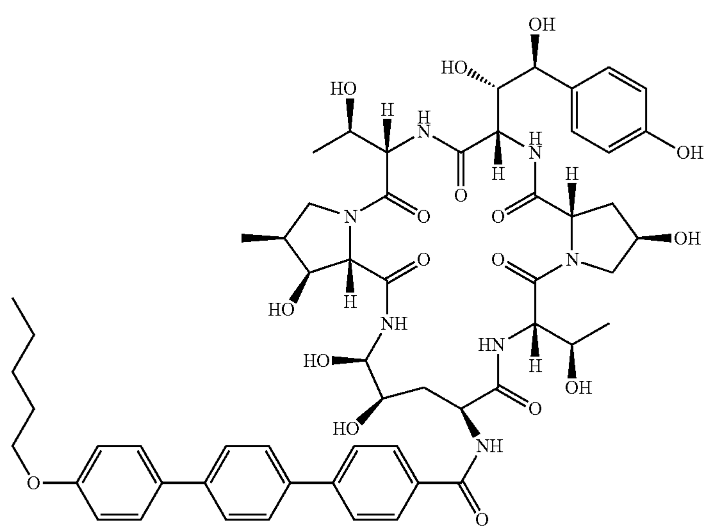 [SMILES: CCCCCOc1ccc(-c2ccc(-c3ccc(C(=O)N[C@H]4C[C@@H](O)[C@@H](O)NC(=O)[C@@H]5[C@@H](O)[C@@H](C)CN5C(=O)[C@H]([C@@H](C)O)NC(=O)[C@H]([C@H](O)[C@@H](O)c5ccc(O)cc5)NC(=O)[C@@H]5C[C@@H](O)CN5C(=O)[C@H]([C@@H](C)O)NC4=O)cc3)cc2)cc1] |

TABLE 1-continued

Structural comparison of caspofungin, anidulafungin (AFG) and micafungin (MFG)

| Compound name | Structure |
|---|---|
| Micafungin | (structure shown) |

Unlike McC1, MFG has a complex aromatic side-chain, and AFG has an alkoxytriphenyl side chain. As it can be seen in FIGS. 9 and 10, AFG and MFG show no stimulating effect on $UQ_{10}$ uptake and exhibit no detectable surfactant activity in a drop-collapse assay at the concentrations tested.

In contrast, the lipopeptide compounds surfactin (consisting of a cyclic heptapeptide linked to a β-hydroxyl fatty acid chain) and the lipopeptide detergent-12 (LPD-12; made of an α-helix forming peptide comprised of 25 amino acid and an alkyl chain attached to both ends of the helix via amide linkages) were shown herein to increase $UQ_{10}$ solubility.

Without wishing to be bound to any particular theory, it is believed that the presence of a fatty acid chain confers amphiphilic properties to caspofungin, and that its amphiphilic property is responsible for its ability to solubilize hydrophobic compounds and improve the delivery and bioavailability of hydrophobic compounds. This is further supported by the ability of surfactin, which also contain a fatty acid chain, to solubilize $UQ_{10}$ (Example IV). Surfactin has a cyclic peptide of 7 amino acids.

In embodiments, the lipopeptide compound is caspofungin, pneumocandin, aculeacin A, surfactin, iturin A, fengycin, lichenysin, daptomycin, viscosin, amphomycin, tsushimycin, friulimicin B, polymyxin, octapeptin, polypeptin, fusaricidin, tridecaptin, kurstakin, amphisin, lokisin, hodersin, tensin, massetolide, viscosinamide, pseudodesmin, pseudophomin, amphisin, syringomycin, syringopeptin, tolaasin, putisolvin, orfamide, syringafactin, entolysin, cichofactins, maribasins, ecomycin, pseudomycins, and/or cormycin A.

The lipopeptide compounds described herein can be made, without limitation, from the metabolism of a living organism (e.g., a biological compound), synthetically or both.

In embodiments, for use with a particular hydrophobic agent, the lipopeptide compound may be tested/selected to provide amphiphilic activity, efficient solubilization, sufficient stability and appropriate therapeutic benefit/side effect ratio. Amphiphilic activity can be measured by various methods known in the art, for example, by using the drop collapsing assay. Solubilization can be measured in various ways, like spectrophotometrically, HPLC, etc.

The compositions or formulations of the present disclosure are preferably "biocompatible" with the treated subjects (such as for example mammals, e.g., humans) as they exhibit low or tolerable toxicity when introduced in the treated subject.

The compositions or formulations of the present disclosure (including the micelles these compositions or formulations may comprise) can comprise a lipopeptide compound or salt thereof as the solubilizing agent. In a specific embodiment, the compositions or formulations, and in an embodiment the micelles of the compositions or formulations, comprise a lipopeptide compound or salt thereof as the sole solubilizing agent. In yet another embodiment, the compositions or formulations, and in still another embodiment the micelles of the formulation, comprise a caspofungin and/or a salt thereof as the sole solubilizing agent. In still another embodiment, the formulations, and in still another embodiment the micelles of the formulation, comprise a mixture of lipopeptide compounds or salts thereof as solubilizing agents. In these embodiments, the lipopeptide compounds can be, but are not necessarily limited to the lipopeptide compounds described herein.

The compositions or formulations of the present disclosure (including the micelles that these compositions or formulations may comprise) can include one or more hydrophobic agents. In an embodiment, the hydrophobic agent is hydrophobic or poorly soluble in water. In still another embodiment, the hydrophobic agent is insoluble in water. The hydrophobic agent can be a therapeutic agent, a cosmetic agent, a diagnostic agent and/or a research tool. The hydrophobic agent can be any type of hydrophobic compound, such as, without limitations, an organic or inorganic molecule, a peptide, a protein, a nucleotide, a nucleoside and/or a nucleic acid molecule. In an embodiment, the hydrophobic agent can have therapeutic and medicinal properties. In a further embodiment, the hydrophobic agent can be ubiquinone. In a still further embodiment, the hydrophobic agent can be a hydrophobic or poorly soluble drug described herein.

In a particular embodiment, the hydrophobic agent is $UQ_{10}$. $UQ_{10}$ has practically no solubility in water. It has previously been formulated as an oily suspension for oral use. Various approaches have been tried for enhancing its bioavailability, like solubility enhancement and use of novel drug carriers such as liposomes, microspheres, nanoparticles, nanoemulsions and self-emulsifying systems [6-12] (Table 2), but essentially without satisfying results.

TABLE 2

Examples of commercially available UQ formulations.

| Type of formulation | Tested formulation | Composition |
|---|---|---|
| Oily dispersion | Q-Gel (Tischon Corp.) | $UQ_{10}$ solubilized in an oil-based vehicle in a soft gel |
|  | CoQsol ® soft gel (Soft Gel Technologies, Inc. USA) | 30 mg $UQ_{10}$, 1295 IU Vitamin A (100% as β-carotene) and 30 IU vitamin E in rice bran oil, yellow beeswax, gelatin, glycerin, water and annatto extract |
|  | Nature Made ® CoQ10 soft gel capsules (Pharmavite ®, USA) | 30 mg $UQ_{10}$ and 1500 IU vitamin A (100% as β-carotene) in soybean oil, gelatin, glycerin and water |
|  | Bio-Quinone ®, (Pharma Nord, Denmark) | Containing 30 mg $UQ_{10}$ dissolved in soy oil in soft gelatine capsule |
|  | Myo-Quinone ®, (Pharma Nord) | Containing 100 mg $UQ_{10}$ dissolved in soy oil in soft gelatine capsule |
| Emulsion formulation | Nanoquinone (Sanomit, MSE Pharmazeutika GmbH) | Lipophilic emulsion of nanoparticular $UQ_{10}$ |
| Solubilizate formulation | Solu ™ Q10 soft gel capsule (AQUANOVA ® Germany) | 30 mg $UQ_{10}$ per soft gel capsule in medium-chain triglycerides and polysorbate 80 |
|  | Swanson Ultra ™ Q-Gel ® soft gel capsules (Tishcon Corp., USA) | 30 mg CoQ10 and 6 IU vitamin E in gelatin, purified water, glycerin, titanium dioxide, annatto seed extract, polysorbate 80, medium-chain triglycerides, sorbitol and sorbitan momooleate |
|  | CoQsource ® (SourceOne Global Partners) | 30 mg $UQ_{10}$ in a matrix of capric/caprylic acid triglyceride and Tween 80 |

In an embodiment, the hydrophobic agent is the chemotherapy drug Paclitaxel (PTX). Because of water insolubility, currently PTX is formulated with the use of polyoxyethylated castor oil (Cremophor EL™) to improve the drug solubility. However, Cremophor EL™ is known to cause serious side effects, such as hypersensitivity reactions. As a result, prolonged infusion time and pre-treatments are required. Moreover, data suggest that the presence of Cremophor EL could alter the pharmacokinetic profile of PTX in vivo.

In some embodiments of the present disclosure, a lipopeptide compound or a salt thereof is used to solubilize UQ and hence increase the delivery and bioavailability of UQ. In an embodiment, the composition or formulation of the present disclosure, comprising lipopeptide compound or a salt thereof and $UQ_{10}$, is used to delivery UQ into cells and animals. In these formulations, a concentration of 0.005 to 20 mM of caspofungin can be used to solubilize a concentration of 10 to 5000 µM of $UQ_{10}$. In an embodiment, the concentration of the lipopeptide compound or salt thereof in the composition or formulation is at least about 0.005, 0.05, 0.5, 1, 2, 3, 4, 5, 7.5, 10, 12.5, 15, 20, 30, 40 or 50 mM. In another embodiment, the concentration of the lipopeptide compound or salt thereof in the composition or formulation is at most about 50, 40, 30, 20, 15, 12.5, 10, 7.5, 5, 4, 3, 2, 1, 0.5 or 0.005 mM. In yet another embodiment, the concentration of caspofungin in the composition or formulation is between about 0.05, 0.5, 1, 2, 3, 4, 5, 7.5, 10, 12.5, 15, 20, 30 or 40 and about 40, 30, 20, 15, 12.5, 10, 7.5, 5, 4, 3, 2, 1, 0.5, 0.05 or 0.05 mM. In still another embodiment, the concentration of the lipopeptide compound or salt thereof in the composition or formulation is between about 5 and 50 mM. In another embodiment, the concentration of $UQ_{10}$ in the composition or formulation is at least about 2.5, 5, 7.5, 10, 12.5, 15, 17.5, 20, 22.5, 25, 100, 500, 1000 or 5000 µM. In another embodiment, the concentration of $UQ_{10}$ in the composition or formulation is at most about 5000, 1000, 500, 100, 25, 22.5, 20, 17.5, 15, 12.5, 10, 7.5, 5 or 2.5 µM. In still another embodiment, the concentration of $UQ_{10}$ in the composition or formulation is between about 2.5, 5, 7.5, 10, 12.5, 15, 17.5, 20, 22.5, 25, 100, 500, 1000 and about 5000, 1000, 500, 100, 25, 22.5, 20, 17.5, 15, 12.5, 10, 7.5 or 5 µM. In yet another embodiment, the concentration of $UQ_{10}$ in the composition or formulation is between about 2.5 and 25 µM.

The compositions or formulations of the present disclosure can include additional non-medicinal components such as, for example, a buffer, a saline, a further surfactant, a vitamin and/or an oil. The formulations can further comprise adjuvants, preservatives, and other compounds whose inclusion in light of storage and/or use of the composition or formulation may be beneficial. Adjuvant as used herein refers to any molecule that provides a beneficial function, such as, for example, modulating endocytosis to improve drug pharmacology.

The compositions or formulations of the present disclosure can be used to deliver a hydrophobic drug or drug combinations either in vitro or in vivo. They can also be used to deliver functional biomolecules such as enzymes, proteins, and nucleic acids to cells.

In some embodiments, the compositions or formulations of the present disclosure exhibit stability during storage. In the context of the present disclosure, "stability" refer to the ability of the formulation to maintain its physical and chemical property after a specific time in storage. For example, the compositions or formulations of the present disclosure comprising lipopeptide- (e.g. caspofungin-) solubilized form of $UQ_{10}$ remain stable for at least 1, 3, 5 or more weeks when stored at 4° C.

The micellar compositions or formulations of the present disclosure can be made by methods known in the art to make micelles, for example, direct dissolution and thin-film hydration method. In some embodiments of this disclosure, micelles are prepared by direct dissolution aided by vigorous shaking. In alternative or complementary embodiments, mixing of an amphiphile and hydrophobic compound is aided by sonicating. After the micelles have formed, the resulting mixture can be filtered (for example with a 0.22 µm filter) to remove large aggregates or insoluble particulate matter. The amount of hydrophobic agent in the filtered mixture can then be determined by various methods depending on the properties of the hydrophobic agent. The filtered mixture can be concentrated or diluted to achieve a specific concentration of the hydrophobic agent. The resulting mixture can be used directly or stored for future use.

The compositions or formulations of the present disclosure (including the micelles of that these compositions or formulations may comprise) can be administered for most routes, such as parenteral (e.g., intravenous, intraperitoneal, subcutaneous, intramuscular, intrasternal, and transepithelial), intranasal, oral, topical, pump and others. They can be prepared in water suitably mixed with suitable excipients. Under ordinary conditions of storage and use, these preparations may contain a preservative, for example, to extend shelf life or limit bacterial growth. The compositions or formulations of the present disclosure can be designed into pharmaceutically acceptable compositions for administration in vivo. Depending on the route of administration, the compositions or formulations of the present disclosure may be coated in a material to protect the components (such as the micelles) from the action of enzymes, acids, and other natural conditions that may inactivate certain properties of the composition. Their therapeutically effective dose can vary depending on many factors such as the pharmacodynamic properties of the therapeutic component in the formulation, the mode of administration, the weight and other characteristics of the recipient, the extent of the symptoms, and frequency of the treatment.

Compounds and Formulations for Ubiquinone Supplementation

In one specific aspect, the present disclosure provides compositions and formulations (such as, for example, micellar compositions and formulations) for treating or alleviating the symptoms associated with a condition which would benefit from UQ supplementation. For example, this condition can be associated with a mitochondrial dysfunction and/or a UQ deficiency. As used herein, the expression "treatment or alleviation of symptoms" refers to a composition's or formulation's ability to help limit and slow down development and progression of a condition and/or improve symptomology. Broadly, the expression "treatment or alleviation of symptoms associated with a condition characterized by UQ deficiency" encompasses an increase of tissue UQ levels, and, in some embodiments, procures a normal tissue UQ level which results in significant improvement of disease phenotypes. Signs and symptoms of UQ deficiency vary depending upon the particular defect and severity of loss of UQ content. Common symptoms associated with conditions associated with UQ deficiency include, but are not limited to, encephalomyopathy, severe infantile multisystemic disease, cerebellar ataxia, isolated myopathy and nephrotic syndrome (or nephropathy). Other conditions that would benefit from UQ supplementation include, but are not limited to, Parkinson's disease, Leigh's syndrome, mitochondrial disease syndrome as well as ageing.

In some embodiments the hydrophobic agent is UQ. In these cases, the compositions and formulations of the present disclosure are intended to be used or administered to a subject in need thereof, e.g., a subject suspected to be or afflicted by a ubiquinone deficiency. A subject in need thereof may be a human or a non-human subject. Ubiquinone deficiency encompasses both primary ubiquinone deficiency and secondary ubiquinone deficiency. As used herein, the term "primary ubiquinone deficiency" refers to a ubiquinone deficiency caused by one or more genetic defect(s) in the biosynthetic pathway of UQ. In humans, such genes include, but are not limited to ADCK3/CABC1, COQ2, COQ3, COQ4, COQ5 COQ6, COQ7, COQ9, PDSS1 and PDSS2. In mouse, such genes include, but are not limited to Pdss1, Pdss2, Coq2, Coq3, Coq4, Coq5, Coq6, Coq7/Mclk1, Coq8, and Coq9. As used herein, the term "secondary ubiquinone deficiency" refers to inadequate (e.g., decreased) levels of UQ that occur in the course of other diseases (e.g., Parkinson's diseases, mitochondrial DNA depletion syndrome, and cancer) or are caused by mutations in genes which are not involved directly in the biosynthesis of UQ. In humans, such genes include, but are not limited to MADD, BRAF, ETFDH, APTX, BRAF, or MFN2.

The present disclosure provides the use of a therapeutically/pharmaceutically effective amount of at least one (and in some embodiments more than one) compounds as well as associated formulations for the treatment or the alleviation of symptoms of a condition which would benefit from UQ supplementation. As used herein the expression "therapeutically effective amount" refers to an amount (dose) effective in mediating a therapeutic benefit to a subject in need thereof (for example treatment or alleviation of symptoms of a condition associated with ubiquinone deficiency). It is also to be understood herein that a "pharmaceutically effective amount" may be interpreted as an amount giving a desired therapeutic effect, either taken in one dose or in any dosage or route, taken alone or in combination with other therapeutic agents.

Compounds which has been identified by the screening methods described herein as being useful for the treatment or the alleviation of symptoms of a condition associated with UQ deficiency are: PI3K/Akt/mTOR inhibitors (such as, for example, OSI-027, WYE-125132 (WYE-132), AZD2014, PP242, CH5132799, BKM120 (NVP-BKM120, buparlisib), TG100713, AZ20, rapamycin (Sirolimus)), glucocorticoids (such as, for example, deflazacort, triamcinolone, fluocinolone acetonide, fluocinonide and/or flumethasone), corticosteroids (such as, for example, desonide, halcinonide, fluorometholone acetate, budesonide, betamethasone (Celestone), ioteprednol etabonate, betamethasone dipropionate (diprolene), betamethasone valerate (betnovate), hydrocortisone (cortisol), methylprednisolone, prednisolone (hydroretrocortine), mometasone furoate, fluticasone propionate, fluocinolone acetonide (flucort-N), prednisolone acetate (omnipred), fluocinonide (vanos), triamcinolone acetonide, dexamethasone, dexamethasone acetate and/or dichlorisone acetate), DNA-damaging agents (such as, for example, irinotecan), bacterial gyrase inhibitors (such as, for example, balofloxacin), proteasome inhibitors (such as, for example, MLN2238 and/or MLN9708), anti-inflammatory agents (such as, for example, tranilast (SB 252218), sulindac (Clinoril)), DPP-4 inhibitors (saxagliptin (BMS-477118, onglyza)), HIV integrase inhibitors (such as, for example, elvitegravir (GS-9137)), calcium channel inhibitor (such as, for example, felodipine (plendil)), IMPDH inhibitors (such as, for example, mycophenolic (mycophenolate)), beta-(1, 3)-glucan synthase inhibitors (such as, for example, caspofungin acetate), antibiotics (such as, for example, doxycycline HCl), topoisomerase inhibitors (such as, for example, SN-38) or Bcl2 inhibitors (such as, for example, ABT-199 (GDC-0199)). The compounds and formulations of the present disclosure can be administered alone or in combination with one or more additional therapeutic compound. In some embodiments, it may be necessary/useful to administer or use these compounds with UQ, and particularly $UQ_{10}$ (especially when administered to humans). UQ can be administered prior to, concomitantly or after the administration of the compounds of the present disclosure. In some embodiments, UQ is administered concomitantly with the compounds of the present disclosure. In an embodiment, the compounds of the present disclosure include capsofungin/McC1. Capsofungin has been shown to enhance cellular uptake of UQ when administrated at the same time as UQ. In yet another embodiment, UQ is administered with caspofungin and, in still another embodiment, UQ is administered concomitantly with caspofungin, such as, for example, in a micellar formulation.

The compounds described herein can be provided as pharmaceutically or biologically acceptable salts. This expression refers to conventional acid-addition salts or base-addition salts that retain the biological effectiveness and properties of the compounds described herein and suitable for use in contact with the tissues of human and animals without undue toxicity, irritation, allergic response and the like. They are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as e.g., tetramethylammonium hydroxide. The chemical modification of an agent into a salt is a well-known technique which is used in attempting to improve properties involving physical or chemical stability, e.g., hygroscopicity, flowability or solubility of compounds.

In a further aspect, this disclosure provides use of chemicals with amphiphilic properties other than caspofungin and its structural analogs to make solubilized in micelles comprising a hydrophobic agent, which may be used for treatment or alleviation of symptoms associated with a condition which would benefit from administration of a hydrophobic agent (e.g. UQ supplementation (e.g., UQ deficiency and mitochondrial diseases)). In an embodiment, the amphiphile is PLGA-PEG-PLGA type of block copolymers. Amphiphilic block copolymers are obtained by the polymerization of more than one type of monomer, typically one hydrophobic and one hydrophilic, so that the resulting molecule can self-assemble in solution to form micelles, vesicles or polymerosomes [13]. In another embodiment, the amphiphile is Tetradecyl trimethyl ammonium bromide (TTAB). In yet another embodiment, the amphiphile is Benzalkonium chloride (BAC) which has been used in pharmaceutical formulations (e.g., eyedrops) as an antimicrobial preservative. In still another embodiment, the amphiphile is natural surfactant saponins. Amphiphile micelles are known to solubilize hydrophobic compounds and thus can be utilized to improve drug delivery.

Administration of the compositions and formulations described herein can be made by any of the routes normally used for introducing a molecule into ultimate contact with blood or tissue cells: orally or parenterally, systemically or locally. For example, intravenous injection such as drip infusion, intramuscular injection, intraperitoneal injection, subcutaneous injection, intranasal delivery, suppositories, intestinal lavage, oral enteric coated tablets, and the like can be selected, and the method of administration may be chosen, as appropriate, depending on the nature of treatment conditions and the age and the conditions of the patient. The dose is typically chosen from the range of from 0.001 mg to 1000 mg per kg of body weight per administration. Alternatively, the dosage in the range of 1 to 1000 mg, preferably 5 to 50 mg per patient may be chosen. The effective dosage will vary depending on the chemical stability and pharmacodynamic properties of the compound, the type of formulation, the administration regime, the intended effect thereof, and the age, health and weight of the subject to be treated. These factors are well known to those of ordinary skill in the art and can be addressed with no more than routine experimentation.

The compositions and formulations described herein can be used or administered in any suitable manner, preferably in the form of a pharmaceutical composition with the pharmaceutically acceptable carriers or excipients. The terms "pharmaceutically acceptable carrier", "excipients" and "adjuvant" and "physiologically acceptable vehicle" and the like are to be understood as referring to an acceptable carrier, vehicle or adjuvant that may be administered to a patient, together with a compound or formulation described in this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. Depending on the route of administration, the formulations of the present disclosure may be coated in a material to protect the components (such as the micelles) from the action of enzymes, acids, and other natural conditions that may inactivate certain properties of the compounds or formulations.

The compositions and formulations of the present disclosure can be used or administered to any subjects, including mammalian subjects such as human subjects.

To use the disclosed UQ formulations for treatment, in some instances, it may be beneficial to monitor plasma and/or tissue levels of UQ, prior to and/or after the administration of the compounds or formulations that are aimed at increasing the concentration of UQ. For example, the effect on UQ content can be determined in blood and muscle biopsy samples. Furthermore, in some instances, in particular in case of UQ deficiency and other mitochondrial disease patients, positive treatment effect can be identified by determining specific serum markers (such as for example, lactate and/or alanine), examining muscle histology, or by monitoring the response of specific disease phenotypes (such as cerebellar ataxia). It may be beneficial to determine the presence (or absence) of UQ deficiency prior to the administration of the compounds or formulations to ascertain whether or not the subject intended to be treated exhibits UQ deficiency, as UQ deficiency patients in general require large doses and long-term treatment.

Methods of Screening for Compounds Capable of Alleviating UQ Deficiency

The present disclosure provides methods, assays and kits for identifying compounds useful for mitigating UQ deficiency and most particularly for the treatment or the alleviation of symptoms of a condition associated with UQ deficiency.

The methods, assays and kits of the present disclosure can advantageously be designed to identify compounds capable of alleviating UQ deficiency by substituting for UQ (herein referred to as UQ substitutes, UQ analogs or UQ mimetics), improving the biological activity of residual UQ, or acting through respiration-independent mechanisms (e.g., by preventing some of the deleterious consequence of mitochondrial impairment or even preventing cell death directly). In this specific embodiment, genetically-modified cells incapable of making UQ or having low residual UQ levels (e.g., cells with partial loss-of-function mutations in UQ biosynthetic enzymes) that by itself is insufficient to support respiration-dependent growth are placed and cultured in a respiration-dependent medium. As used in the context of the present disclosure, genetically-modified cells are cells whose genome has been artificially altered to lower or inhibit the expression of at least one gene in the biosynthetic pathway of UQ. As used in the context of the present disclosure, the expression "respiration-dependent medium" refers to a cell culture medium which requires that the cultured cells use oxidative phosphorylation for energy production, because the medium lacks sufficient substrate for glycolysis (e.g., glucose). In some embodiments, the respiration-dependent medium contains, as the sole carbohydrate source, galactose. As it is known in the art, the respiration-dependent medium can comprise, without limitation, serum, vitamins, salts, anti-bacterial and/or anti-mycotic agents. In this embodiment, test agents allowing the survival of the genetically-modified UQ-deficient cells in the respiration-dependent medium and/or increasing the respiration rate of the genetically-modified UQ-deficient cells are identified as useful for alleviating UQ deficiency.

The methods, assays and kits of the present disclosure can advantageously be designed to identify compounds capable of potentiating the therapeutic effects of exogenous UQ and more particularly of enhancing the cellular uptake of exogenous UQ. As used in the context of the present disclosure "exogenous" refers to materials originating from outside of the organism or cell. As used herein, "exogenous UQ" refers to any UQ that is not endogenously produced but that is instead administered to the subject in need thereof. In this specific embodiment, genetically-modified cells being incapable of making UQ (e.g., Pdss2/Mclk1 DKO cells) are placed and cultured in a respiration-dependent medium (as described herein) supplemented with a small amount of UQ (which can be in various forms, including $UQ_9$ and/or $UQ_{10}$) which by itself does not allow the survival of the genetically-modified cells (at least in the absence of the test agent). As such, test agents allowing the survival of the genetically-modified UQ-deficient cells in the respiration-dependent medium only when the medium is supplemented with exogenous UQ are identified as capable of facilitating the uptake of exogenous UQ by the cells. In an embodiment, the "small" amount of UQ corresponds to a concentration, in the respiration-dependent medium, of 1 µM or lower.

The methods, assays and kits of the present disclosure can advantageously be designed to identify compounds capable of increasing residual UQ synthesis. In such embodiments, genetically-modified cells having no activity of MCLK1/COQ7 enzyme are placed and cultured in a respiration-dependent medium (as described herein) supplemented with 2,4-DHB, an unnatural bypass precursor of UQ biosynthesis. When present, 2,4-DHB is provided in an amount which in itself does not allow the survival of the cells lacking Mclk1/COQ7 activity (in the absence of the test agent). As such, test agents allowing the survival of the genetically-modified cells in the respiration-dependent medium in the presence of 2,4-DHB but not in its absence are capable of increasing UQ biosynthesis.

The methods, assays and kits of the present disclosure include genetically-modified cells (which can be, for example, mammalian cells, including murine and human cells). The genetically-modified cells of the present disclosure have at least one genetic modification in at least one of the genes encoding at least one of the enzymes of the UQ biosynthetic pathway. Such genetic modification is intended to reduce or abolish the biosynthesis of UQ. The genetic modification can be nucleotide substitution, insertion, or deletion that reduces or abolishes the enzymatic activity of at least one enzyme of the UQ synthetic pathway. In humans, the genes involved in the UQ biosynthetic pathway include (but probably not limited to) ADCK3/CABC1, COQ2, COQ3, COQ4, COQ5, COQ6, COQ7, COQ9, PDSS1 and PDSS2. In mouse, the genes involved in the UQ biosynthetic pathway include (but probably not limited to) Pdss1, Pdss2, Coq2, Coq3, Coq4, Coq5, Coq6, Coq7/Mclk1, Coq8, and Coq9 [14].

In an embodiment, the genetically-modified cells of the present disclosure include a genetic modification in the Mclk1 gene or a corresponding gene ortholog. Mclk1 gene orthologs include, but are not limited to, COQ7 (in *H. sapiens*), COQ7 (in *S. cerevisiae*), coq-7/clk1 (in *C. elegans*) and ubiF (in *E. coli*). In some embodiments, the genetic modification of the cells of the present disclosure is a complete deletion of the Mclk1 gene or the Mclk1 gene ortholog. In some additional embodiments, the genetically-modified cells are referred to as Mclk1 knock-out (KO) cells. The term "knock-out", as used in the context of this disclosure, refers to complete suppression of an endogenous gene. Gene knock-out can be constitutive (e.g., expression is suppressed in every cell and tissue for the life of the target organism) or conditional (e.g., capable of being suppressed, specifically at a given time point and/or location). In some embodiments, the genetically-modified cells of the present disclosure carry genetic modifications in the Mclk1 gene (or its ortholog) and not in other genes involved in the UQ biosynthetic pathway. In such embodiments, the genetically-modified cells are referred to as single knock-out (SKO) cell lacking functional MCLK1 enzyme or a MCLK1 ortholog.

In an embodiment, the genetically-modified cells of the present disclosure include a genetic modification in a Pdss2 gene or a corresponding gene ortholog. As known in the art, PDSS2 (or the polypeptide encoded by the Pdss2 gene ortholog) works in combination with PDSS1 (or a polypeptide encoded by the Pdss1 gene ortholog) to elongate the prenyl side chain of UQ. Pdss2 gene orthologs include, but are not limited to, PDSS2 (in *H. sapiens*), COQ1 (in *S. cerevisiae*), coq-1 (in *C. elegans*) and ispB (in *E. coli*). In this specific embodiment, the cells have a genetic modification in the Pdss2gene or a Pdss2gene ortholog which abolishes the expression of the Pdss2 gene or the Pdss2 gene ortholog, e.g., lacking functional PDSS2. In some embodiments, the genetically-modified cells are referred to as Pdss2 knock-out (KO) cells. The Pdss2 KO cells can be constitutive or conditional KO.

The genetically-modified cells of the present disclosure can have more than one genetic modifications, for example at least two (or more) distinct genetic modifications in the genes involved in the biosynthesis of UQ: a first genetic modification in the Mclk1 gene (or its gene ortholog) and a second genetic modification in the Pdss2 gene (or its gene ortholog). In some embodiments, besides the genetic modifications in the Mclk1 gene (or its gene ortholog) and the Pdss2 gene (or its gene ortholog), the genetically-modified cells of the present disclosure do not have additional modification in the genes associated with the UQ biosynthetic pathway. In some embodiments, the genetically-modified cells of the present disclosure are constitutive or conditional knock-out in both the Mclk1 gene (or its gene ortholog) and the Pdss2 gene (or its gene ortholog). In such embodiment, the genetically-modified cells are referred to as double knock-out (DKO) cells if they lack the ability to express both the Mclk1 gene (or its gene ortholog) and the Pdss2 gene (or its gene ortholog), e.g., they lack both functional MCLK1 and PDSS2.

The genetically-modified cells of the present disclosure can be, without limitations, eukaryotic or prokaryotic cells. When the genetically-modified cells are prokaryotic cells, they can be bacterial cells, such as, for example, from the genus *Escherichia* and, in some additional embodiments, from the species *Escherichia coli*. When the genetically-modified cells are eukaryotic cells they can be, without limitations, yeast cells (such as, for example, *Saccharomyces cerevisiae* cells), nematodes (such as, for example, *Caenorhabditis elegans* cells) or mammalian cells (such as murine or human cells). When the genetically-modified cells are of mammalian origin, they can be derived from various tissues and organs and can be, for example, embryonic fibroblasts. In an embodiment, the genetically-modified cells are fibroblasts of murine embryo origin and are referred to as mouse embryonic fibroblast (MEF) cells.

In the methods of the present disclosure a test agent is combined with the genetically-modified cells described herein. As used in the present disclosure, a "test agent" is any compound (including, but not limited to, small molecular weight molecules) that may be screened for its ability to rescue UQ deficiency or alleviate the symptoms associated with UQ deficiency. In an embodiment, the method comprises providing cells lacking UQ (cells lacking the ability to express (i) a Mclk1 gene or a Mclk1 gene ortholog and/or (ii) a Pdss2 gene or a Pdss2 gene ortholog), combining them with the test agent, culturing the resulting mixture in the respiration-dependent medium, and determining cell viability. As indicated above, the mutant cells are not capable of surviving in a respiration-dependent medium (in the absence of exogenous UQ). As such, test agents capable of rescuing the death of the genetically-modified cells described herein in a respiration-dependent medium are identified as candidate therapeutic compounds for the treatment or alleviation of symptoms associated with ubiquinone deficiency. In an different embodiment, the method also comprises providing genetically-modified Mclk1 SKO cells (e.g., lacking functional MCLK1 or its ortholog and having the ability to express a Pdss2 gene or a Pdss2gene ortholog), combining them with the test agent and culturing the resulting mixture in a respiration-dependent medium (supplemented with a minimal amount of 2,4-DHB) and determining cell viability. When added to the respiration-dependent medium, 2,4-DHB is provided in an amount that, on its own, has no effect on the survival of genetically-modified Mclk1 SKO cells. As indicated above, Mclk1 SKO cells are not capable of surviving in a respiration-dependent medium (in the absence of exogenous UQ or 2,4-DHB). As such, test agents capable of rescuing the death of Mclk1 SKO cells during cell culture (optionally in the presence or in the absence of a minimal amount of 2,4-DHB) are identified as candidate therapeutic compounds, useful for the treatment or the alleviation of symptoms of a condition associated with ubiquinone deficiency. In embodiments in which the test agents are capable of rescuing the death of Mclk1 SKO cells only in the presence of 2,4-DHB, they are identified as candidate therapeutic compounds useful for increasing endogenous UQ biosynthesis. In another different embodiment, the method further comprises providing genetically-modified Pdss2/Mclk1 DKO cells (e.g., lacking functional MCLK1 or its ortholog and lacking the ability to express a Pdss2 gene or a Pdss2 gene ortholog), combining them with the test agent and culturing the resulting mixture in a respiration-dependent medium (supplemented with a minimal amount of $UQ_{10}$) and determining cell viability. When added to the respiration-dependent medium, $UQ_{10}$ is provided in an amount that, on its own, has no effect on the survival of genetically-modified DKO cells. As indicated above, Pdss2/Mclk1 DKO cells are not capable of surviving in a respiration-dependent medium (in the absence of exogenous UQ). As such, if test agents are capable of rescuing the death of Pdss2/Mclk1 DKO cells under such condition (in the presence of a minimal amount of UQ), they are identified as candidate therapeutic compounds useful for increasing uptake of exogenous UQ.

In the embodiment where UQ (in the form of $UQ_9$ or $UQ_{10}$ for example) is added into the respiration-dependent medium intended to receive or already containing test agent, it is important that exogenous UQ be provided in an amount that, on its own, is insufficient to allow survival of genetically-modified cells being incapable of making UQ (e.g., Pdss2/Mclk1 DKO cells) (in the absence of the test agent) to determine if test agent is able to potentiate the activity of the exogenous UQ. In the embodiment where 2,4-DHB is added into the respiration-dependent medium intended to receive or already containing test agent, it is important that the unnatural precursor of UQ biosynthesis be provided in an amount insufficient to allow survival of the Mclk1 SKO cells (in the absence of the test agent) to determine if the test agent is able to increase the biosynthesis of UQ.

In the methods, assays and kits of the present disclosure, a positive control can be included. The role of the positive control is to validate the method/assay performed. The positive control can be a positive control agent capable of rescuing the death of the genetically-modified UQ-deficient cells in a respiration-dependent medium. The positive control agent must be provided in an amount sufficient to allow survival of the genetically-modified cells in the culture conditions used. In embodiments in which a positive control agent is used, the screening method is considered validated (useful) only if the positive control agent allows the survival of the genetically-modified cells in the respiration-dependent medium. In some embodiments, the positive control agent can be, for example, UQ, provided as either $UQ_9$, $UQ_{10}$, or a combination thereof. Both $UQ_9$ and $UQ_{10}$ can be used when the genetically-modified cells are cells of murine or human origin. In other embodiments, the positive control agent can be 2,4-DHB when Mclk1 SKO cells are used.

In the methods, assays and kits of the present disclosure, a negative control can be included. The role of the negative control is to validate the method/assay performed. The negative control can be a negative control agent that has no effect on the death of the genetically-modified UQ-deficient cells in a respiration-dependent medium. In embodiments in which a negative control agent is used, the screening method is considered validated (useful) only if the negative control agent does not allow the survival of the genetically-modified cells in the respiration-dependent medium. In some embodiments, the negative control agent can be any compound lacking the ability to substitute for UQ, to increase UQ cell/tissue uptake, and to boost UQ biosynthesis. In some embodiment, the negative control agent is a diluent used to dissolve the test agent. For example, the negative control agent can be dimethylsulfoxide (DMSO).

Determining cell survival (e.g., the ability of a cell to remain viable) of the genetically-modified cells in the respiration-dependent medium can be performed using various methods known to those in the art. Cell viability assays include, but are not limited to tetrazolium reduction assays (including the MTT assay), resazurin reduction assays, protease viability marker assays, crystal violet staining (or other suitable dyes) assays, ATP assays and real-time cell viability assays (e.g., Glo™ MT cell viability assay). In an embodiment, cell survival can be determined using a fluorescent/colorimetric assay in which a reagent changes its color when incubated with viable cells (e.g., able to survive in the respiration-dependent medium) or after exposure to dead cells (e.g., not able to survive in the respiration-dependent medium). Exemplary fluorescent/colorimetric assays include, but are not limited to the resazurin assay and the crystal violet staining assay. The fluorescent/colorimetric assays are useful in the methods described herein because they can easily be used in a high-throughput screening method. In another embodiment, the direct effect of an test agent on mitochondrial respiration is determined by detecting the presence and extent of cellular respiration. This can be done, for example, by determining the oxygen consumption rate (OCR) of the cultured genetically-modified cells in the presence of the test agent in combination with (or not) UQ or 2,4-DHB (when Mclk1 KO cells are used). While this assay is more cumbersome than the fluorescent/colorimetric assays, it is more sensitive and can detect more discrete increase in mitochondrial respiration.

The present disclosure contemplates kits for the practice of the methods described herein. The kits preferably comprise at least one of the genetically-modified cells described herein as well as instructions on how to perform the methods described herein. Optionally, the kit can also comprise, one or more components of the respiration-dependent medium, a positive control agent, a negative control agent, reagents for cell viability detection, etc.

The present disclosure provides the genetically-modified cells described herein. In some embodiments, the genetically-modified cells described herein are Pdss2/Mclk1 double knock-out (DKO) cells (as described herein) lacking the ability to express both the Mclk1 gene (or its gene ortholog) and the Pdss2 gene (or its gene ortholog). In some embodiments, besides the genetic modifications in both the Mclk1 gene (or its gene ortholog) and the Pdss2 gene (or its gene ortholog), the cells of the present disclosure do not have additional modification in the genes associated with the UQ biosynthetic pathway. In an embodiment, the DKO cells are embryonic cells, such as, for example, mouse embryonic fibroblast cells.

The present disclosure also provides genetically-modified animals bearing mutations in the UQ biosynthetic genes described herein. The genetically-modified animal bearing mutations in UQ biosynthetic pathway is preferably a mammal and is not a human. In an embodiment, the genetically-modified animal is a mouse. In an embodiment, the genetically-modified animal is not a constitutive knock-out but a conditional knock-out in which the Mclk1 gene (or its gene ortholog) and/or the Pdss2 gene (or its gene ortholog) are inactivated only in a particular tissue or organ and/or are only inactivated at a specific time point (for example at 2 months of age). The genetically-modified animals of the present disclosure can be used to test an agent for its in vivo efficacy to treat or alleviate the symptoms of the condition associated with UQ deficiency. In animals such as mouse, adult-onset global UQ deficiency impairs mitochondrial function, causes growth retardation, hair loss, elevated blood lactate levels, loss of fat mass, and a reduction in life expectancy [5]. In such test subjects, agents (alone or in combination with UQ) useful for treatment or the alleviation of symptoms associated with UQ deficiency would likely improve their health status (such as weight gain and growing back of coat hair) and prolong their survival time. In animals with a tissue-specific defect in UQ biosynthesis, agents (alone or in combination with UQ) useful for treatment or the alleviation of symptoms associated with UQ deficiency would likely improve the function of the specific affected tissue of the body.

Therefore, the present disclosure also provides a method for testing in vivo efficacy of drug candidates intended for the treatment or the alleviation of symptoms associated with UQ deficiency using the genetically-modified animal described herein. The method comprises administering the test agent to the animal (such as, for example, a mammal or even a rodent which includes, without limitation, a mouse), alone or in combination with UQ. The method also comprises determining at least one of the following parameters: tissue UQ levels, mitochondrial function and clinical outcome (weight gain, or muscle strength for example). Test agents capable of increasing tissue UQ levels, improving mitochondrial function and mitigating disease phenotypes (weight loss or shortened survival for example) are characterized as being useful for the treatment or the alleviation of symptoms associated with UQ deficiency.

The present invention will be more readily understood by referring to the following examples which are given to illustrate the invention rather than to limit its scope.

Example I—Generation and Characterization of UQ-Deficient Cells and Animal Models Generation of Pdss2/Mclk1 double KO (DKO) MEFS. Mice carrying a conditional allele of Mclk1 were crossbred with Pdss2$^{loxP/loxP}$ mice to generate Pdss2/Mclk1 doubly homozygous conditional knockout mice. The same in vitro Cre/loxP recombination system used for the generation of Mclk1 KO (Wang et al., 2013) was used to generate MEFs deleted for both Pdss2 and Mclk1 genes. Successful inactivation of the conditional (floxed) alleles of Mclk1 or Pdss2 was confirmed by PCR, RT-PCR analyses, and lack of UQ content.

Tissue culture and viability assays. All cells were maintained in DMEM high glucose medium (Wisent BioProducts, Cat No. 319-005-CL) supplemented with 10% FBS (Thermo Fisher Cat No 10438034) and 1% antibiotic-antimycotic solution (Wisent BioProducts, Cat No. 450-115-EL) at 37° C. in 5% $CO_2$. To score growth and viability in galactose, cells were first grown in high glucose DMEM medium to confluency and then switched to glucose-free DMEM media (Thermo Fisher Cat No 26400036) supplemented with 10 mM galactose (Sigma Cat No G5388), 1 mM sodium pyruvate (Thermo Fisher Cat No 11360070), 10% dialyzed FBS (Thermo Fisher Cat No 26400036) and 1% antibiotic-antimycotic solution. Cell viability was determined by resazurin (Sigma Cat No R7017) reduction assay or crystal violet staining following standard procedures.

Quantification of quinones. Quinone content was detected and quantified by HPLC as previously described [15]. Briefly, cell lysates in RIPA buffer (50 mM Tris-HCl pH 7.6, 150 mM NaCl, 1% NP-40, 1% sodium deoxycholate, 0.1% SDS) were mixed with an equal volume of hexane/ethanol for 10 min by vortexing. After centrifugation for 5 min at 8,000×g, the hexane layer was collected and evaporated in a vacuum centrifuge. The quinone residue was then dissolved in ethanol and stored at −20° C. until HPLC analysis. The HPLC analysis was performed on a reverse phase C18 column (25.0×0.46 cm, 5 μm, Highchrom) using UV detection at 275 nm (Beckman System Gold). The mobile phase was methanol/ethanol (70:30 v/v) and isocratic elution was used at a flow rate of 1.8 ml/min.

Measurement of oxygen consumption by Seahorse XF analyzer. Cells were seeded in XF v7 24-well plates (Seahorse Bioscience) at ~40,000 cells/well for 24 hr. Prior to the measurements, cell medium was replaced with Seahorse XF base medium supplemented with 5.5 mM glucose (Sigma Cat No G8769), 2 mM Glutamax (Thermo Fisher Cat No 35050061) and 1 mM sodium pyruvate and allowed to equilibrate for 1 hour at 37° C. Oxygen consumption was measured first under baseline condition, followed by subsequent addition of 1 μg/ml oligomycin (Sigma Cat No 04876), 0.8 μM FCCP (Sigma Cat No C2920) and a combination of 1 μM rotenone (Sigma Cat No R8875) and 5 μM antimycin A (Sigma Cat No A8674) to assess the basal and maximal mitochondrial respiration rates. Four baseline measurements were recorded before the consecutive addition of the above-mentioned compounds, and three response measurements were taken after the addition of each compound. Results were finally normalized to protein content determined using the Bradford reagent (Bio-Rad). For experiments that involved culturing cells in the presence of lipoprotein-deficient serum (LPDS), cells were grown in culture medium supplemented with LPDS (Sigma S5394) for 1 week before OCR was measured using a Seahorse XF-24 extracellular flux analyzer as described above.

Generation of UQ deficient mouse models. Mice that carry homozygous floxed Mclk1 and/or floxed Pdss2 alleles as well as an inducible CreER transgene of interest were generated by crossbreeding Mclk1 floxed or Mclk1/Pdss2 double floxed mice with the CreER transgenic mice of interest. To induce deletion of the floxed gene(s), the compound transgenic mice (e.g., CreER+; Mclk1$^{loxP/loxP}$ or CreER+; Pdss2$^{loxP/loxP}$; Mclk1$^{loxP/loxP}$) were given tamoxifen by intraperitoneal (IP) administration at ~6-8 weeks of age (see Table 3). PCR detection of the recombined (KO) alleles, analysis of mRNA expression by RT-PCR as well as western blot analysis were used to validate successful recombination resulting in loss of expression of the target genes.

TABLE 3

Cre-lox conditional KO mouse lines that target UQ biosynthetic genes

| Mouse line | Target organs/tissues | TM administration regime | Ref |
|---|---|---|---|
| Pdss2$^{loxP/loxP}$ Mclk1$^{loxP/loxP}$; CAG-CreER$^{T2}$+ | All tissues | 150 mg/kg of body weight every other day for a total of 8 treatments | (Hayashi and McMahon, 2002) |
| Mclk1$^{loxP/loxP}$; HSA-MCM+ | Skeletal muscle | 150 mg/kg of body weight once daily injection for 5 days | [16] |
| Mclk1$^{loxP/loxP}$; Myh6-MCM+ | Cardiac myocytes | 40 mg/kg of body weight once daily injection for 5 days | [17] |
| Mclk1$^{loxP/loxP}$; DAT-CreER$^{T2}$+ | Dopaminergic neurons | 1 mg/mouse 2 times per day for 5 days | [18] |

Results

Figure 1B:
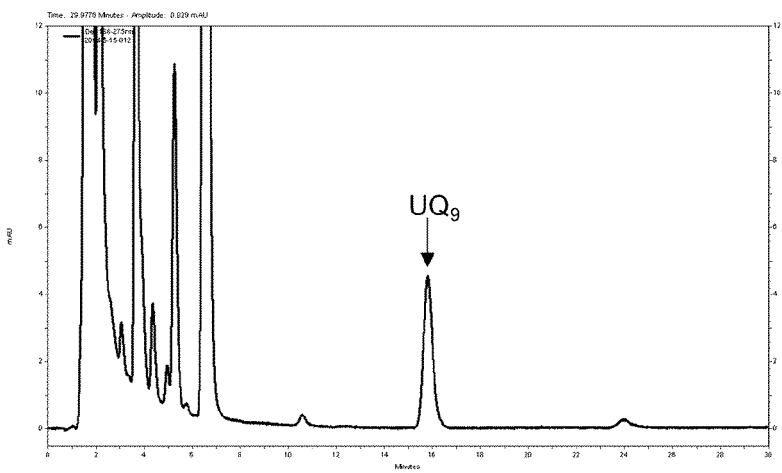
Figure 1B:
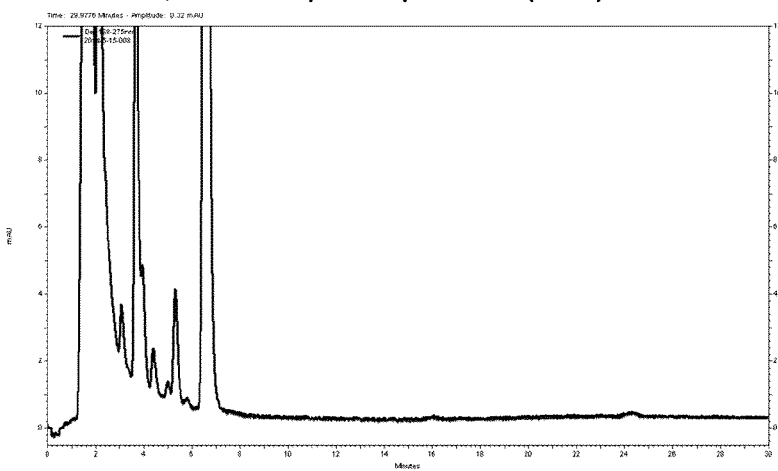

Pdss2/Mclk1 double knockout (DKO) MEFs. FIG. 1A shows that for both Mclk1 or Pdss2 genes, the recombined but not the floxed allele was detectable after infecting Pdss2/Mclk1 double floxed MEFs with Cre-expressing retrovirus. Moreover, RT-PCR analysis verified the absence of expression for both genes in these cells. These results confirmed that the conversion of floxed Mclk1 or Pdss2 alleles ("loxP") into the knockout (KO) form was complete (hereinafter referred to as DKO cells). In this context, the term "knockout" mean elimination of the function of the gene product. As anticipated, UQ$_9$, which is the primary isoform of UQ produced in the mouse, was not detectable in those cells, nor is the substrate of the MCLK1 enzyme, DMQ$_9$ (FIG. 1B).

Figure 2A:
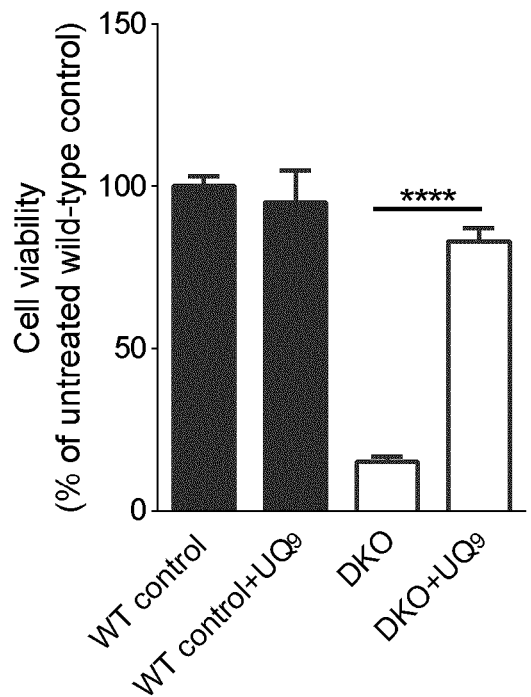
FIGS. 2A to 2D show that Pdss2/Mclk1 DKO cells have minimal respiratory activity and that the sustained respiration is due to trace amount of UQ$_{10}$ present in standard cell culture serum. (A) Histograms with relative cell viability data after 3 days' culture in glucose-free galactose-containing media. Wild-type (WT) control cells were viable after replacement of glucose with galactose in culture media, whereas Pdss2/Mclk1 DKO cells showed reduced viability which can be prevented with UQ$_9$ supplementation. Cell viability was measured by resazurin reduction assay. **$p<0.0001$ by one-way ANOVA with Tukey's multiple comparison test. (B) Cell images taken after 3 days' culture in glucose-free galactose-containing media. Results are shown for DKO cells cultured in a glucose medium (left panel), a glucose-free galactose-containing medium (middle panel) and a glucose-free galactose-containing medium supplemented with UQ$_{10}$ (right panel). (C) Measurements of oxygen consumption rate (OCR) by Seahorse XF24 Analyzer. The media used to culture the cells either contain fetal bovine serum (normal serum) or lipoprotein-deficient serum (LPDS). After a baseline OCR was established, the ATP synthase inhibitor oligomycin (oligo), the oxidative phosphorylation uncoupler carbonyl cyanide p-[trifluoromethoxy]-phenyl-hydrazone (FCCP) and a mixture of the complex I inhibitor rotenone (Rot) plus the complex III inhibitor antimycin A (AA) were injected sequentially into each well to derive mitochondrial respiratory parameters. Shown on the left are representative OCR traces. Quantitative data are graphed on the right as mean±SD (n=7). To calculate the basal respiration rate, the non-mitochondrial OCR value after Rot/AA injection was subtracted from the baseline OCR. The maximal respiratory capacity is the difference between FCCP- and Rot/AA-responsive OCR. $p<0.0001$ by two-way ANOVA with Tukey's multiple comparison test. LPDS: lipoprotein-deficient serum. The graphs illustrate that DKO cells are still capable of carrying out some mitochondrial respiration, but their rates of respirations are much lower than wildtype controls, and removal of lipoproteins from serum led to abolishment of respiration in DKO cells. (D) Exemplary data showing changes of oxygen consumption rates of DKO cells after treatment with UQ$_{10}$. A representative OCR trace is shown on the left. Quantitative data are graphed on the right as mean±SD (n≥3). $p<0.01$, ****$p<0.0001$ by two-way ANOVA with Sidak's multiple comparison test.
Figure 2B:
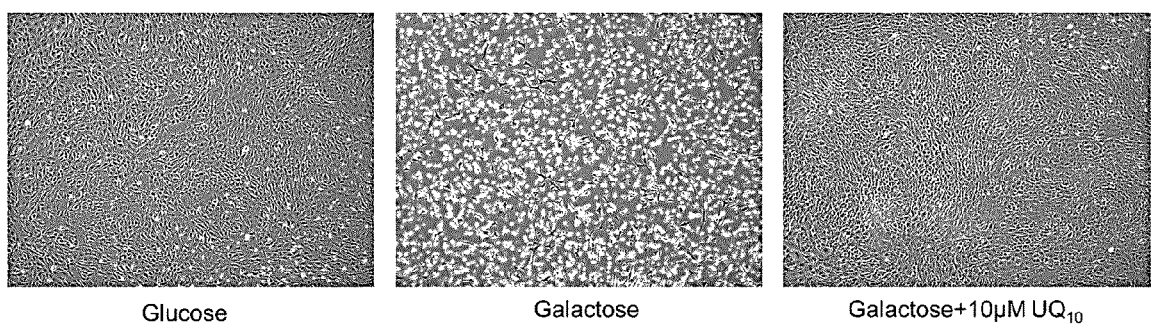
Figure 2C:
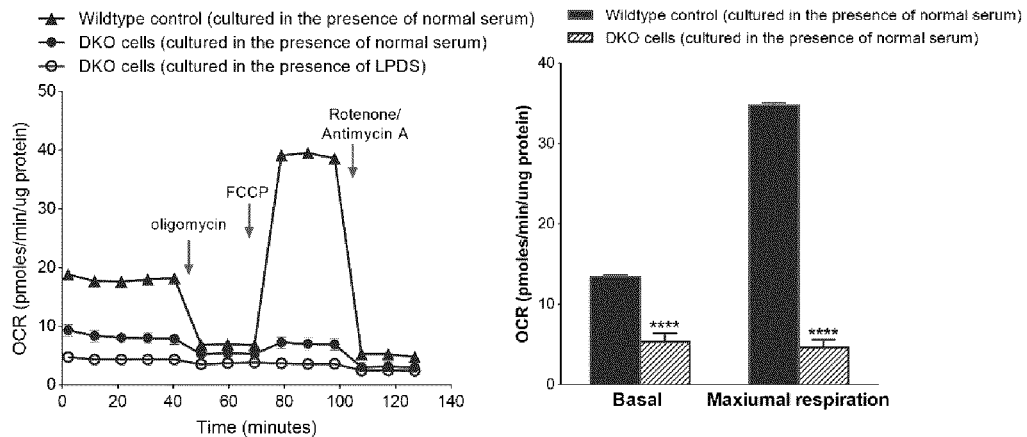
Figure 2D:
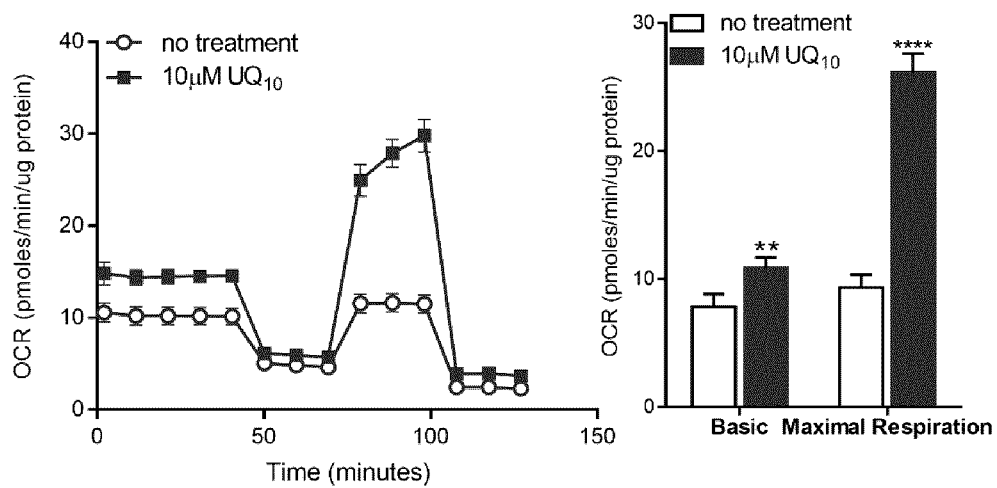

DKO cells were fully viable and exhibited no growth defects when cultured in the standard culture media. FIGS. 2A and 2B show that, without added exogenous UQ, DKO cells die after ~4 days' culture in galactose medium. UQ$_9$ or UQ$_{10}$ supplementation was sufficient to rescue them from galactose-induced cell death if provided at a sufficient amount, consistent with their primary defect being in the function of the respiratory chain due to lack of UQ. Despite lacking detectable UQ, they were still capable of carrying out some mitochondrial respiration, but their rates of respirations was much lower than wildtype controls (FIG. 2C). Without wishing to be bound to any particular theory, it is believed that the sustained respiration in Pdss2/Mclk1 DKO was due to the fact that cell culture serum contains trace amounts of UQ$_{10}$ which is primarily carried by lipoproteins. FIG. 2C illustrates that removal of lipoproteins from serum led to abolishment of respiration in DKO cells.

Example II—Methods of Screening for Drug Candidates for the Treatment of Ubiquinone Deficiency Four different screening methods were developed. The screening methods 1 to 3 are based on rescue-of-lethality in glucose-free galactose-containing media. The presence of galactose instead of glucose forces the cells to rely on oxidative phosphorylation for energy production. Screening method 4 is based on rescue of respiration, implying that processes immediately dependent on UQ have been rescued. Libraries of small molecules were screened for compounds and/or agents that increase survival of UQ-deficient cells (e.g., Mclk1 KO or DKO cells) in standard or modified galactose media depending on the screen settings.

Screening Scheme Galactose-Only Screen

The screen uses cells lacking UQ (e.g., Mclk1 KO cells) and consists of three key steps:
1) Day 0: preparation of Mclk1 KO cells in 96-well plates in standard (glucose-containing) culture medium.
2) Day 1: changing to glucose-free galactose-containing medium and adding compounds to be screened at a concentration of approximately 10 μM.
3) Day 4 to 6: following 3 to 5 days of incubation with the compound to be screened, media were removed and cell viability was assayed by resazurin reduction assay.

The resazurin cell viability assay. Briefly, resazurin was added directly to plates at 1/10 the volume of glucose culture medium. Viable cells with active metabolism can reduce resazurin into resorufin which causes a colour change from blue to pink. After a 2 hr incubation, plates were read on a plate reader (Tecan) to record absorbance at 570 nm and 600 nm. The cell viability was scored as a percentage relative to the signal from untreated glucose-grown wells. Consequently, each screened compound may be described by its effect (no, partial or full rescue) on survival of the KO cells in galactose medium.

Compounds that improve survival of Mclk1 KO cells in galactose were considered as positive screen hits. This galactose-only screening can yield not only hits that boost mitochondrial respiration but also molecules that act through respiration-independent mechanisms, e.g., by preventing some of the deleterious consequence of mitochondrial impairment or even preventing cell death directly. To distinguish between these two mechanisms of action, the primary hits obtained from Mclk1 KO cell screen were then screened for activity to enhance the survival of DKO cells in galactose or condition of low glucose (that decreases DKO cell viability). DKO cells have little mitochondrial respiratory activity. In order for them to survive in galactose, recovery of mitochondrial function is necessary as after replacement of glucose with galactose virtually no energy is made from glycolysis available to cellular functions. Therefore, those compounds that are also protective for DKO cells in no glucose conditions most likely can substitute functionally for UQ in the respiratory chain. On the other hand, for compounds that can rescue DKO cells in low glucose but not in galactose medium, they likely act by respiration-independent mechanisms, because, in low glucose medium some ATP still can be made (though too little of it to maintain cell viability) and under such conditions it might be possible to achieve cell survival by regulating other not-mitochondria related processes.

Screening Scheme 2. UQ Supplementation Screen

The screen also uses cells lacking UQ biosynthesis (e.g., DKO cells) and its protocol is essentially the same as the galactose-only screen except that in step 2, a minimal amount of $UQ_{10}$ is added into the galactose screening media at a concentration at which the added $UQ_{10}$ is insufficient by itself to support survival. The screen compound hits that are identified in this screen and that are ineffective on their own (when $UQ_{10}$ is not added into galactose medium) most likely can promote the absorption, or retention, or efficacy once absorbed, of exogenous UQ.

Screening Scheme 3. DHB Supplementation Screen

Figure 3A:
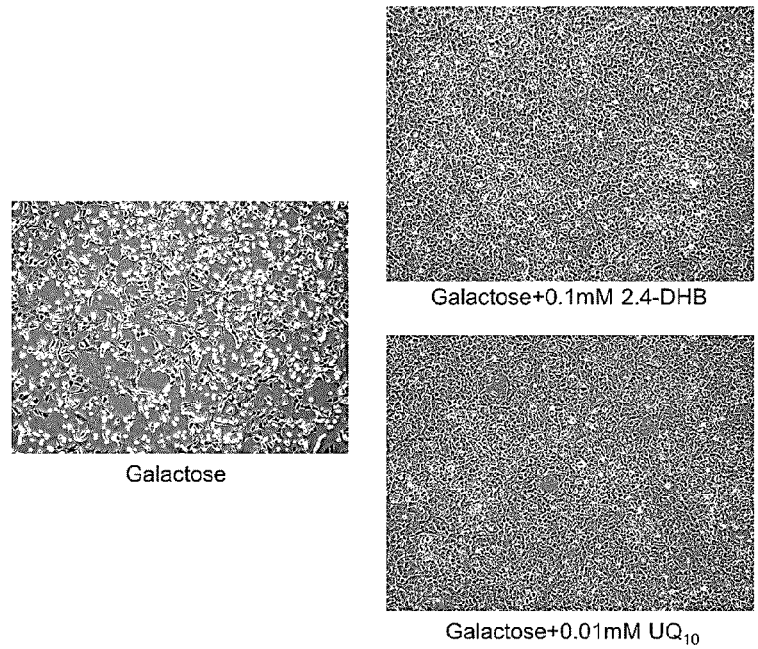
FIGS. 3A to 3C show the effect of 2,4-dihydroxybenzoic acid (2,4-DHB) or UQ$_{10}$ on Mclk1 KO cells. (A) Exemplary cell images of the rescue effect of 2,4-DHB or $UQ_{10}$ treatment on viability of Mclk1 KO cells in glucose-free galactose-containing medium. Results are shown for Mclk1 KO cells cultured in a glucose-free galactose medium (left panel), in a glucose-free galactose medium supplemented with 0.1 mM 2,4-DHB (upper right panel) or in a glucose-free galactose medium supplemented with 0.01 mM $UQ_{10}$ (lower right panel). (B) Exemplary data showing changes of oxygen consumption rates (OCR) of Mclk1 KO cells compared with wildtype control cells or after treatment with $UQ_{10}$. Typical OCR traces are shown (n=10). (C) Bar chart illustrating that $UQ_{10}$ supplementation improves the survival of Mclk1 KO cells in glucose-free galactose-containing medium (empty bars) in a dose-dependent manner. Data are expressed as mean±SEM (n=5-8). ****$p<0.0001$ (one-way ANOVA followed by Sidak's multiple comparisons test). Results are shown as cell viability quantified by percentage of resazurin reduction.

The screen uses Mclk1 SKO cells and its protocol is essentially the same as the galactose-only screen except that in step 2, the screening medium is added with 2,4-DHB at a concentration that allows the KO cells to restore some UQ biosynthetic ability but not sufficiently to allow for a level of UQ production that is sufficient for respiration-dependent growth. Thus, under these conditions a compound that can boost the overall level of UQ biosynthesis might allow the cells to make enough UQ to survive in a respiration-dependent medium. Such a screen can identify compounds that boost UQ biosynthesis at any level, including at the level of gene expression. FIG. 3A illustrates that treating Mclk1 KO cells with 2,4-DHB at a sufficiently high dose allows them to survive in galactose-containing media.

Figure 3B:
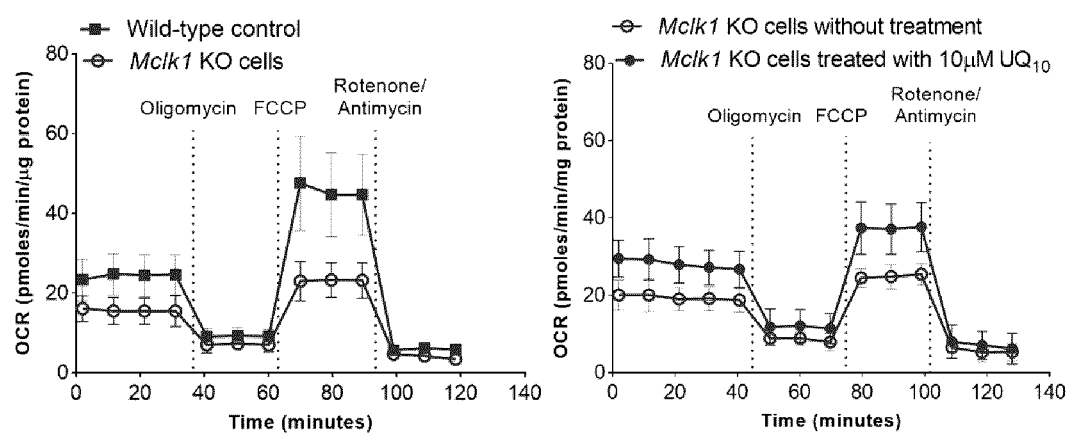

Screening Scheme 4; Screen of Respiration Modulator by Using Seahorse XF Instruments This screening approach aims to directly identify compounds that can boost mitochondrial respiratory chain activity in respiration-deficient cells. In this screen we use Mclk1 SKO cells in which mitochondrial respiration rate is low but not abolished (FIG. 3B). For this, cells were seeded into XF24 V7 culture plates and treated with testing compounds for 1 to 2 days before a treatment effect on cellular respiration is measured using the Seahorse XF-24e Flux Analyzer. The XF assay was the same as above described except galactose (10 mM) rather glucose was used as the sugar source to increase respiration rate and thus assay sensitivity. This screen allows us to identify compounds that augment mitochondrial respiration but not to a level that would have allowed detection in the screen based on survival rescue in galactose-containing respiration-dependent medium (scheme 1). In other words, it is capable of identifying compounds with potentially subtle mechanisms of action.

Figure 3C:
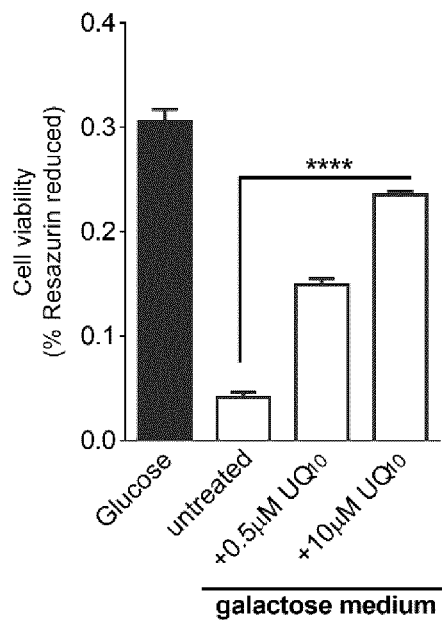

For methods 1, 2, and 4, $UQ_{10}$ supplementation at high concentrations was included to serve as a positive control. At sufficient doses, it produces reliable viability rescue of galactose-induced cell death and increases rates of mitochondrial respiration in UQ-deficient Mclk1 SKO and Pdss2/Mclk1 DKO cells (see FIG. 2D and FIG. 3A to C). FIG. 3C shows that supplementation of $UQ_{10}$ at a concentration of 0.5 µM had little effect, but that an almost full rescue was observed at 10 µM.

Caspofungin acetate (Cas number 179463-17-3) was one of the hits identified using the UQ supplementation screen method (method 2). Caspofungin acetate is an inhibitor of fungal 1,3-β-glucan synthesis. Its only medicinal use, that has been reported and approved, is as an antifungal antibiotic. In example III, its effect on UQ solubilization and uptake is illustrated.

Figure 5A:
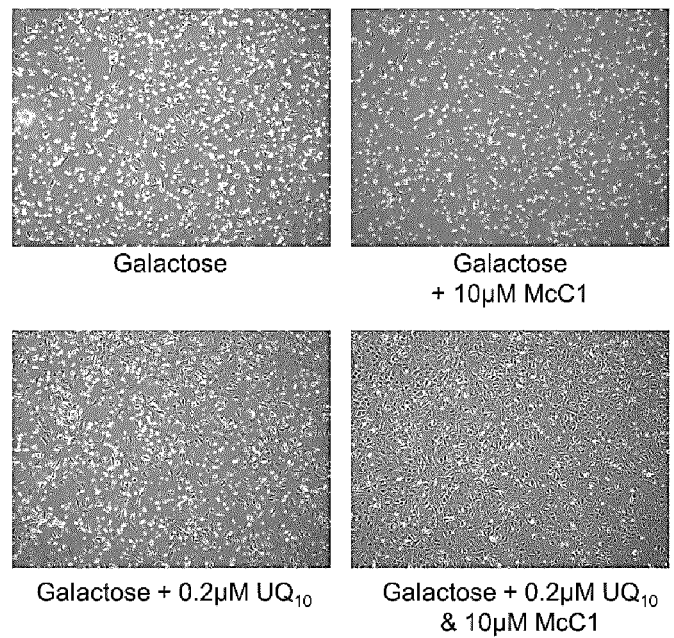
FIGS. 5A and 5B show that McC1 enhances the rescue effect of exogenous $UQ_{10}$ on mitochondrial dysfunction of Pdss2/Mclk1 DKO cells. (A) Exemplary cell images showing that McC1 by itself had no effect on galactose-induced lethality of DKO cells, but enhanced the rescue effect of exogenous $UQ_{10}$. Results are provided for DKO cells cultured in a glucose-free galactose-containing medium (upper left panel), in a glucose-free galactose medium supplemented with 10 µM of McC1 (upper right panel), in a glucose-free galactose-containing medium supplemented with 0.2 µM of $UQ_{10}$ (lower left panel) and in a glucose-free galactose-containing medium supplemented with 0.2 µM of $UQ_{10}$ and 10 µM of McC1 (lower right panel) (B) A column graph showing cell viability of DKO cells after 3 days' culture in a glucose-free galactose-containing medium treated with a low concentration of $UQ_{10}$ alone or in combination along with McC1. Error bars represent mean±SEM (n=6). ****$p<0.0001$ (one-way ANOVA, followed by Sidak's multiple comparisons test).
Figure 5B:
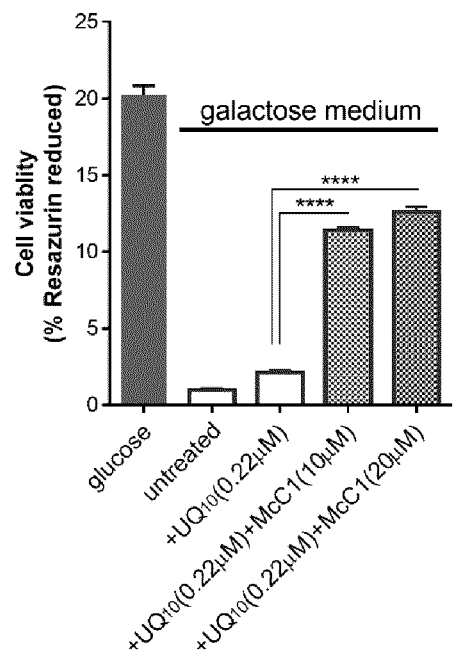

Example III—Evaluation of Properties of Caspofungin in Regards to Ubiquinone Solubilization In this present disclosure, caspofungin is sometimes referred to as McC1. FIG. 4 shows the chemical structure of McC1. As it can be seen in FIG. 5, McC1 by itself had no effect on survival of Pdss2/Mclk1 DKO cells in glucose-free galactose-containing medium. But, in the presence of a minimal amount of $UQ_{10}$ which on its own was not sufficient to support the survival of Pdss2/Mclk1 DKO cells, McC1 was able to rescue the mutant cells from death in the respiration-dependent medium. Different concentrations of McC1 were used (10 and 20 µM) and cell viability increased with increasing amount of McC1 in the media (FIG. 5B, last two bars).

Figure 6:
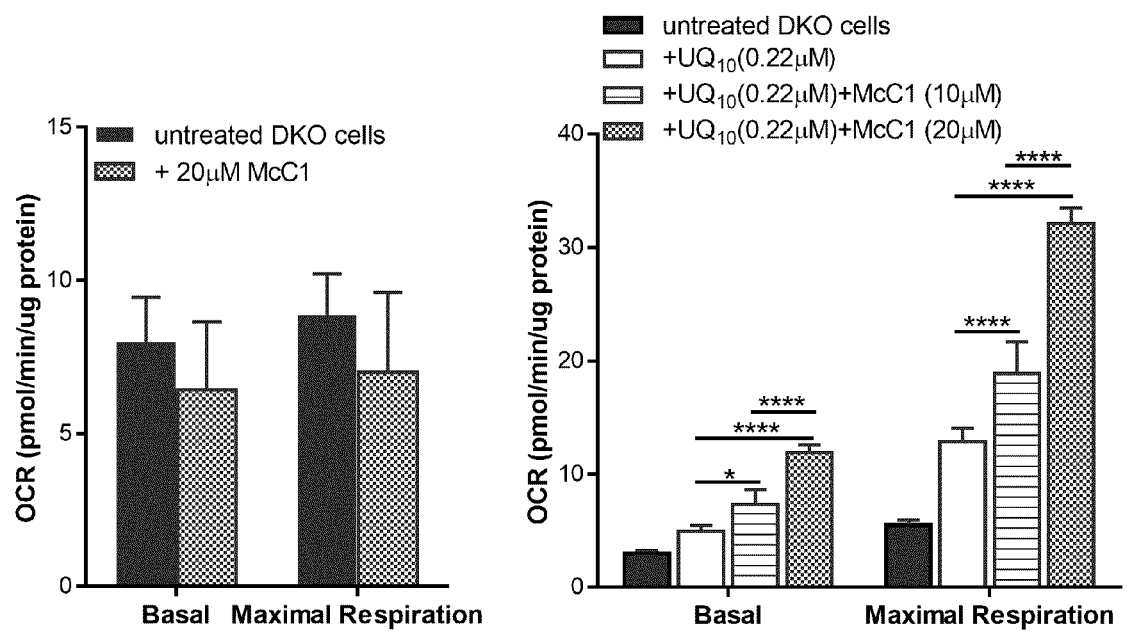
FIG. 6 provides the results of oxygen consumption rate (OCR) measurements carried out on Pdss2/Mclk1 DKO cells treated with McC1 (left panel) or a combination of McC1 and $UQ_{10}$ (right panel). Results are provided as OCR (pmol/min/µg of protein). Data are expressed as mean±SD (n=5). $p<0.05$, **$p<0.0001$ (two-way ANOVA, followed by Tukey's test).
Figure 7A:
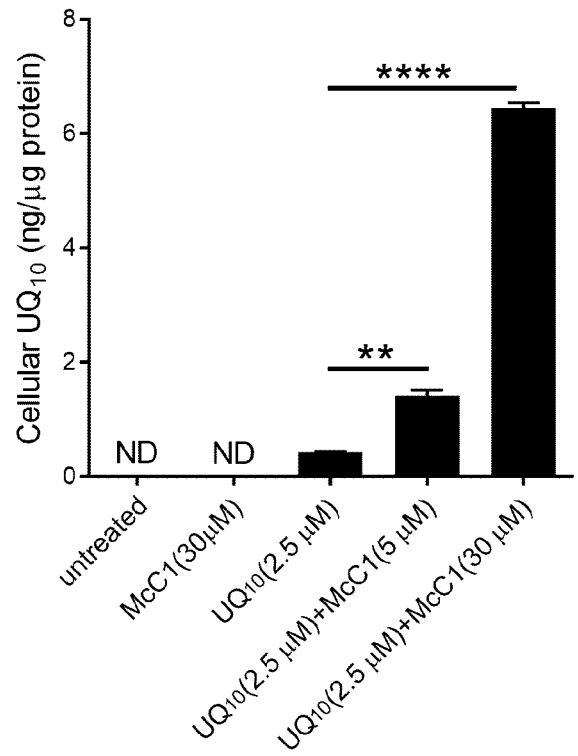
FIGS. 7A to 7D present exemplary data showing that McC1 is capable of increasing the uptake of exogenous UQ into cells and mitochondria. (A) Bar chart showing change of $UQ_{10}$ levels (as measured in ng/µg of protein) in Pdss2/Mclk1 DKO MEFs after treatment with $UQ_{10}$, McC1 alone, or $UQ_{10}$ and McC1 in combination. $p<0.01$, *$p<0.001$ (one-way ANOVA). (B) Bar charts presenting exemplary data showing changes of UQ levels in wildtype MEFs after treatment with $UQ_{10}$, McC1 alone, or both in combination. Results are shown as cellular $UQ_{10}$ levels (as provided in ng/µg of protein, left panel) or $UQ_9$ levels (as provided in ng/µg of protein, right panel) in untreated cells, after treatment with 12.5 µM of McC1, after treatment with 2.5 µM of $UQ_{10}$, or after co-treatment $UQ_{10}$ and McC1. Results are mean±SEM (n=3). **$p<0.0001$ (one-way ANOVA). (C) Bar chart presenting exemplary data showing changes of $UQ_{10}$ and $UQ_9$ levels in mitochondrial extracts from wildtype MEFs after treatment with $UQ_{10}$ alone, or in combination with McC1. Results are shown as $UQ_9$ and $UQ_{10}$ levels in ng/µg of protein. Results are mean±SEM (n=3). $p<0.0001$ (student's t-test). (D) Bar chart presenting exemplary data showing changes of $UQ_{10}$ level in mitochondrial extracts from Pdss2/Mclk1 DKO MEFs after treatment with $UQ_{10}$ alone, or in combination with McC1. Results are shown as $UQ_{10}$ levels (as provided in ng/µg of protein) in untreated DKO cells, after treatment with 2.5 µM of $UQ_{10}$, or after co-treatment 2.5 µM of $UQ_{10}$ and 12.5 µM of McC1. ND: Not Detectable. Results are mean±SEM (n=3). **$p<0.0001$ (one-way ANOVA).
Figure 7B:
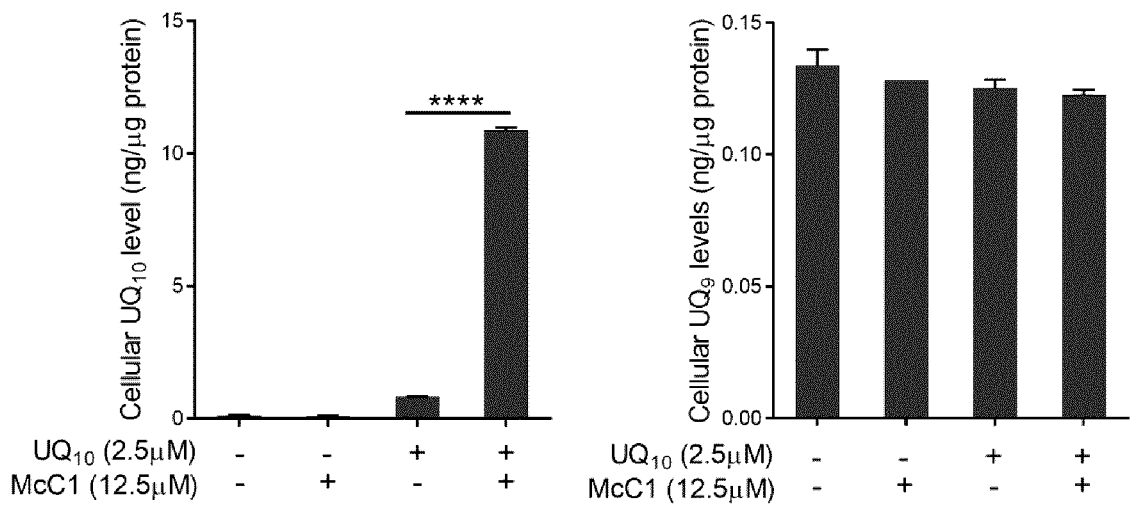
Figure 7C:
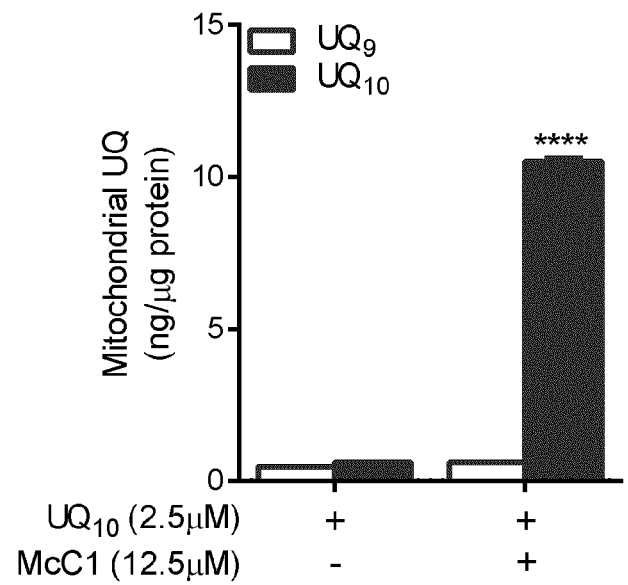
Figure 7D:
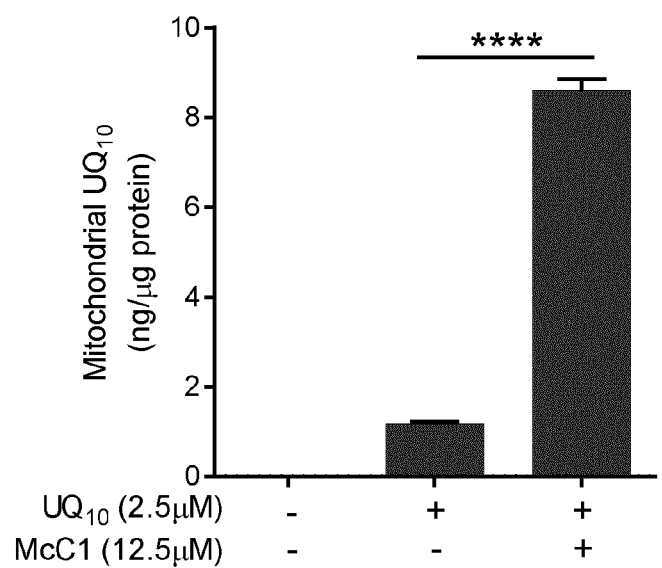

Quantitation of intracellular UQ levels confirms the enhancing effect of McC1 on cellular uptake of $UQ_{10}$. The results, presented in FIGS. 7A to 7D, show that, when used alone, McC1 had no effect on the intracellular concentration of UQ. However, in combination with $UQ_{10}$, McC1 increased uptake of exogenous $UQ_{10}$ into cells. These results are observed in both DKO (FIG. 7A) and wildtype MEFs (FIG. 7B). Uptake of exogenous $UQ_{10}$ had no effect on the level of $UQ_9$ which is the main species of endogenous UQ in mice (FIG. 7B). FIGS. 7C and 7D reveal that, both in Pdss2/Mclk1 DKO and wild-type MEFs, a dramatically higher level of $UQ_{10}$ was seen in the mitochondria fraction of cells treated with both McC1 and $UQ_{10}$ than that from cells treated with $UQ_{10}$ alone, showing that McC1 significantly increased uptake of exogenous $UQ_{10}$ into mitochondria. The higher level of mitochondrial UQ uptake in the presence of McC1 was further confirmed by whole-cell oxygen consumption measurement. Compared with $UQ_{10}$-treatment alone, co-treatment of $UQ_{10}$ and McC1 led to a greater increase of mitochondrial respiration in a dose-dependent manner (FIG. 6).

Figure 8:
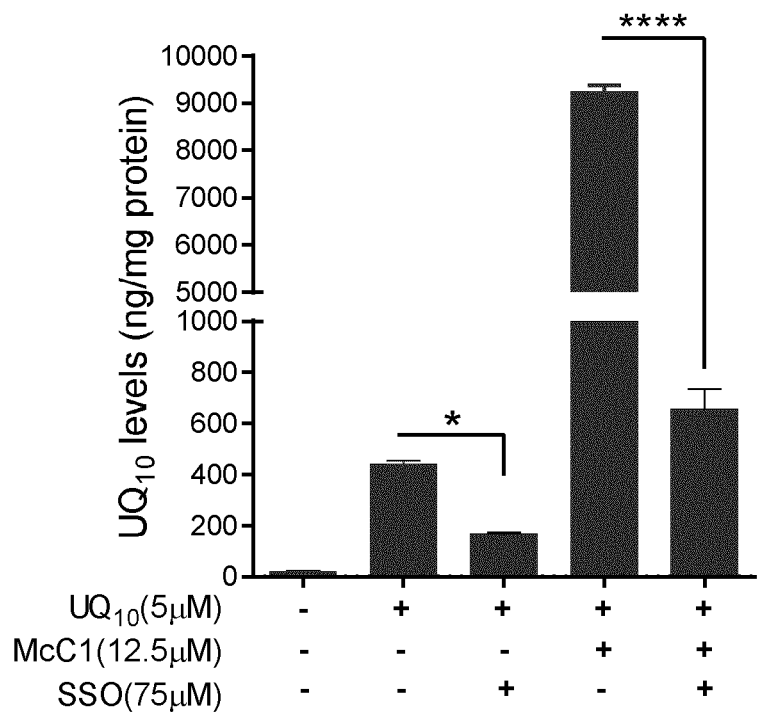
FIG. 8 presents exemplary data showing the inhibitory effect of sulfo-N-succinimidyl oleate (SSO) on cellular uptake of $UQ_{10}$. Results are shown as the levels of $UQ_{10}$ (measured as ng/mg of protein) of Pdss2/Mclk1 DKO MEFs cultured in the presence or absence of $UQ_{10}$, McC1 and/or SSO, as indicated below the bar graph. Error bars represent mean±SEM (n=3). *$p<0.05$; ****$p<0.0001$ (one-way ANOVA).

Sulfo-N-succinimidyl oleate (SSO) is a specific inhibitor of the scavenger receptor CD36. CD36 is a integral membrane protein that is widely expressed. SSO is known to covalently bind to CD36 via lysine 64 in the hydrophobic cavity thereby impairing CD36-mediated fatty acid uptake. In an attempt to understand the mechanism of action for McC1-facilitated UQ uptake, cellular $UQ_{10}$ levels were measured in wildtype MEFs after treatment with $UQ_{10}$ alone, combination of sulfo-N-succinimidyl oleate (SSO) and $UQ_{10}$, co-treatment with McC1 and $UQ_{10}$ in the presence or absence of SSO. As shown in FIG. 8, the addition of SSO inhibits cellular uptake of $UQ_{10}$. This was observed in both the cells treated with $UQ_{10}$ or $UQ_{10}$ combined with McC1. Thus, the results presented in this figure suggest that McC1's impact on $UQ_{10}$ uptake is dependent on the biological activity of CD36.

Drop collapse assay is a simple detection method of surface active agents. It relies on the capacity of surfactants to destabilize the liquid droplets on an oily surface. The drop-collapsing ability of McC1 along with other known potent surfactants was characterized. For each, 40 ul of compound solution in water was pipetted onto a hydrophobic Parafilm surface and the diameter of the drops was measured 1 min later using a ruler. The results shown on FIG. 11 indicate that McC1 exhibited a moderate surfactant activity, but it is less potent than Triton X-100.

Figure 11:
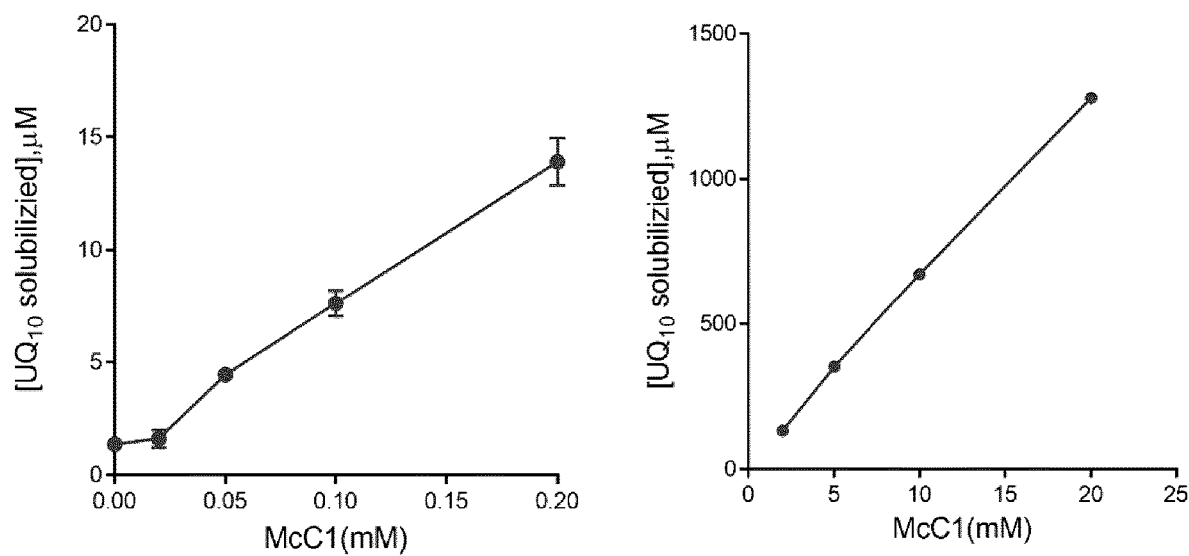
FIG. 11 provides exemplary data showing McC1 increases the water solubility of $UQ_{10}$ in a dose-dependent manner. Shown is a plot of $UQ_{10}$ solubilized (measured as µM) as a function of McC1 concentration (in mM, up to 25 mM). The same amount of $UQ_{10}$ was mixed with different concentrations of McC1 by shaking overnight at room temperature (220 rpm). After removing insoluble matter by brief centrifugation, the absorbance of the supernatant was measured at 275 nm and the concentration of $UQ_{10}$ was determined by its extinction coefficient of 14.2 $mM^{-1} cm^{-1}$. Each point is the average of two samples, and error bars indicate standard deviation. At concentrations above 50 µM, with the increases in McC1 concentration the amount of solubilized UQ increases linearly, indicating that the effect is related to micellization.

Solubilization studies. In order to link the surfactant properties of McC1 and its stimulating impact on $UQ_{10}$ uptake, the solubilization characteristics of McC1 on $UQ_{10}$ have been determined. First, solubilization test was performed by overnight shaking of a mixture of $UQ_{10}$ and McC1 in water. The resultant suspensions were then centrifuged at 6,000×g for 2 min to remove undissolved $UQ_{10}$ The absorbance of the filtrate at 275 nm was measured spectrophotometrically and concentrations of $UQ_{10}$ were determined from its extinction coefficient of $\varepsilon=14,200$. FIG. 11 shows that in the presence of McC1, the water solubility of $UQ_{10}$ is greatly increased, and at concentrations above 50 μM, with the increases in McC1 concentration the amount of solubilized UQ increases linearly, indicating that the effect is related to micellization (micelle formation which occurs due to self aggregating properties of the surfactant molecule)

Additional solubilization tests were performed using sonication. Excess amount of $UQ_{10}$ was mixed with McC1 by sonication for 2 min in water. The resultant suspensions were then filtered through a 0.45 μm or 0.22 μm syringe filter to remove undissolved $UQ_{10}$ The absorbance of the filtrate at 275 nm was measured spectrophotometrically and concentrations of $UQ_{10}$ were determined from its extinction coefficient of $\varepsilon=14,200$. FIG. 12 shows increased solubilization of $UQ_{10}$ by addition of McC1 followed by mixing by sonication, and that sonication results in higher solubility.

Figure 9:
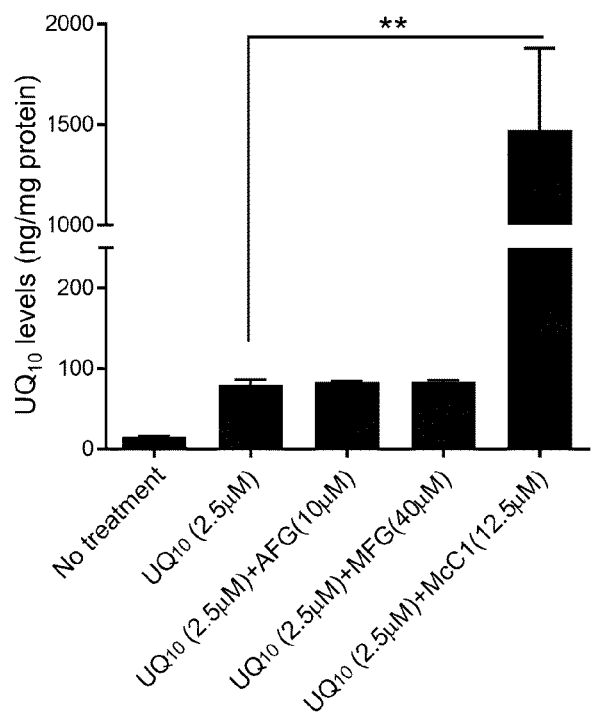
FIG. 9 presents exemplary data showing cellular uptake of exogenous $UQ_{10}$ in the presence of anidulafungin (AFG) and micafungin (MFG). Results are shown as the levels of $UQ_{10}$ (measured as ng/mg of protein) in Pdss2/Mclk1 DKO MEFs without any treatment, after treatment with 2.5 µM of $UQ_{10}$, after co-treatment 2.5 µM of $UQ_{10}$ and 10 µM of AFG, after co-treatment 2.5 µM of $UQ_{10}$ and 40 µM of MFG, or after co-treatment 2.5 µM of $UQ_{10}$ and 12.5 µM of McC1. Values are mean±SEM (n=3). **$p<0.01$ (one-way ANOVA). For AFG and MFG, a dose close to their highest non-toxic doses was used.

To explore the structure specificity of the effects on $UQ_{10}$ solubilization and uptake, two close structural analogs of McC1 sharing a similar cyclic peptide structure were tested. In McC1, a cyclic hexapeptide is linked to a fatty acid chain, whereas Anidulafungin (AFG) has an alkoxytriphenyl side chain and micafungin (MFG) has a complex aromatic sidechain. Cellular $UQ_{10}$ levels were measured in wildtype MEFs after co-treatment with anidulafungin (AFG) and $UQ_{10}$, co-treatment with micafungin (MFG) and $UQ_{10}$, and treatment with $UQ_{10}$ alone. As shown in FIG. 9, in comparison to supplementation with $UQ_{10}$ alone, addition of AFG or MFG did not further increase the level of $UQ_{10}$ in wildtype MEFs. Thus, unlike McC1, AFG and MFG were ineffective at enhancing cellular uptake of exogenous $UQ_{10}$.

Figure 10:
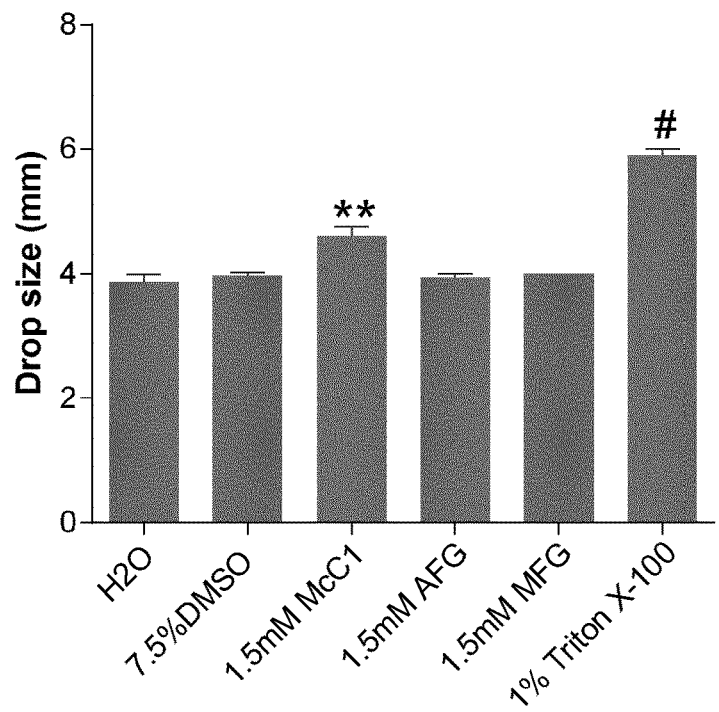
FIG. 10 presents a bar chart showing the drop-collapsing ability of McC1, AFG, MFG and Triton X-100. The drop size corresponds to the diameters of compound-containing water droplets placed on a hydrophobic Parafilm® surface. Results are provided as the drop size (in mm) of water solutions containing the indicated compounds. Water containing 7.5% DMSO, which is the highest concentration of the vehicle in the test compound solutions, was used as control. Values are mean±SEM (n=3). **$p<0.01$; #$p<0.0001$ vs. DMSO control (one-way ANOVA).

FIG. 10 illustrates that AFG and MFG showed no drop collapse activity at the doses tested. Without wishing to be bound to any particular theory, we postulate that the presence of a fatty acid chain is important for the amphiphilic property of McC1, and that its amphiphilic property is necessary for its ability to solubilize UQ and stimulate uptake of exogenous UQ by the cells.

Example IV—Evaluation of Compounds Structurally Similar to Caspofungin

Figure 17A:
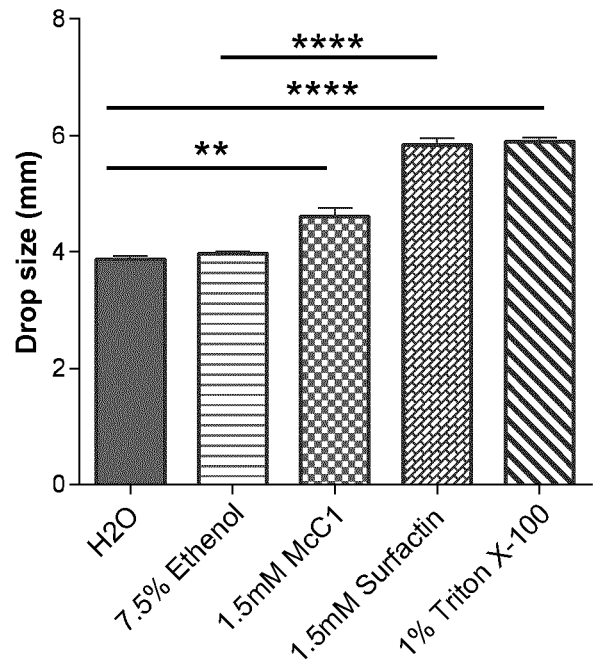
FIG. 17A to 17E present the results of the effects of surfactin on water solubility of $UQ_{10}$ and cellular uptake of exogenous $UQ_{10}$. (A) Bar chart showing the drop-collapsing ability of McC1 along with surfactin and Triton X-100. The drop size correspond to the diameters of compound-containing water droplets placed on a hydrophobic Parafilm® surface. Water containing 7.5% ethanol, which is the final concentration of ethanol in the surfactin solution, was used as the control for surfactin. Results are shown as the drop size (in mm) for water, ethanol at 7.5%, McC1 at 1.5 mM, surfactin at 1.5 mM and 1% Triton X-100. Values are mean±SEM (n=3). p<0.01; p<0.0001 vs. corresponding controls (one-way ANOVA). (B) Plot showing increased water solubility of $UQ_{10}$ in the presence of surfactin or McC1. Results are presented as the concentration of solubilized $UQ_{10}$ (measured as µM) found in the clear supernatant after mixing $UQ_{10}$ with McC1 (dashed line) or surfactin (complete line) overnight at room temperature by vigorous shaking. Each point is the average of two samples, and error bars indicate standard deviation. (C) Bar charts presenting exemplary data showing that surfactin increases uptake of exogenous $UQ_{10}$ into cells and mitochondria. The panel on the left shows the change of $UQ_{10}$ levels (in ng/µg protein) in Pdss2/Mclk1 DKO MEFs after 3 days of treatment with $UQ_{10}$ or $UQ_{10}$ in combination with surfactin. Values are mean±SEM (n=3). ND: Not Detectable. p<0.0001 (one-way ANOVA). The panel on the right shows $UQ_9$ and $UQ_{10}$ levels in mitochondrial extracts from wild-type MEFs after 3 days of treatment with $UQ_{10}$ alone, $UQ_{10}$ in combination with McC1 and $UQ_{10}$ in combination with surfactin at the indicated concentrations. The mitochondrial uptake of exogenous $UQ_{10}$ in the presence of surfactin is less than that aided by the presence of McC1. are mean±SEM (n=3). **p<0.0001 (two-way ANOVA). (D) A column graph showing cell viability of DKO cells after 3 days' culture in glucose-free galactose-containing medium in the presence of surfactin or of a low concentration of $UQ_{10}$ alone, or of both agents. Surfactin by itself has no effect on galactose-induced lethality of DKO cells, but enhances the rescue effect of exogenous $UQ_{10}$. Glc: glucose; Gla: galactose. Error bars represent mean±SEM (n=7-8). *p<0.05; **p<0.0001 (one-way ANOVA). (E) Oxygen consumption rate (OCR) measurements carried out on DKO cells treated with surfactin or a small amount of $UQ_{10}$ or a combination of surfactin and $UQ_{10}$. Oxygen consumption was measured using a Seahorse XF24 Flux Analyzer and results are provided as pmol/min/µg of protein. Data are expressed as mean±SD (n=2-6). **p<0.0001 (two-way ANOVA). Higher respiration rates were observed in the DKO cells treated with surfactin and $UQ_{10}$ together compared with cells treated with $UQ_{10}$ alone. The results shown in the FIGS. 17D and 17E further demonstrate that in the presence of surfactin, mitochondrial uptake of exogenous $UQ_{10}$ is augmented.

Like caspofungin/McC1, surfactin is a cyclic lipopeptide. It is produced from various strains of *Bacillus subtilis*. Structurally it consists of a peptide chain formed by seven amino acids linked to a β-hydroxyl fatty acid via a lactone bond. It is known for its exceptional surfactant power. In the drop collapse assay result of FIG. 17A, a potent surfactant activity was observed for surfactin. Then, solubilization test was performed by overnight shaking of a mixture of $UQ_{10}$ and surfactin in water. The mixture were subjected to brief centrifugation to separate undissolved $UQ_{10}$ before absorbance of the resultant clear supernatant at 275 nm was measured spectrophotometrically. Concentrations of $UQ_{10}$ were then determined from its extinction coefficient of $\varepsilon=14,200$. The results shown on FIG. 17B demonstrate that: first, water solubility of $UQ_{10}$ is increased in the presence of surfactin; and second, surfactin has lower solubilization power than McC1 for UQ, though it has greater ability to lower surface tension. This finding suggests that, compared to surfactin, the chemical structure of McC1 allows for a higher solubilization power for UQ, probably by allowing for a higher loading capacity in McC1 micelles.

Figure 17B:
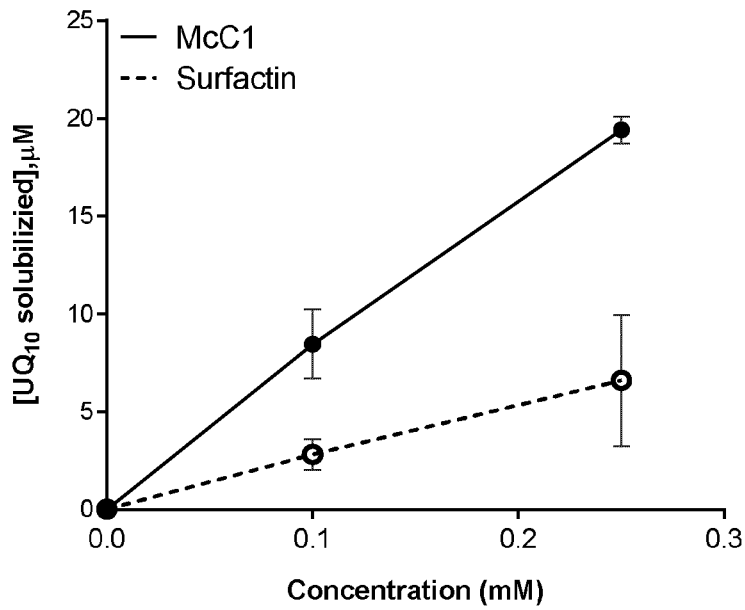
Figure 17C:
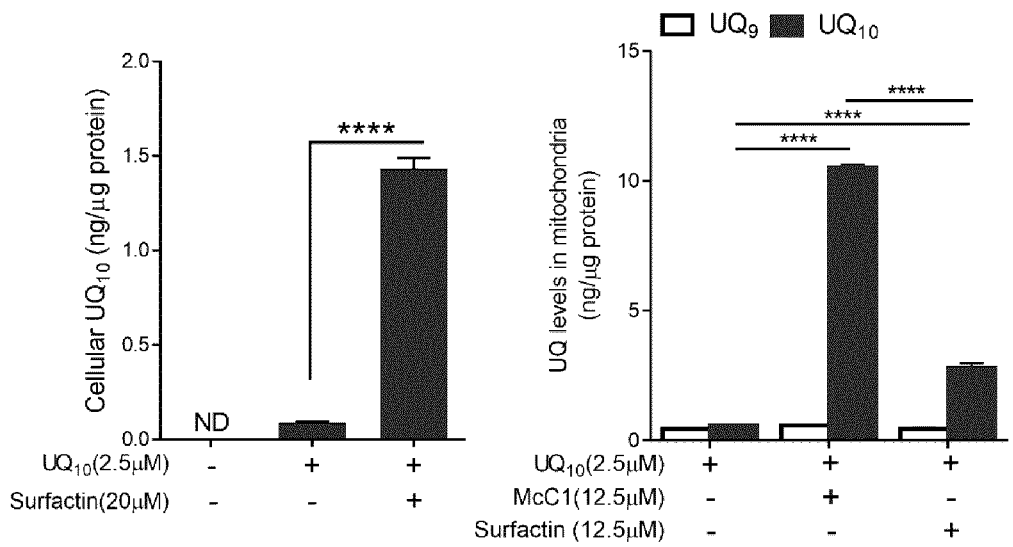
Figure 17D:
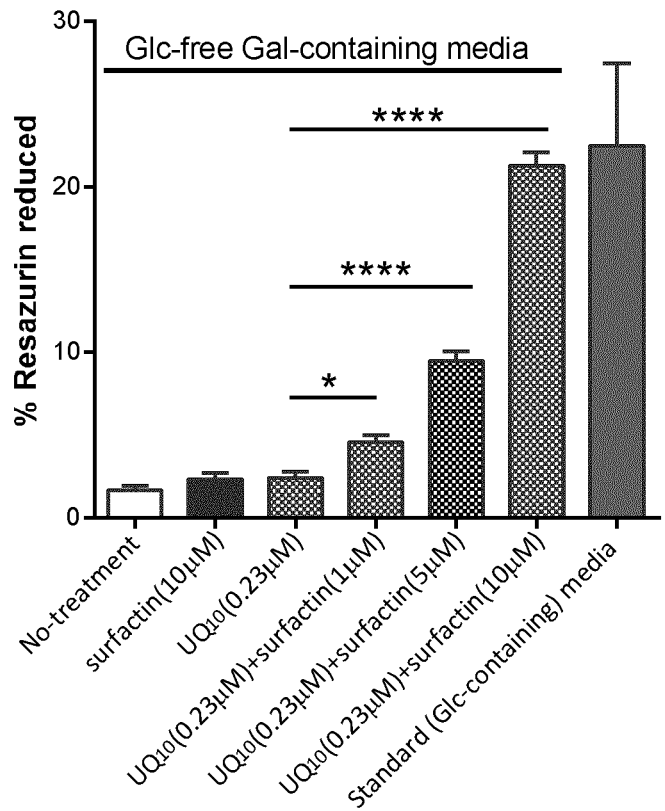
Figure 17E:
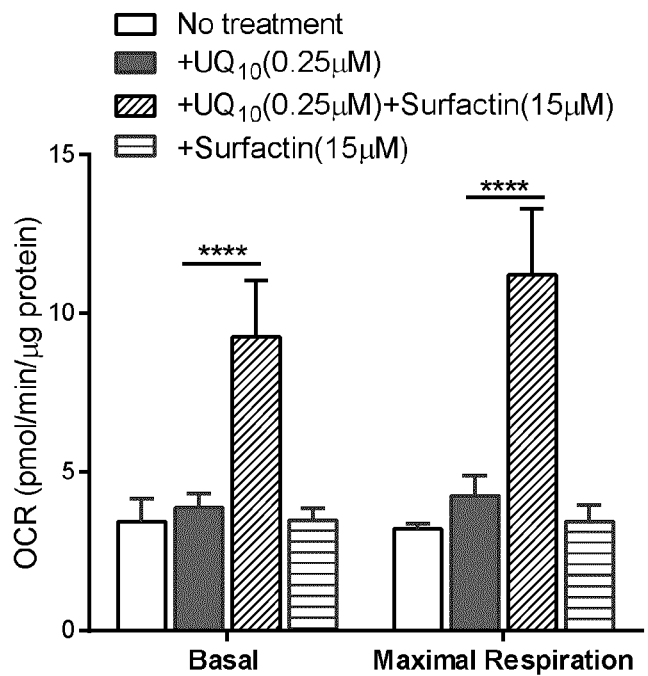

To determine whether surfactin also can enhance cellular uptake of exogenous UQ, $UQ_{10}$ levels were measured in Pdss2/Mclk1 DKO MEFs after co-treatment with surfactin and $UQ_{10}$ or treatment with $UQ_{10}$ alone. The results shown on FIG. 17C (left panel) indicate that the addition of surfactin to culture media improves $UQ_{10}$ uptake into cells. UQ levels in the mitochondria was measured in wild-type MEFs after co-treatment with McC1 and $UQ_{10}$, co-treatment with surfactin and $UQ_{10}$, and treatment with $UQ_{10}$ alone. The results shown on FIG. 17C (right panel) indicate augmented uptake of UQ into mitochondria in the cells treated with combination of surfactin and $UQ_{10}$ compared to the cells treated with $UQ_{10}$ alone. It is also noteworthy that, compared to McC1, surfactin shows less stimulating action on UQ uptake into mitochondria. Nevertheless, as shown in FIG. 17D, in the presence of a small amount of $UQ_{10}$ which by itself was not sufficient to support survival of the mutant cells in a respiration-dependent media, surfactin was able to produce full viability rescue at 10 μM. And it enhances the rescue effect of exogenous $UQ_{10}$ on mitochondrial dysfunction of Pdss2/Mclk1 DKO cells (FIG. 17E). These further confirm enhanced delivery of exogenous UQ into mitochondrial membrane in the presence of surfactin.

Figure 21A:
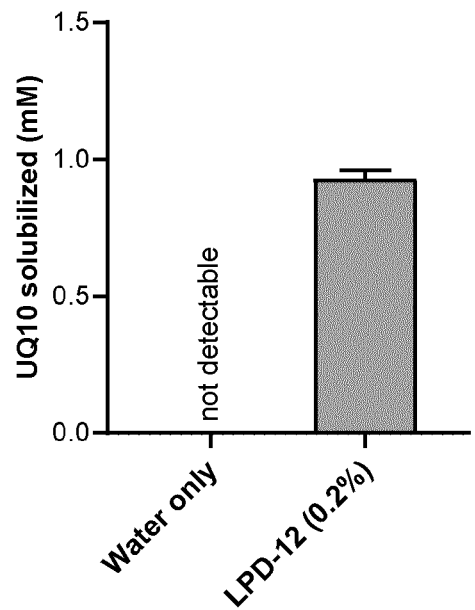
FIG. 21 provides bar charts showing that lipopeptide detergent-12 (LPD-12) increases the water solubility of $UQ_{10}$ and that treating MEFs with the LPD-12 solubilized $UQ_{10}$ results in accumulation of a greater amount of $UQ_{10}$ in the cells compared to the $UQ_{10}$ alone treatment. (A) A bar chart demonstrating that mixing $UQ_{10}$ and LPD-12 aided by sonication results in a higher solubility of $UQ_{10}$. Shown is the concentration of $UQ_{10}$ in a water solution or in the presence of 0.2% LPD-12 after filtration with 0.22 um syringe filter. The concentration of $UQ_{10}$ was determined by its extinction coefficient of 14.2 mM$^{-1}$ cm$^{-1}$ at 275 nm. (B) a bar chart demonstrating increased $UQ_{10}$ concentrations in wild-type MEFs after 1-day treatment with the solubilized formulation of $UQ_{10}$ in water made by using LPD-12 or free $UQ_{10}$ alone. Results are shown as $UQ_{10}$ levels (ng/mg protein) in control condition (+None), after treatment with LPD-12-solubilized form of $UQ_{10}$, after treatment with McC1-$UQ_{10}$ solution, or after treatment with free $UQ_{10}$ only (+$UQ_{10}$). In the 3 treatment conditions, the final $UQ_{10}$ concentrations in the media were the same—8 µM. Error bars represent mean±SEM (n=2). #$p<0.0001$ (two-way ANOVA plus Tukey's post test).
Figure 21B:
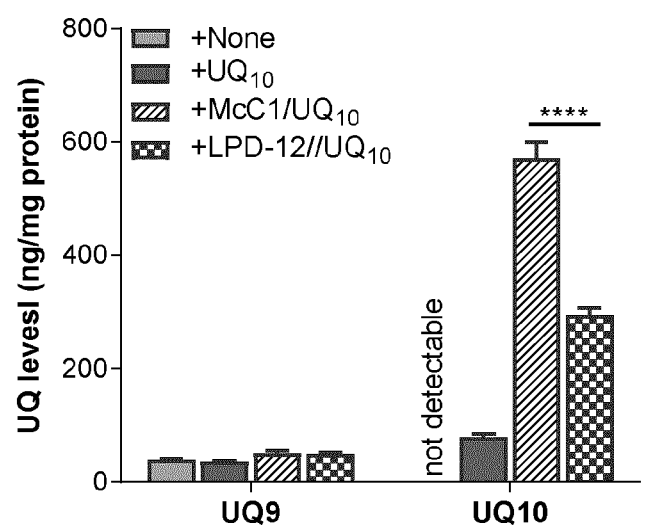

We further tested another lipopeptide compound LPD-12 which is an lipopeptide detergent (LPD), a new class of amphiphile designed specifically for the structural study of integral membrane proteins. LPDs are engineered to form small cylindrical assemblies with rigid exterior surfaces that is designed to provide a natural interior packing environment for fatty acid chains. LPD-12 consists of a 25 amino acid α-helical peptide scaffold that is attached to a 12 carbons alkyl chain. Solubilization test aided with sonication shows that LPD-12 increases the water solubilization of $UQ_{10}$ (FIG. 21A). The resulting micellar solution was used to treat wild-type MEFs to determine their effect on cellular uptake of exogenous UQ. FIG. 21B demonstrates augmented uptake of $UQ_{10}$ into the cells treated with the LPD-12 solubilized $UQ_{10}$ compared to the cells treated with the same amount of $UQ_{10}$ that was added to the culture media alone. Of note, compared to McC1-$UQ_{10}$ solution, LDP-12 solubilized $UQ_{10}$ showed less efficiency in facilitating UQ delivery into the cell.

Example V—Evaluation of Amphiphilic Compounds

Figure 18A:
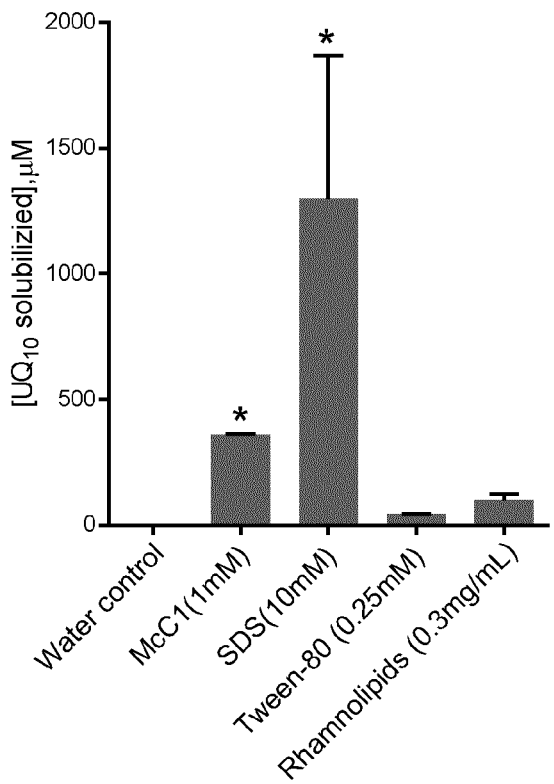
FIG. 18A to 18D presents the results of the effect of McC1 and other several known amphiphilic molecules [Sodium dodecyl sulfate (SDS), Tween-80, Poly(ethylene glycol)-block-poly(d,l-lactic acid)(PEG-b-PLA), rhamnolipids, Saponins, Tetradecyl trimethyl ammonium bromide (TTAB), Benzalkonium chloride (BAC), and PLGA-PEG-PLGA copolymers (Poly(lactide-co-glycolide)-b-poly(ethylene glycol)-b-poly(lactide-co-glycolide), LG 50:50 (w:w)] on the solubilization of $UQ_{10}$ in water. Results are shown as the concentration of solubilized $UQ_{10}$ (µM or mM) in the solutions of the indicated tested compounds. Direct dissolution method aided by sonication was used to mix $UQ_{10}$ and the indicated tested compounds. The resulting solutions were filtered to remove any insoluble matter and the absorbance of the filtrates was measured at 275 nm. The $UQ_{10}$ concentrations were then determined by its extinction coefficient (14.2 mM$^{-1}$ cm$^{-1}$ at 275 nm). (A) Results are shown for the water control, McC1 provided at a concentration of 1 mM, SDS at a concentration of 10 mM, Tween-80 at a concentration of 0.25 mM and rhamnolipids at a concentration of 0.3 mg/mL. Shown are mean±SEM (n=2). There is no detectable soluble $UQ_{10}$ in the water-only control. (B) Results are shown for the water control, McC1 provided at a concentration of 4 mM, SDS at a concentration of 4 mM. Shown are mean±SEM (n=3). (C) Results are shown for the water control and PEG(2000)-b-PLA(1800) at 0.5% w/w and 2% w/w. In PEG(2000)-b-PLA(1800) which is used in the test the molecular weight of PEG and PLA is 2000 and 1800 g/mol, respectively. Shown are mean±SEM (n=3). (D) Results are shown for Saponins, TTAB, BAC and PLGA-PEG-PLGA. The error bars indicate standard error of the mean (n=1-3). *$p<0.05$; **$p<0.01$ (vs. the water control; one-way ANOVA plus Dunnett's multiple comparison test).
Figure 18B:
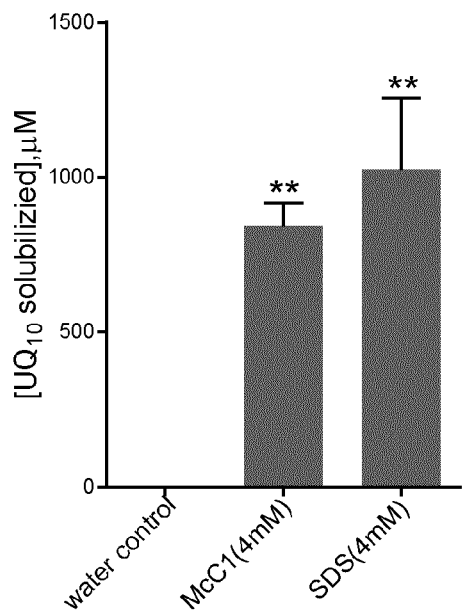
Figure 18C:
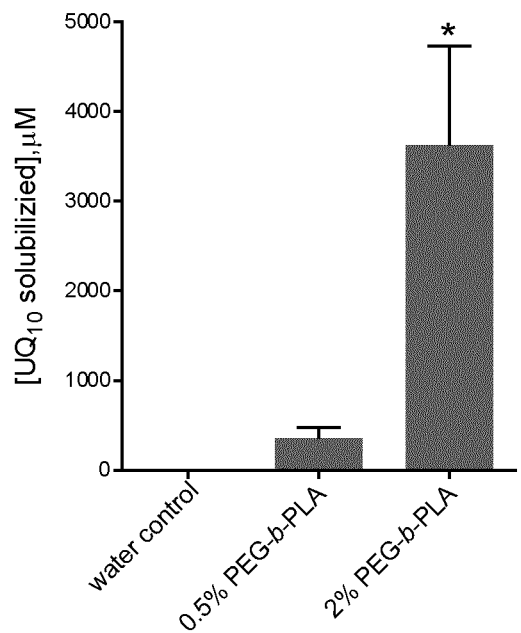

Several other surfactants were tested for their ability to solubilize UQ. Briefly, excess amount of $UQ_{10}$ was mixed with water solution of the tested surfactants using sonication. The resultant suspensions were then filtered through a 0.45 μm syringe filter to remove undissolved $UQ_{10}$. Absorbance at 275 nm was measured spectrophotometrically and concentrations of $UQ_{10}$ were determined from its extinction coefficient of ε=14,200. The results shown on FIG. 18A indicate that SDS and McC1 allows the solubilization of $UQ_{10}$ in water. At same concentration, McC1 and SDS surfactant show similar performances for solubilizing $UQ_{10}$ (FIG. 18B). The copolymer PEG(2000)-b-PLA(1800) is also capable of solubilizing $UQ_{10}$ in aqueous solution (FIG. 18C).

Figure 18D:
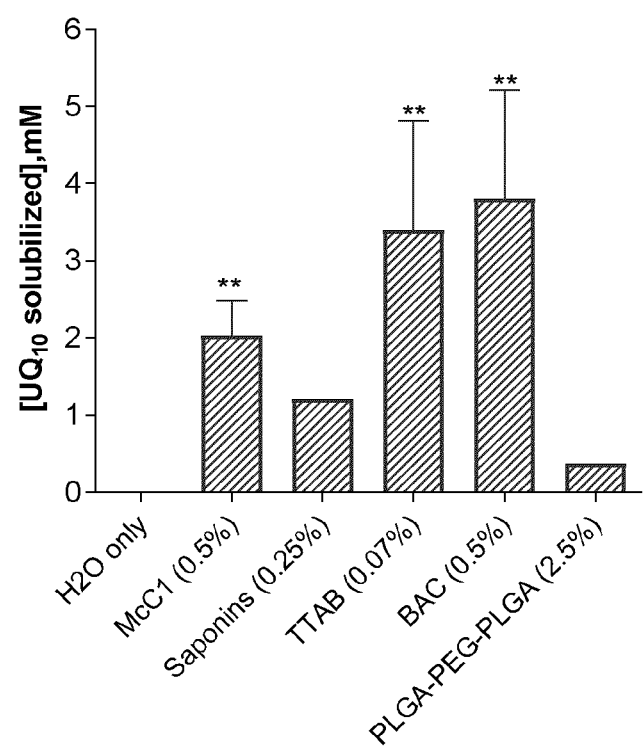

Further surfactants were assessed for their ability to solubilize UQ. As shown in FIG. 18D, Saponins, Benzalkonium chloride (BAC), Tetradecyl trimethyl ammonium bromide (TTAB), and PLGA-PEG-PLGA (Poly(lactide-co-glycolide)-b-poly(ethylene glycol)-b-poly(lactide-co-glycolide)) also improve the water solubility of $UQ_{10}$.

Figure 19A:
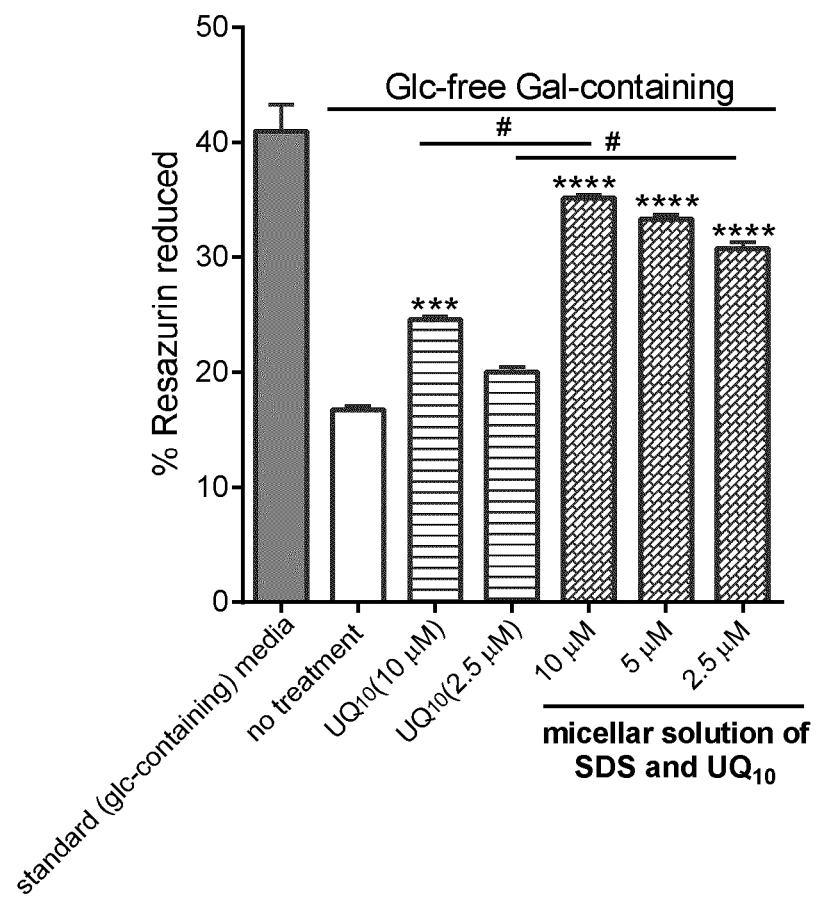
FIG. 19 provides exemplary data showing the recue effect of the micellarly solubilized $UQ_{10}$ prepared with PEG (2000)-b-PLA or SDS on the lethality of Pdss2/Mclk1 DKO cells in glucose-free galactose-containing media. (A) Viability of DKO cells after 2 days' culture in glucose-free galactose-containing media added with no additional agent (no treatment), with $UQ_{10}$, or with the micellar solution of SDS and $UQ_{10}$. Error bars represent mean±SEM (n=6). *$p<0.001$; $p<0.0001$ (vs. no treatment control); #$p<0.0001$ (comparison between 2 groups with the same concentration of $UQ_{10}$, one-way ANOVA followed by Tukey's multiple comparison test). (B) Viability of DKO cells after 2 days' culture in glucose-free galactose-containing media added with or without the micellar solution of PEG(2000)-b-PLA(1800) and $UQ_{10}$. Error bars represent mean±SEM (n=3). The expected final concentration of $UQ_{10}$ in the media is shown. The viability of DKO cells at the end of culture time was determined by resazurin reduction assay. Glc: glucose. Gla: galactose. **$p<0.0001$ [vs. no treatment control; one-way ANOVA followed by Dunnett's multiple comparison test]. Both micellar solutions are able to rescue the lethality of DKO cells in glucose-free galactose-containing media, indicating successful delivery of bioavailable $UQ_{10}$ into mitochondria.
Figure 19B:
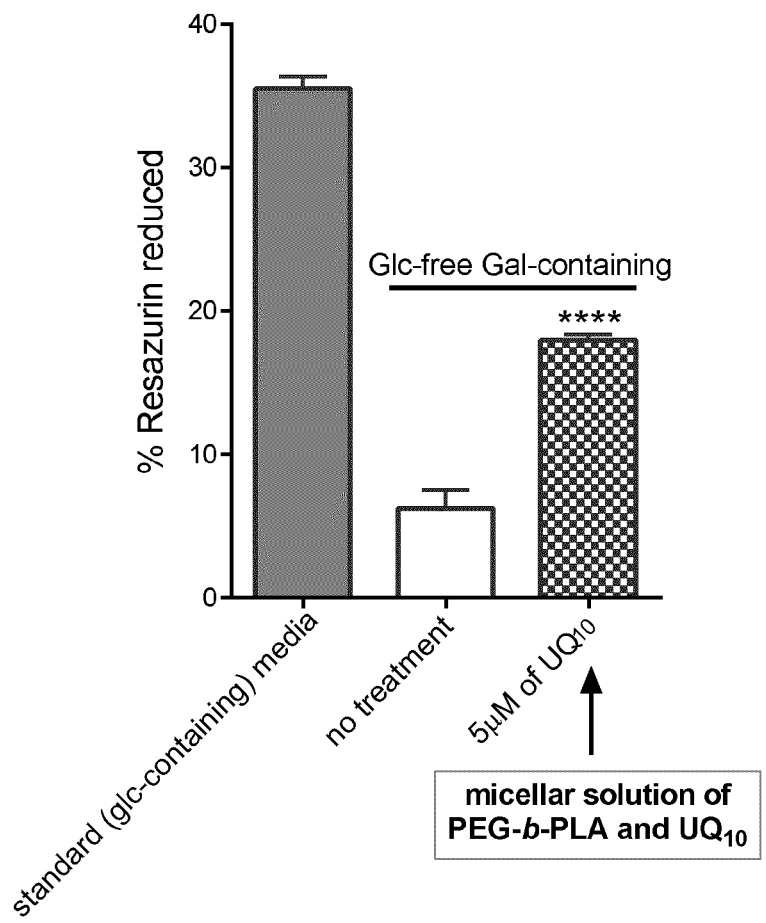
Figure 22:
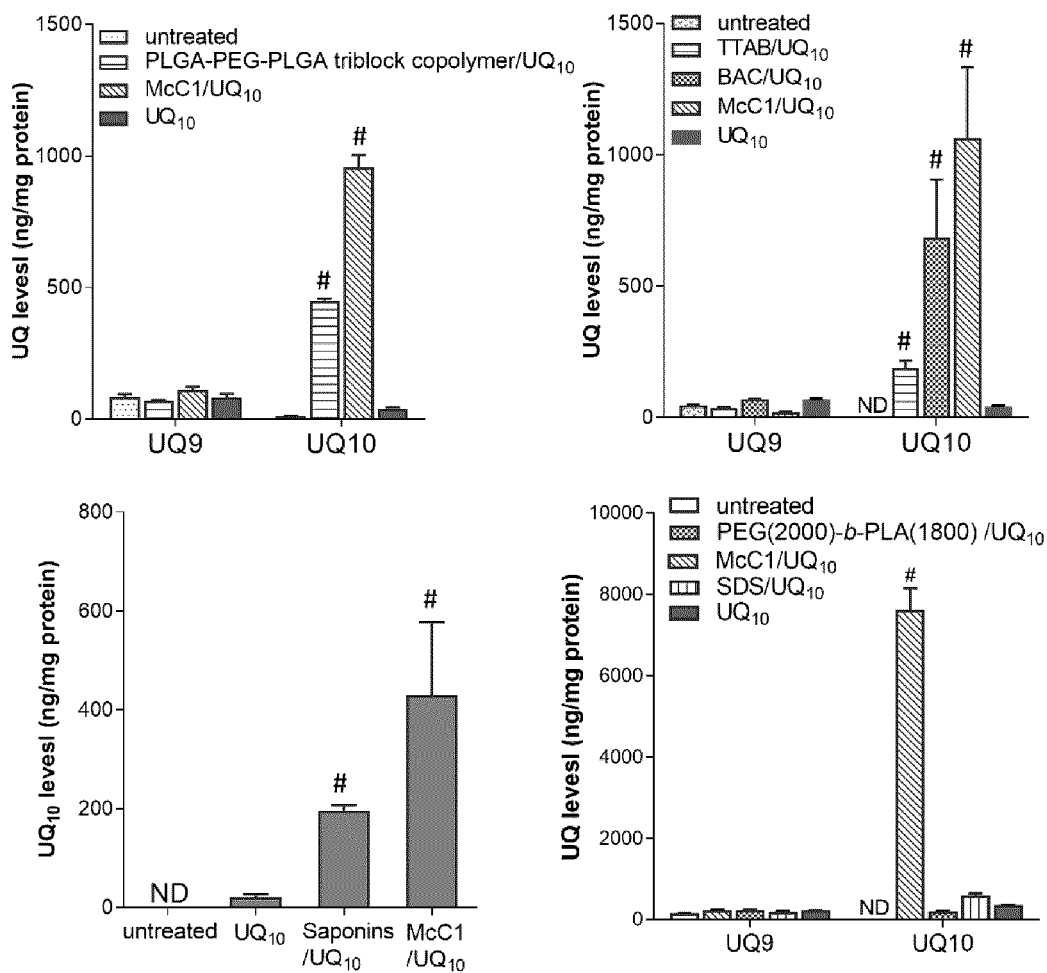
FIG. 22 presents the results of cellular UQ measurements after treatments with micellar $UQ_{10}$ solutions made with the indicated compounds. UQ levels are expressed as ng per mg of protein (mean±SEM). Each bar represents the average of 2 to 3 independent measurements. Except for the data presented in the lower right panel for which UQ were extracted after 3 days' treatment, UQ levels were determined after 1-day treatment with soluble mixtures of $UQ_{10}$ and the indicated compounds. For all treatments, the resulting $UQ_{10}$ concentrations in the media were the same: 6 µM. BAC: Benzalkonium chloride; TTAB: Tetradecyl trimethyl ammonium bromide; PLGA-PEG-PLGA: Poly(lactide-co-glycolide)-b-poly(ethylene glycol)-b-poly(lactide-co-glycolide), LG 50:50 (w:w). ND: not detected. #$p<0.0001$ (vs. untreated controls; two-way ANOVA followed by Dunnett's multiple comparison test).

The $UQ_{10}$ solutions prepared by the surfactants indicated above were tested for their effect on cellular $UQ_{10}$ uptake. As shown in FIG. 22, the $UQ_{10}$ solution prepared with PLGA-PEG-PLGA, TTAB, BAC or saponins, also showed increased cellular uptake of $UQ_{10}$ compared to adding $UQ_{10}$ alone into the media. However, at the indicated tested concentrations, all of them are less efficient than McC1/$UQ_{10}$ at delivering UQ into the cell. After 3 days' exposure, the $UQ_{10}$ solution comprising SDS or PEG(2000)-b-PLA (1800) as the solubilizing agent failed to increase cellular UQ levels. However, the data in FIG. 19A show that the micellar solution of SDS/$UQ_{10}$ can enhance the survival of Pdss2/Mclk1 DKO cells in galactose (respiration-dependent) medium and the rescue by the SDS/$UQ_{10}$ micelle was more pronounced compared to addition of free $UQ_{10}$ of the same dose. The data in FIG. 19B show that micellized $UQ_{10}$ prepared with PEG(2000)-b-PLA(1800) also enhances the survival of Pdss2/Mclk1 DKO cells in galactose medium. These results indicate that SDS micelles and PEG(2000)-b-PLA(1800) micelles can also encapsulate bioavailable UQ, however, their efficiency of $UQ_{10}$ delivery is very low.

Example VI—Microscopic Evaluation of Aqueous Solutions Comprising McC1 and UQ

Figure 23:
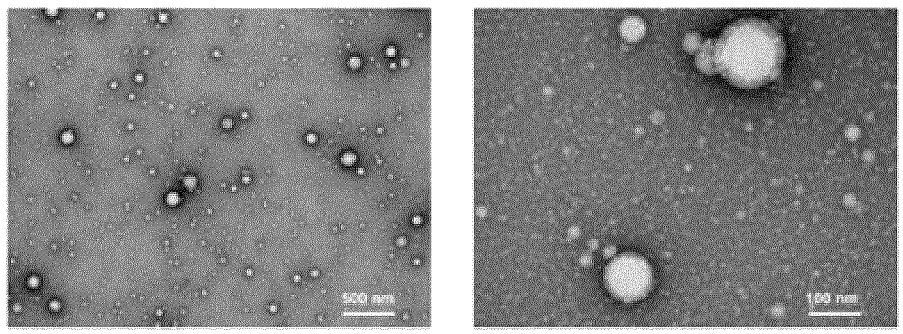
FIG. 23 presents Transmission electron microscopy (TEM) images of aqueous solution of a mixture of McC1 and $UQ_{10}$. Negative staining TEM revealed the formation of spherical assemblies of mixed sizes. Images from 2 different magnifications are shown. The observed aggregate particles are micelles.

An aqueous solution comprising McC1 and UQ was evaluated by Transmission Electron microscopy (TEM). Before TEM observation, a drop of McC1/$UQ_{10}$ solution was placed onto a copper grid and air dried, followed by negative staining with uranyl acetate for contrast enhancement. The samples were then examined under a Tecnai 12 BioTwin Transmission Electron Microscope (FEI Electron Optics) and images were digitized with the use of an AMT XR80C charge-coupled device camera and Image Capture Engine Software. As shown in FIG. 23, negative staining TEM revealed the formation of spherical assemblies of mixed sizes. The observed aggregate particles are micelles.

Example VII—Evaluation of Aqueous Micellar Formulations Comprising UQ

As shown herein, mixture of McC1 and UQ results in the formation of micelles. As such, the likely mechanism by which McC1 and other amphiphilic molecules solubilize UQ is related to micellization. To evaluate the micellar formulation of Mcc1/$UQ_{10}$, it was prepared by adding the 2 compounds into water followed by sonicating for 2 min. The resultant suspensions were then filtered through a 0.22 μm syringe filter in order to sterilize it and remove any undissolved matter. The filtrate (micellized UQ) is then stored at 4° C. until use.

Figure 13:
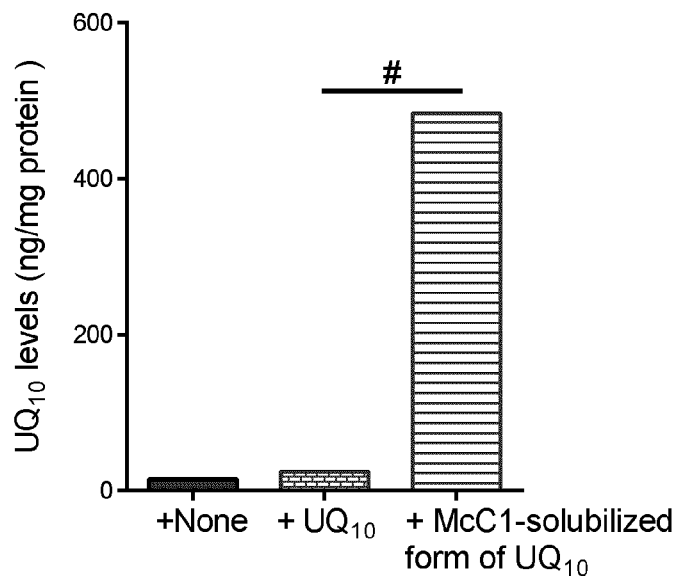
FIG. 13 presents a bar chart demonstrating increased $UQ_{10}$ concentrations in wild-type MEFs after 1 day treatment with the solubilized formulation of $UQ_{10}$ in water made by using McC1 or free $UQ_{10}$ alone. Results are shown as $UQ_{10}$ levels (ng/mg protein) in control condition (+None), after treatment with McC1-solubilized form of $UQ_{10}$, or after treatment with free $UQ_{10}$ only (+$UQ_{10}$). In the 2 treatment conditions, the final $UQ_{10}$ concentrations in the media were the same—2.5 µM. Error bars represent mean±SEM (n=2). #p<0.0001 (one-way ANOVA).
Figure 14:
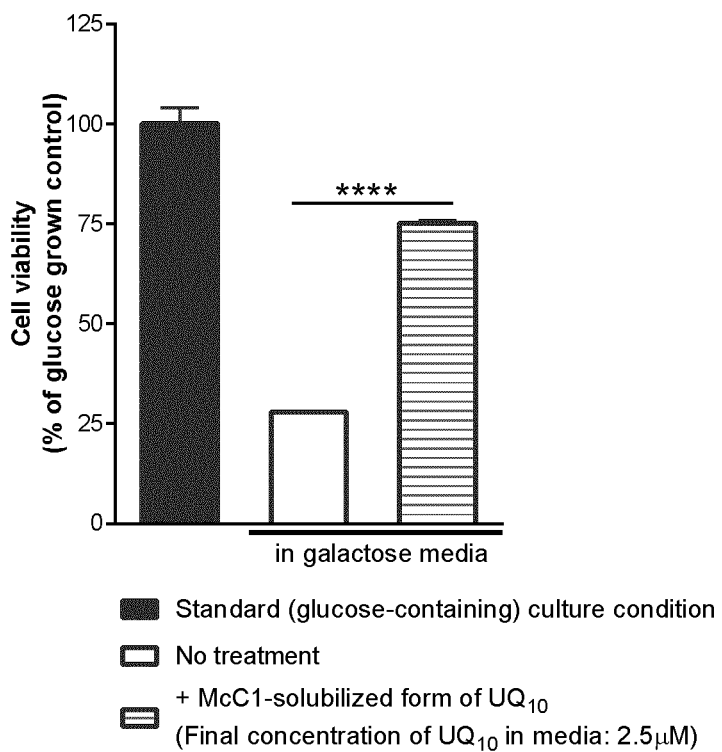
FIG. 14 presents a bar chart showing the effect of McC1-solubilized form of $UQ_{10}$ on the viability of Pdss2/Mclk1 DKO cells in a glucose-free galactose-containing media. Cell viability is measured by reduction of resazurin and is expressed as a percentage relative to standard (glucose-containing) culture condition. Values are mean±SEM (n=6). ****p<0.0001 (one-way ANOVA). Treatment with the McC1-solubilized form of $UQ_{10}$ rescues the lethality of DKO cells in galactose media, indicating effective delivery of $UQ_{10}$ into mitochondria.
Figure 15A:
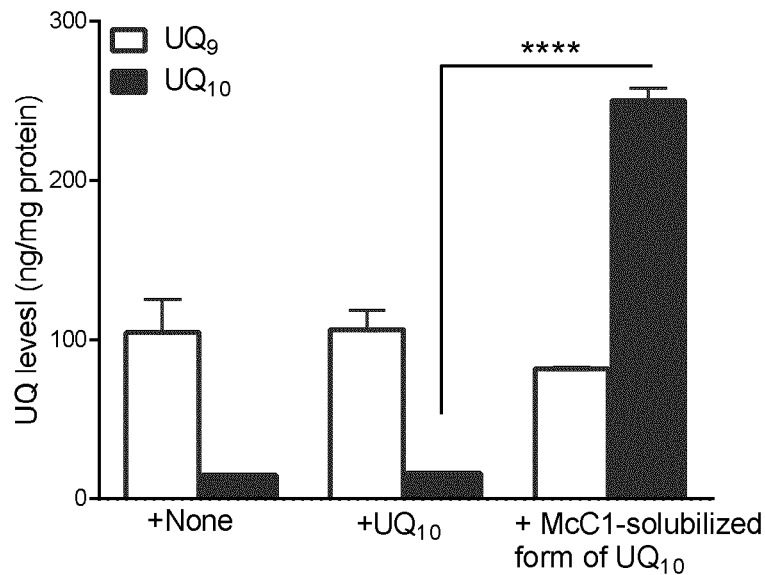
FIGS. 15A and 15B provide bar charts demonstrating the increase of $UQ_{10}$ concentrations in the cells 1 hour after treatment with a formulation containing $UQ_{10}$ in McC1-solubilized form. (A) UQ levels in wild-type MEFs after treatment with McC1-solubilized form of $UQ_{10}$. (B) UQ levels in human Hela cells after treatment with McC1-solubilized form of $UQ_{10}$. Results are shown as the levels of $UQ_9$ (white bars, measured as ng/mg of protein) or $UQ_{10}$ (black bars, measured as ng/mg of protein) in control conditions (+None), after treatment with a formulation containing McC1-solubilized form of $UQ_{10}$, or in the presence of $UQ_{10}$ only (+$UQ_{10}$). For the 2 treatment conditions in A, the final $UQ_{10}$ concentrations in the media were the same—2.5 µM. In B, the final $UQ_{10}$ concentrations in the media were 8 µM for the two treatment conditions. Values are mean±SEM (n=2). ****p<0.0001 (one-way ANOVA).
Figure 15B:
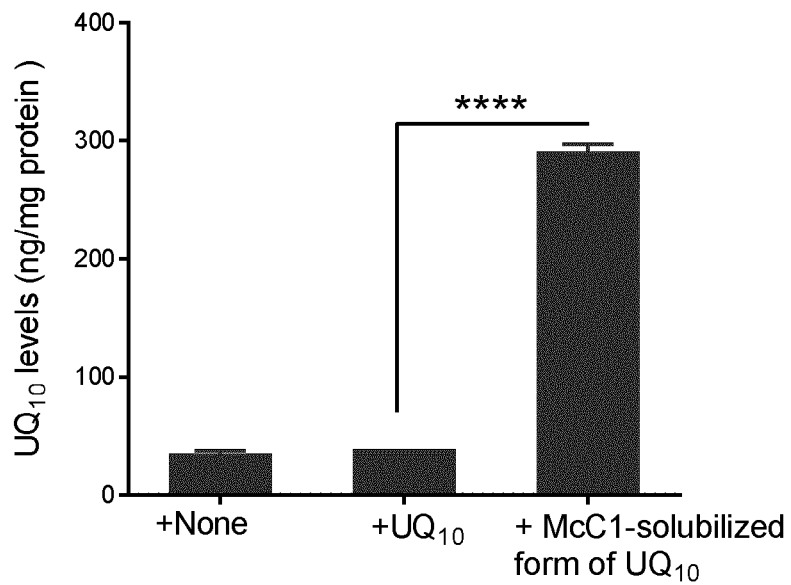

To treat cells, the micellar mixture of McC1 and $UQ_{10}$ was added to culture media directly. The results shown on FIG. 13 indicate that after 1 day treatment, $UQ_{10}$ level in wild-type MEFs treated with a micellar solution of McC1/$UQ_{10}$ was 20 times higher than that of the cells treated with the same amount of free $UQ_{10}$. The results shown on FIG. 14 demonstrate that a micellar suspension of McC1/$UQ_{10}$ was able to improve the survival of Pdss2/Mclk1 DKO cells in a respiration-dependent (glucose-free galactose-containing) medium, suggesting effective delivery of UQ into the mitochondria. The results in FIG. 15 show that for both mouse and human cells, 1 hour treatment with a micellar solution of McC1/$UQ_{10}$ was already sufficient to produce a dramatic increase in cellular $UQ_{10}$ levels, whereas the $UQ_{10}$ alone treatment of the same dose for the same duration showed no effect on intracellular $UQ_{10}$ levels. The micellar formulation can therefore achieve rapid and highly efficient UQ uptake.

Figure 16A:
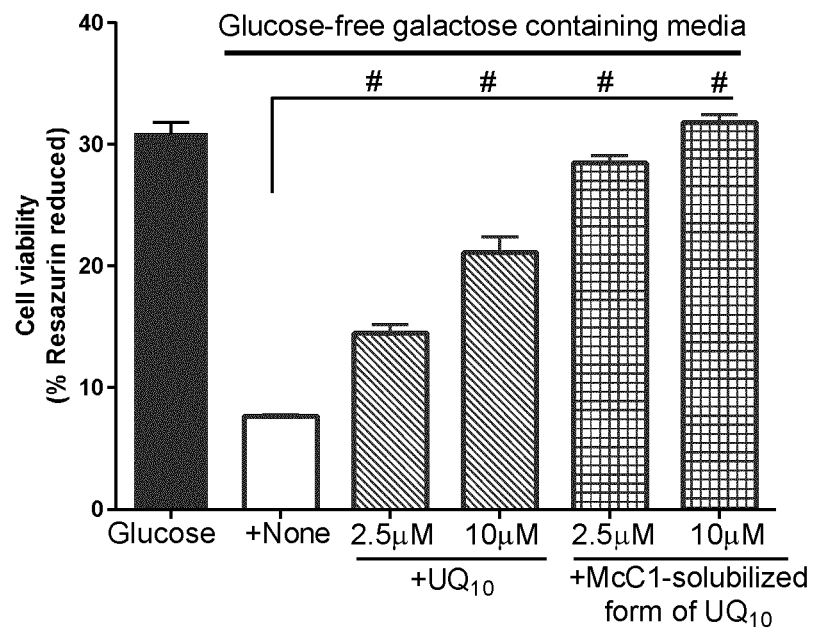
FIGS. 16A and 16B present results illustrating that $UQ_{10}$ supplementation with >3-weeks old water solution containing McC1-solubilized form of $UQ_{10}$ results in a dramatic increase of cellular UQ levels and improves the survival of Pdss2/Mclk1 DKO cells in glucose-free galactose-containing medium. (A) Results are shown as cell viability (in % of resazurin reduction as measured by the resazurin assay) for control condition (no treatment), after treatment with $UQ_{10}$ only (+$UQ_{10}$), and after treatment with a 3 weeks old water solution containing McC1-solubilized form of $UQ_{10}$. Error bars represent mean±SEM (n=6). For the treatment conditions, the final concentrations of $UQ_{10}$ in culture media are shown. #p<0.0001 (one-way ANOVA, followed by Dunnett's multiple comparisons test). Treatments with the McC1-solubilized form of $UQ_{10}$ results in better rescue of DKO cells from death in glucose-free galactose-containing medium. (B) Results are shown as the levels of $UQ_9$ or $UQ_{10}$ (measured as ng/mg of protein) of wild-type MEFs in control condition (+None), after treatment with a 1 week old or 5.5 weeks old water solution containing McC1-solubilized form of $UQ_{10}$ and after treatment with $UQ_{10}$ only (+$UQ_{10}$). For all the treatment conditions, the final concentrations of $UQ_{10}$ in the media were the same—8 µM. Cells were collected for ubiquinone analysis after 2 h treatment. Error bars represent mean±SEM (n=2). ND: not detectable. ns: not significant; #p<0.0001 compared to untreated control (two-way ANOVA, followed by Sidak's multiple comparisons test). The solutions containing McC1-solubilized form of $UQ_{10}$ were stored at 4° C. until use. There is no significant difference in cellular $UQ_{10}$ levels after treatment with the 1-week old or the 5.5-weeks old solution, indicating water solutions containing McC1-solubilized form of $UQ_{10}$ can be stable for at least 4.5 weeks if stored at 4° C.
Figure 16B:
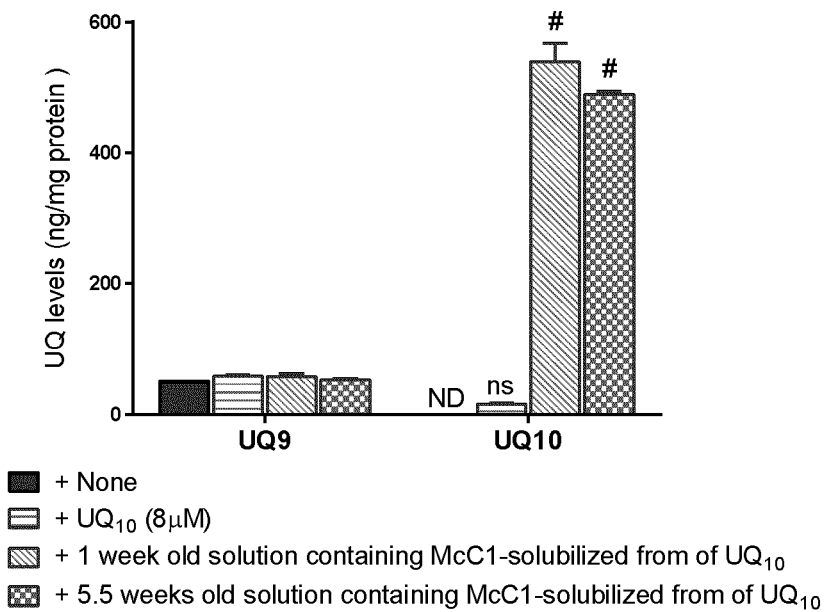

Additional tests were performed to determine the stability of McC1/$UQ_{10}$ micelles after storage. A micellar suspension of $UQ_{10}$ and McC1 containing $UQ_{10}$ at a concentration of about 1 mM was used. The micellar suspension was first stored for three weeks (at 4° C.) and then tested for its bioavailability by determining whether it was able to rescue the lethality of Pdss2/Mclk1 DKO cells in a glucose-free galactose-containing media. The results in FIG. 16A indicated that the viability of Pdss2/Mclk1 DKO cells in the respiration-dependent media was significantly increased if treated with the McC1/$UQ_{10}$ micelles and the micelle-treated DKO cells showed better survival than the DKO cells treated with $UQ_{10}$ alone (at the same doses). Further, FIG. 17B illustrated that there was no significant difference in cellular $UQ_{10}$ levels after treatment with 1-week old or 5.5-weeks old McC1/$UQ_{10}$ micellar solution, indicating McC1/$UQ_{10}$ micelles can be stable for at least 5.5 weeks if stored at 4° C.

Example VIII—Evaluation of the Effect of Caspofungin on Solubility of Other Hydrophobic Compounds Micellar systems can solubilize poorly soluble compounds and thus act as career vehicles for delivery and transport of hydrophobic drugs. In order to determine if caspofungin/McC1 can have an impact on other poorly soluble drugs, solubilization tests have been performed on hydrophobic dye Sudan I, polyphenol curcumin, and paclitaxel.

Figure 20:
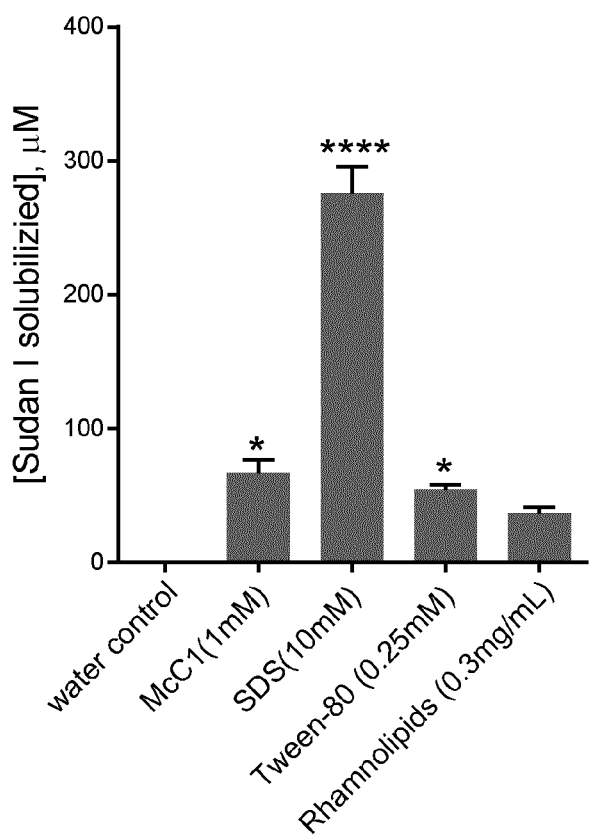
FIG. 20 provides a bar chart showing the effect of McC1 and other known surfactants (SDS, Tween-80 and rhamnolipids) on the water solubilization of Sudan I® dye. Direct dissolution method aided by sonication was used to mix Sudan I and the indicated tested compounds. The resulting solutions were filtered to remove any insoluble matter and the absorbance of the filtrates was measured at 476 nm. Sudan I concentrations were then determined by using a standard curve generated by known concentrations of Sudan I in 50% aqueous ethanol solution. Results are shown as the concentrations of solubilized Sudan I (in µM) in the water solutions of the indicated tested compounds. Shown are mean±SEM (n=2). *$p<0.05$; ****$p<0.0001$ (vs. the water control; one-way ANOVA plus Dunnett's multiple comparison test).

The dye Sudan I® was mixed with McC1, SDS, Tween-80 and rhamnolipids by sonication for 2 min in water. The resultant suspensions were then filtered through a 0.45 μm syringe filter to remove undissolved Sudan I® dye. Absorbance at 476 nm of the filtrate was measured spectrophotometrically and Sudan I concentrations were determined by using a standard curve generated by known concentrations of Sudan I in 50% aqueous ethanol solution. The results shown on FIG. 20 indicate that solubilization of Sudan I® in water is possible with McC1 as well as with the other surfactants tested.

Figure 24:
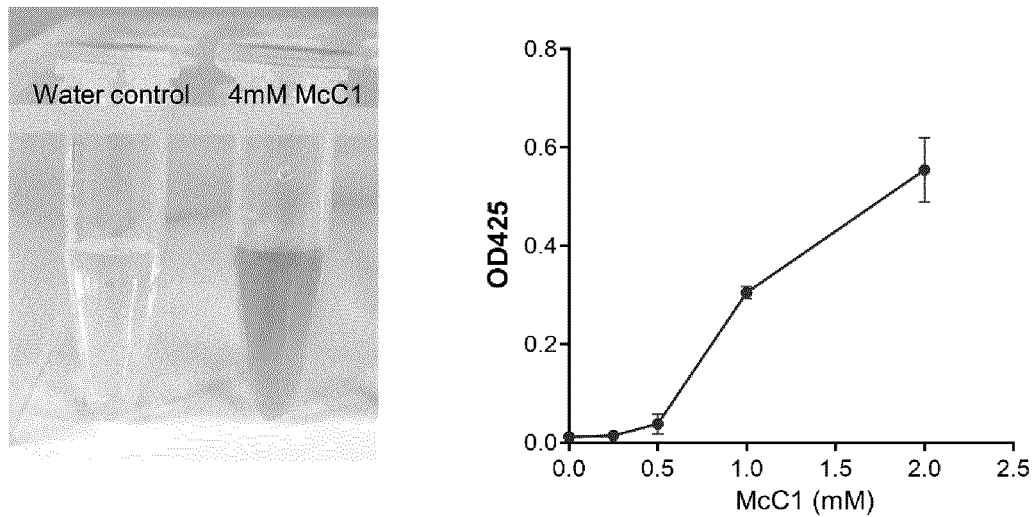
FIG. 24 shows the effect of McC1 on the solubility of curcumin in water. Curcumin is a natural yellow phenolic compound. Free curcumin has low solubility in aqueous solution. Left: images of curcumin solutions after mixing with 4 mM of McC1 or with water only. The solutions were filtered with a 0.22 µm membrane filter after mixing. Right: Dose-dependent solubilizing effect of McC1 on curcumin. Curcumin has a maximum absorbance at 425 nm; so absorbance of the filtrate was measured spectrophotomecally at 425 nm as an indication of the amount of solubilized curcumin. Values are mean±SEM (n=4).

A similar test was performed with curcumin, which is a hydrophobic polyphenolic compound that for example presents antimicrobial effects and cytotoxicity towards various cancer cell lines. However, curcumin is not water soluble and has limited bioavailability and instability, greatly hindering its clinical applicability. Curcumin was mixed with McC1 by sonication for 1 min in water. The resultant suspension was then filtered through a 0.45 μm syringe filter to remove undissolved matter. Absorbance at 425 nm of the filtrate was measured spectrophotometrically as an indication of the amount of curcumin in the solution. As shown in FIG. 24, free curcumin has very low solubility in water, but after being mixed with McC1, its solubility was greatly increased in a dose-dependent manner. It is important to note that in contrast with the other surfactants tested, McC1 is non-toxic and can be used in intravenous injection.

Figure 25:
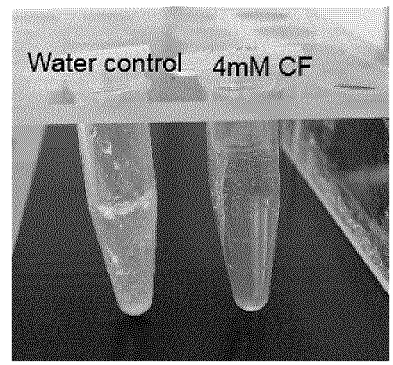
FIG. 25 shows the solubilizing effect of capsofungin/McC1 on paclitaxel (PTX). Shown are images of PTX solutions after mixing with McC1 or with water-only control lacking capsofungin/McC1. The water-only control on the left showing that PTX is not soluble in water, and is considerably more soluble following mixture with capsofungin/McC1, as shown on the right.

The solubility of the chemotherapy drug Paclitaxel (PTX) was also assessed. Because of its water insolubility, PTX is formulated in an organic solvent of polyoxyethylated castor oil (Cremophor EL™) to enhance drug solubility. However, Cremophor EL is known to cause serious side effects, such as hypersensitivity reactions. As a result, prolonged infusion time and pre-treatments are required. Moreover, it has been suggested that the presence of Cremophor EL could alter the pharmacokinetic profile of PTX in vivo. As shown in FIG. 25, capsofungin/McC1 shows solubilizing effects on PTX.

Figure 26A:
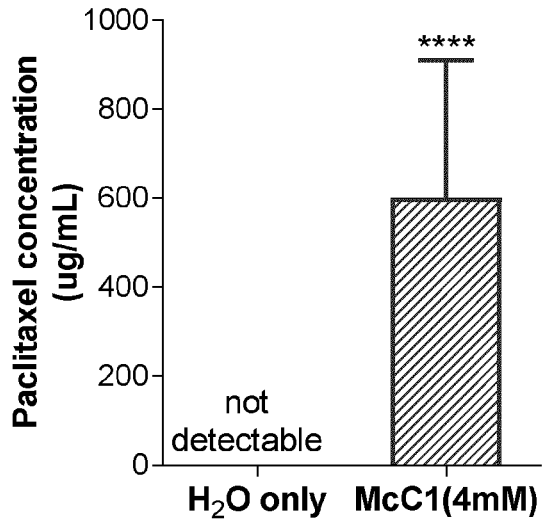
FIG. 26 presents (A) a bar graph showing the effect of McC1 on the water solubility of paclitaxel (PTX), as well as (B) the effect of a PTX/McC1 micelle solution on cell proliferation and survival. (A) Bar graph showing a concentration of soluble PTX in 4 mM McC1 solution. After mixing PTX and McC1 solution, the undissolved residues were removed by filtration through a 0.22 µm pore-size membrane. For determination of the PTX concentration, absorbance at 230 nm was measured and compared to a standard curve generated for known concentrations of PTX in pure methanol. Mean±SEM of 3 samples is shown. $p<0.0001$ (t-test). (B) The effect of PTX/McC1 micelle solution on cell proliferation and survival. Mouse embryonic fibroblasts (MEFs) were seeded into 48-well plates at a low density of $1×10^4$ cells/well. They were allowed to attach overnight and then PTX solubilized by McC1 was added to the media and the cells were cultured for 2 or 6 more days. Before the treatment and at then end of 2 days or 6 days' culture, the standard resazurin reduction assay was used to evaluate viable cell number. Shown are the fold changes of colorimetric signal generated from resazurin reduction compared to that before the treatments. Compared to the no-treatment control, McC1 alone caused no observable toxicity, whereas the PTX/McC1 treated cells showed decreased cell viability and/or growth. Error bar is SEM, n=4 to 6. *$p<0.05$ (compared to no-treatment and McC1 alone controls; two-way ANOVA).
Figure 26B:
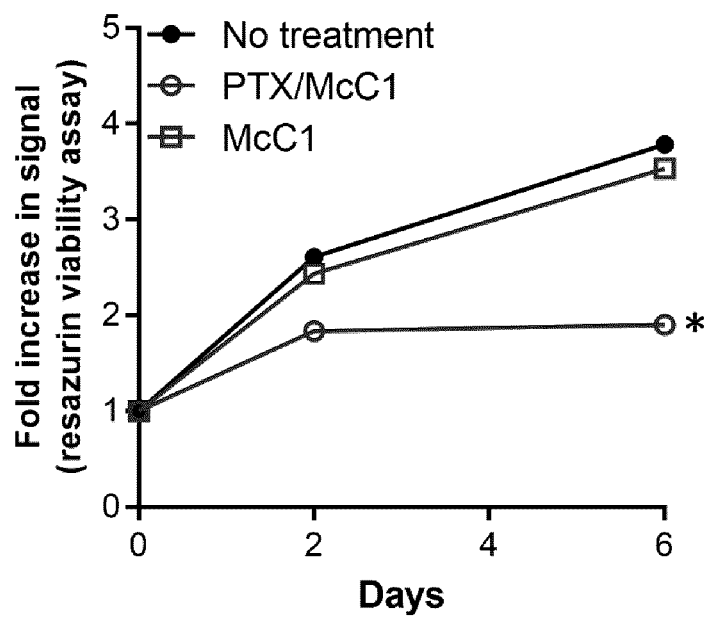

FIG. 26A shows further results demonstrating that capsofungin/McC1 increases the water solubility of PTX. To evaluate the antiproliferative activity of PTX/McC1 micelles, we seeded exponentially growing mouse embryonic fibroblasts (MEFs) into 48-well plates, exposed them to PTX/McC1 micelles for 2 to 6 days, and determined the treatment effect on cell growth and survival by comparing the numbers of variable cells before and after the treatment. FIG. 26B shows that at the doses tested, the McC1/PTX treated cells showed a dose-dependent cytotoxic effect, whereas McC1 alone caused no observable toxicity.

Therefore, since McC1 shows minimal toxicity, it could be used to produce medicinal formulations for hydrophobic drugs (such as CUR and PTX) with advantages of reduced toxicity and rapid drug administration.

Example IX—In Vivo Evaluation of Mcc1-Solubilized $UQ_{10}$ in Wild-Type Mice

Figure 27:
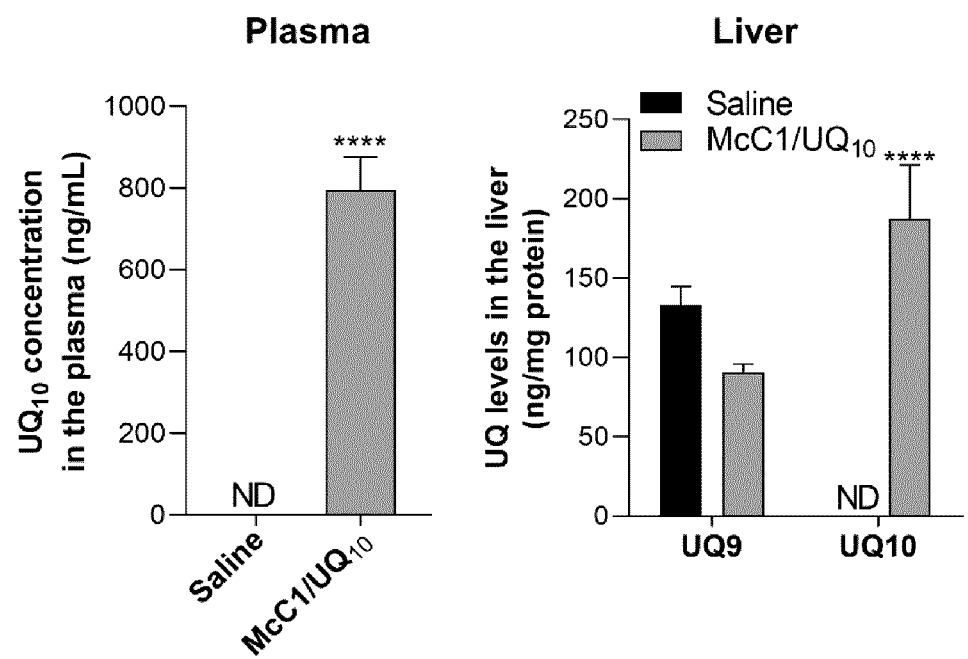
FIG. 27 shows plasma and liver $UQ_{10}$ levels after 5 days i.p. treatment with $UQ_{10}$ solubilized with capsofungin/McC1. 200 µl of McC1/$UQ_{10}$ solution (4 mM of McC1 and 1.4 mM of $UQ_{10}$) was administered intraperitoneally daily for a total of 5 days. Young wild-type female mice were used in the experiment. ND: not detected. $p<0.0001$ (t-test).

Studies were performed to assess the effect of McC1-solubilized $UQ_{10}$ in mice, via by IP (intraperitoneal) and IV (intravenous) administration. As shown in FIG. 27, plasma levels of $UQ_{10}$ increased considerably after 5 days of IP treatment with McC1-solubilized $UQ_{10}$, and this is accompanied by accumulation of a substantial amount of $UQ_{10}$ in the liver.

Figure 28:
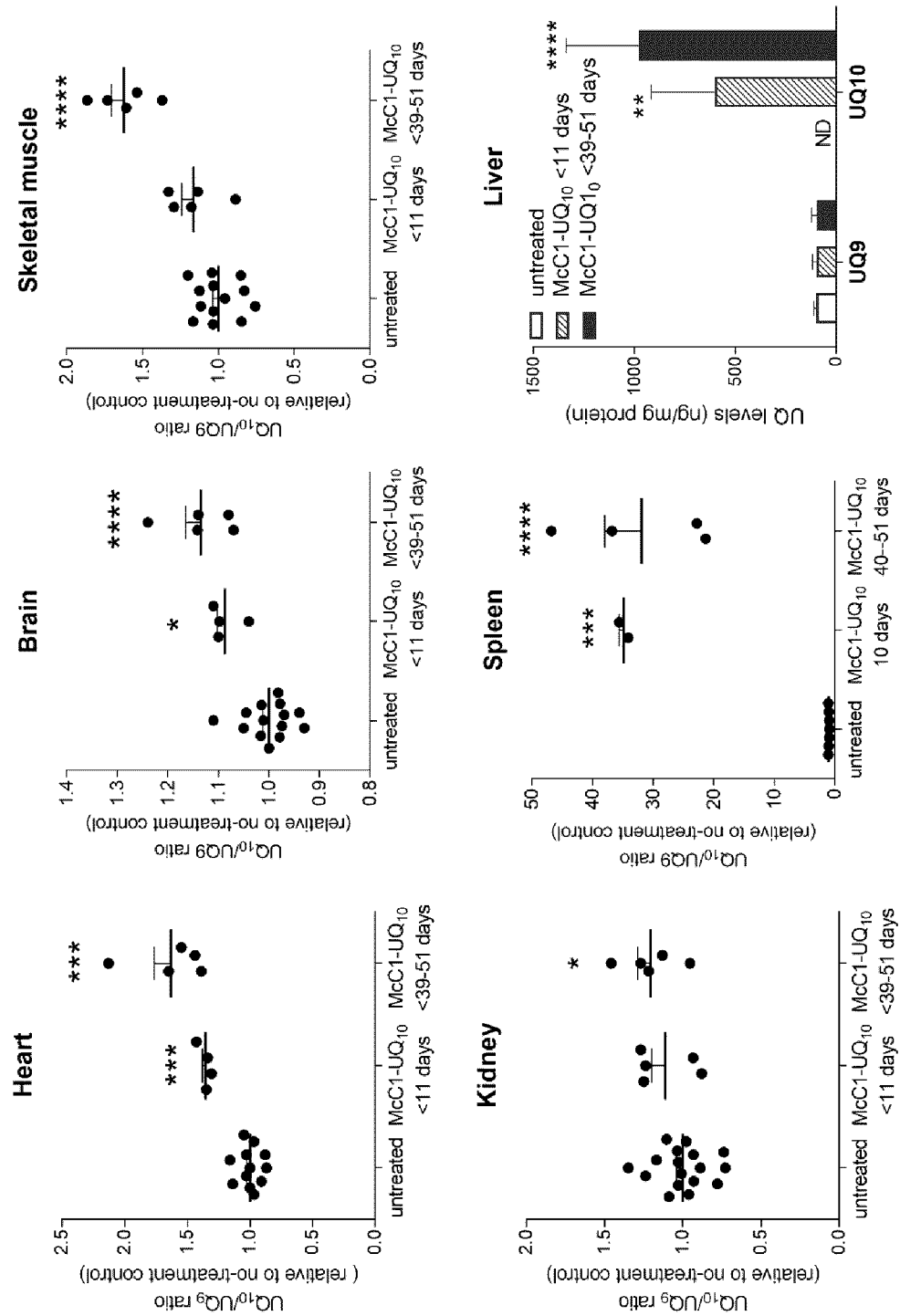
FIG. 28 shows UQ levels and $UQ_9/UQ_{10}$ ratios in mouse tissues after intravenous administration of McC1-solubilized $UQ_{10}$. Injections were carried out daily through a jugular vein catheter. The injection solutions contained 4 mM of McC1 and 1-2 mM of $UQ_{10}$. Young wild-type male mice were used in the experiment. An increase in the concentration ratio of $UQ_{10}/UQ_9$ was observed in the tissues examined, including kidney, heart, skeletal muscle, brain and spleen, indicating a significant uptake of exogenous $UQ_{10}$. For the liver, under no treatment condition, $UQ_{10}$ concentration is low and below the limit of detection, therefore the $UQ_{10}/UQ_9$ ratio cannot obtained. After treatment with McC1/$UQ_{10}$ micelles, a significant concentration of $UQ_{10}$, shown as ng/mg total protein, was detected in the liver. Error bars represent mean±SEM. $p^*<0.05$; $p^{}<0.01$; $p^{*}<0.001$; $p^{****}<0.0001$ compared to no-treatment control (one-way ANOVA followed by Dunnett's multiple comparisons test). ND: not detected.

Further in vivo studies were carried out via jugular vein catheter administration of McC1-solubilized $UQ_{10}$ to mice. Jugular vein-catheterized mice were purchased from Charles River. Mixture of McC1 and $UQ_{10}$ was filter sterilized using a 0.22 μm syringe filter before injection via catheter into the jugular vein. Mice were injected every day with 0.1 ml of McC1/$UQ_{10}$ solution containing 4 mM of McC1 and 1-3 mM of $UQ_{10}$ until catheters ceased to function or caused severe complications. Table 4 shows that IV administration of McC1/$UQ_{10}$ resulted in dramatic elevation of plasma $UQ_{10}$ levels (there is normally no detectable $UQ_{10}$ in mouse plasma). In addition, for the effect on tissue UQ levels, in the IV-injected mice, we observed a significant increase of $UQ_{10}$/$UQ_9$ ratio in the tissues examined, including kidney, heart, skeletal muscle, brain and spleen, implying elevated $UQ_{10}$ levels and therefore uptake of exogenous $UQ_{10}$ (FIG. 28). For the liver, under no treatment condition, $UQ_{10}$ concentration is low and below the limit of detection, therefore the $UQ_{10}$/$UQ_9$ ratio cannot obtained. After treatment with McC1/$UQ_{10}$ micelles, a significant concentration of $UQ_{10}$, shown as ng/mg total protein, was detected in the liver. Of further note, no obvious toxicity was observed after 50 days of IV injections, indicating minimal toxicity with McC1/UQ treatment.

Table 4 shows plasma $UQ_{10}$ levels after intravenous injection of McC1-solubilized $UQ_{10}$. Injections were carried out daily through a jugular vein catheter. The injection solution contains 4 mM of McC1 and 1-2 mM of $UQ_{10}$. Young wild-type male mice were used in the experiment.

TABLE 4

Plasma $UQ_{10}$ levels after intravenous injection of McC1-solubilized $UQ_{10}$.

| Sample | $UQ_9$ (ng/mL) | $UC_{10}$ (ng/mL) |
| --- | --- | --- |
| Untreated (n = 3) | 142.7 ± 1.4 | Not detectable |
| McC1/$UQ_{10}$ 39 days | 62.3 | 521.4 |
| McC1/$UQ_{10}$ 51 days | 203.4 | 2863.4 |
| McC1/$UQ_{10}$ 51 days | 322.9 | 29665.5 |

Figure 29:
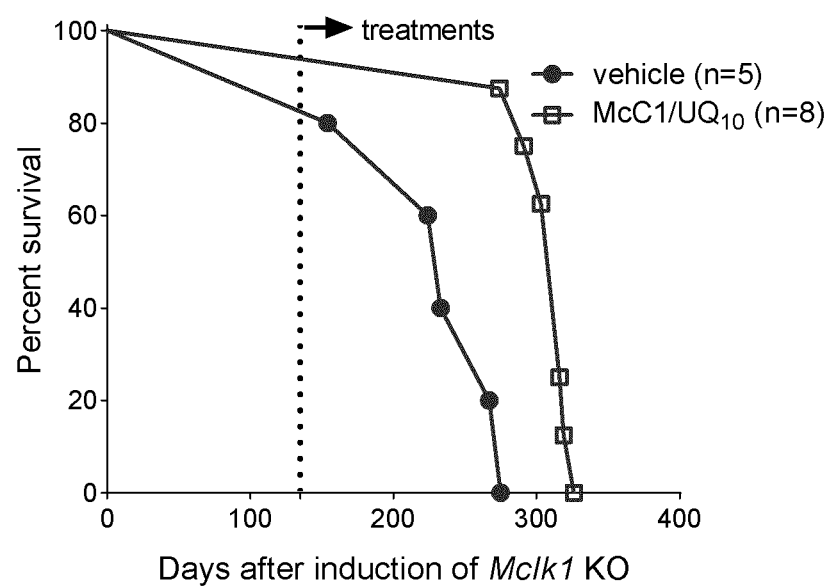
FIG. 29 shows the effect of treatment with McC1/$UQ_{10}$ micelles on the lifespan of whole-body Mclk1 knockout (KO) mice. Mclk1 KO mice received intraperitoneal (i.p.) injections of aqueous solution of McC1-solubilized $UQ_{10}$ one time every day, starting at ~4 months after the gene knockout. At this time the mice showed already a variety of severe phenotypes. The dose for the McC1/$UQ_{10}$ treatment was ~3.2 mg/kg of body weight/day. Control group received i.p. saline. The treated mice lived longer than the untreated mice ($p<0.001$, log rank test).

Example X—In Vivo Evaluation of Mcc1-Solubilized $UQ_{10}$ in Mclk1 Knockout Mice The inducible Mclk1 knockout mouse was created as described (Wang, Oxer et al. 2015). In brief, the Mclk1 gene was deleted globally at the age of 6-8 weeks by administration of tamoxifen. This resulted in a gradual depletion of UQ content in all tissues except for the liver and in turn led to loss of mitochondrial respiratory function in most tissues and early death. For treatment with McC1/$UQ_{10}$, Mclk1 KO mice received intraperitoneal (i.p.) injections of aqueous solution of McC1-solubilized $UQ_{10}$ one time every day, starting at 4 months after the gene knockout. At this time the mice showed already a variety of severe phenotypes. The dose for the McC1/$UQ_{10}$ treatment was 3.2 mg/kg of body weight/day. Control group received i.p. saline. As shown in FIG. 29, the treated KO mice lived longer than the saline injected KO mice (p<0.001, log rank test).

Example XI—Determination of the Effect of McC1-Solubilized Paclitaxel on Cell Growth and Survival Exponentially growing MEFs (mouse embryonic fibroblasts) were seeded into 48-well plates at a low density of $1 \times 10^4$ cells/well. Pacitaxel/McC1 solution was prepared the same way as McC1/$UQ_{10}$ solution and stored at 4° C. until use. Cells were allowed to attach overnight and then the PTX/McC1 solution was added into the culture media to obtain the desired concentrations. After 2 days' treatment, the standard resazurin reduction assay was used to evaluate cell growth and survival. Results are shown in FIG. 26B.

TABLE 5

Murine and human Mclk1/COQ7 and Pdss2 nucleotide and polypeptide sequences described in the sequence listing.

| Description | Details | SEQ ID NO: |
| --- | --- | --- |
| Murine Mclk1/COQ7 nucleotide seq. (transcript) | Genomic: Accession 12850<br>Transcript: Accession BC038681<br>Coding sequence: 34-687 | 1 |
| Murine Mclk1/COQ7 polypeptide seq. | Accession: NP_034070<br>Transit peptide: 1-23<br>Mature peptide: 24-217 | 2 |

TABLE 5-continued

Murine and human Mclk1/COQ7 and Pdss2 nucleotide and polypeptide sequences described in the sequence listing.

| Description | Details | SEQ ID NO: |
|---|---|---|
| Human COQ7 nucleotide seq. (transcript) | Genomic: Accession 10229 Transcript: Accession NM_016138 Coding sequence: 52-705 | 3 |
| Human COQ7 Polypeptide seq. | Accession: NP_057222 | 4 |
| Murine Pdss2 nucleotide seq. (transcript) | Genomic: Accession 10229 Transcript: Accession NM_001168289 Coding sequence: 277-1335 | 5 |
| Murine Pdss2 Polypeptide seq. | Accession: NP_001161761 | 6 |
| Human Pdss2 nucleotide seq. (transcript) | Genomic: Accession 57107 Transcript: Accession NM_020381 Coding sequence: 291-1490 | 7 |
| Human Pdss2 Polypeptide seq. | Accession: NP_065114 | 8 |

While the invention has been described in connection with specific embodiments thereof, it will be understood that the scope of the claims should not be limited by the preferred embodiments set forth in the examples, but should be given the broadest interpretation consistent with the description as a whole.

REFERENCES

1. Peng, M., et al., *Primary coenzyme Q deficiency Pdss2 mutant mice causes isolated renal disease*. PLoS Genet, 2008. 4(4): p. e1000061.
2. Levavasseur, F., et al., *Ubiquinone is necessary for mouse embryonic development but is not essential for mitochondria respiration*. J Biol Chem, 2001. 276(49): p. 46160-4.
3. Ewban k, J. J., et al., *Structural and functional conservation of the Caenorhabditis elegans timing gene clk-1*. Science, 1997. 275(5302): p. 980-3.
4. Nakai, D., et al., *Mouse homologue of coq7/clk-1, longevity gene in Caenorhabditis elegans, is essential for coenzyme Q synthesis, maintenance of mitochondrial integrity, and neurogenesis*. Biochem Biophys Res Commun, 2001. 289(2): p. 463-71.
5. Wang, Y., D. Oxer, and S. Hekimi, *Mitochondrial function and lifespan of mice with controlled ubiquinone biosynthesis*. Nat Commun, 2015. 6: p. 6393.
6. Bhagavan, H. N. and R. K. Chopra, *Plasma coenzyme Q10 response to oral ingestion of coenzyme Q10 formulations*. Mitochondrion, 2007. 7 Suppl: p. S78-88.
7. Seo, D. W., et al., *Self-microemulsifying formulation-based oral solution of coenzyme Q10*. Yakugaku Zasshi, 2009. 129(12): p. 1559-63.
8. Kommuru, T. R., et al., *Self-emulsifying drug delivery systems (SEDDS) of coenzyme Q10: formulation development and bioavailability assessment*. Int J Pharm, 2001. 212(2): p. 233-46.
9. Schulz, C., et al., *Comparison of the relative bioavailability of different coenzyme Q10 formulations with a novel solubilizate (Solu Q10)*. Int J Food Sci Nutr, 2006. 57(7-8): p. 546-55.
10. Chopra, R. K., et al., *Relative bioavailability of coenzyme Q10 formulations in human subjects*. Int J Vitam Nutr Res, 1998. 68(2): p. 109-13.
11. Liu, Z. X. and C. Artmann, *Relative bioavailability comparison of different coenzyme Q10 formulations with a novel delivery system*. Altern Ther Health Med, 2009. 15(2): p. 42-6.
12. Beg, S., S. Javed, and K. Kohli, *Bioavailability enhancement of coenzyme Q10: an extensive review of patents*. Recent Pat Drug Deliv Formul, 2010. 4(3): p. 245-55.
13. Cho, H., J. Gao, and G. S. Kwon, *PEG-b-PLA micelles and PLGA-b-PEG-b-PLGA sol-gels for drug delivery*. J Control Release, 2016. 240: p. 191-201.
14. Wang, Y. and S. Hekimi, *Molecular genetics of ubiquinone biosynthesis in animals*. Crit Rev Biochem Mol Biol, 2013. 48(1): p. 69-88.
15. Wang, Y. and S. Hekimi, Mitochondrial respiration without ubiquinone biosynthesis. Hum Mol Genet, 2013. 22(23): p. 4768-83).
16. McCarthy, J. J., et al., *Inducible Cre transgenic mouse strain for skeletal muscle-specific gene targeting*. Skelet Muscle, 2012. 2(1): p. 8.
17. Sohal, D. S., et al., *Temporally regulated and tissue-specific gene manipulations in the adult and embryonic heart using a tamoxifen-inducible Cre protein*. Circ Res, 2001. 89(1): p. 20-5.
18. Engblom, D., et al., *Glutamate receptors on dopamine neurons control the persistence of cocaine seeking*. Neuron, 2008. 59(3): p. 497-508.

What is claimed is:

1. A composition comprising a mixture of caspofungin or a pharmaceutically or biologically acceptable salt thereof and a ubiquinone in an aqueous solution.

2. The composition of claim 1 comprising a suspension of micelles composed of caspofungin or the pharmaceutically or biologically acceptable salt thereof and ubiquinone.

3. A method of delivering ubiquinone to a cell, the method comprising contacting the composition of claim 1 with the cell.

4. A method of preparing the composition of claim 1, comprising solubilizing ubiquinone with caspofungin or the pharmaceutically or biologically acceptable salt thereof, to provide the composition.

5. The method of claim 4, comprising forming a suspension of micelles composed of caspofungin or the pharmaceutically or biologically acceptable salt thereof, and ubiquinone.

6. A method of treating or alleviating the symptoms of a disease or a condition selected from mitochondrial disease, Parkinson's disease, Huntington's disease, Alzheimer's disease, amyotrophic lateral sclerosis, type I diabetes, type II diabetes, cardiac failure, ischemic heart disease, hypertension, coronary artery disease, idiopathic dilated cardiomyopathy, pulmonary arterial hypertension, ataxia, bipolar depression, Duchenne muscular dystrophy, fibromyalgia, asthenozoospermia, periodontal disease, migraine, pre-eclampsia, Down's syndrome, leukemia, breast cancer, cervical cancer and prostate cancer in a subject in need thereof that would benefit from an increase in intracellular ubiquinone levels, the method comprising administering a therapeutically effective amount of the composition of claim 1 to the subject, so as to treat or alleviate the symptoms of the disease or the condition in the subject.

7. The composition of claim 1, wherein the pharmaceutically or biologically acceptable salt of caspofungin is caspofungin acetate.

8. The method of claim 6, wherein the disease or condition is associated with a ubiquinone deficiency.

* * * * *

SEQUENCE LISTING

```
<160> NUMBER OF SEQ ID NOS: 8

<210> SEQ ID NO 1
<211> LENGTH: 882
<212> TYPE: DNA
<213> ORGANISM: Mus musculus
<220> FEATURE:
<221> NAME/KEY: CDS
<222> LOCATION: (34)..(687)

<400> SEQUENCE: 1
ggcgtttgga ccatagctgc attgtccgca gcg atg agc gcc gcc gga gcc ata      54
                                    Met Ser Ala Ala Gly Ala Ile
                                     1               5 gcg gct gct tcc gtg gga cgc ctg cgc act ggt gtc cgg agg ccc ttc     102
Ala Ala Ala Ser Val Gly Arg Leu Arg Thr Gly Val Arg Arg Pro Phe
         10                  15                  20
```

```
tca gag tat gga aga ggc ctc atc atc agg tgt cac agt tcg ggg atg      150
Ser Glu Tyr Gly Arg Gly Leu Ile Ile Arg Cys His Ser Ser Gly Met
     25                  30                  35 acc tta gac aat att aac cgg gca gcc gtg gat cga ata att cgg gtg      198
Thr Leu Asp Asn Ile Asn Arg Ala Ala Val Asp Arg Ile Ile Arg Val
 40                  45                  50                  55 gat cac gct ggt gaa tat gga gca aac cgc atc tat gca ggg caa atg      246
Asp His Ala Gly Glu Tyr Gly Ala Asn Arg Ile Tyr Ala Gly Gln Met
                 60                  65                  70 gcc gtg ctc ggt cgg acc agt gtt ggc cct gtc att cag aaa atg tgg      294
Ala Val Leu Gly Arg Thr Ser Val Gly Pro Val Ile Gln Lys Met Trp
             75                  80                  85 gat caa gag aag aac cat ttg aaa aag ttc aac gag ttg atg att gca      342
Asp Gln Glu Lys Asn His Leu Lys Lys Phe Asn Glu Leu Met Ile Ala
         90                  95                 100 ttc agg gtc cga cct acg gtt ttg atg ccc ttg tgg aac gtg gca ggc      390
Phe Arg Val Arg Pro Thr Val Leu Met Pro Leu Trp Asn Val Ala Gly
    105                 110                 115 ttt gcc ctg ggg gca gga act gcc ttg ctg ggg aag gaa gga gca atg      438
Phe Ala Leu Gly Ala Gly Thr Ala Leu Leu Gly Lys Glu Gly Ala Met
120                 125                 130                 135 gcc tgc acc gtg gcg gta gaa gag tct atc gct aat cac tac aac aac      486
Ala Cys Thr Val Ala Val Glu Glu Ser Ile Ala Asn His Tyr Asn Asn
                140                 145                 150 cag atc cgc atg ctg atg gaa gag gac cct gag aag tat gag gag ctg      534
Gln Ile Arg Met Leu Met Glu Glu Asp Pro Glu Lys Tyr Glu Glu Leu
            155                 160                 165 ctg cag gtc atc aag cag ttt cgc gat gag gag ctt gaa cac cac gat      582
Leu Gln Val Ile Lys Gln Phe Arg Asp Glu Glu Leu Glu His His Asp
        170                 175                 180 aca ggc ctg gac cat gac gca gag ctg gct ccc gcg tat gcc ttg ttg      630
Thr Gly Leu Asp His Asp Ala Glu Leu Ala Pro Ala Tyr Ala Leu Leu
    185                 190                 195 aag agg att atc cag gcc gga tgc agt gca gcc ata tat tta tca gaa      678
Lys Arg Ile Ile Gln Ala Gly Cys Ser Ala Ala Ile Tyr Leu Ser Glu
200                 205                 210                 215 agg ttt tag agtatgtcta ttgatccatt tctagaaaag atggtcgtaa              727
Arg Phe cttaaggagt gatatttgtg gaggaggagc tgtacagtta tcactgtgtg tgttttgtta   787
atacaagagg ccgggtttgg ggcttgtgtt tgtcaataaa ctctttggcg ctggaaaaaa   847
aaaaaaaaaa aaaaaaaaaa aaaaagatga gatgg                              882

<210> SEQ ID NO 2
<211> LENGTH: 217
<212> TYPE: PRT
<213> ORGANISM: Mus musculus

<400> SEQUENCE: 2

Met Ser Ala Ala Gly Ala Ile Ala Ala Ala Ser Val Gly Arg Leu Arg
  1               5                  10                  15

Thr Gly Val Arg Arg Pro Phe Ser Glu Tyr Gly Arg Gly Leu Ile Ile
             20                  25                  30

Arg Cys His Ser Ser Gly Met Thr Leu Asp Asn Ile Asn Arg Ala Ala
         35                  40                  45

Val Asp Arg Ile Ile Arg Val Asp His Ala Gly Glu Tyr Gly Ala Asn
     50                  55                  60

Arg Ile Tyr Ala Gly Gln Met Ala Val Leu Gly Arg Thr Ser Val Gly
 65                  70                  75                  80
```

```
Pro Val Ile Gln Lys Met Trp Asp Gln Glu Lys Asn His Leu Lys Lys
            85                  90                  95

Phe Asn Glu Leu Met Ile Ala Phe Arg Val Arg Pro Thr Val Leu Met
            100                 105                 110

Pro Leu Trp Asn Val Ala Gly Phe Ala Leu Gly Ala Gly Thr Ala Leu
            115                 120                 125

Leu Gly Lys Glu Gly Ala Met Ala Cys Thr Val Ala Val Glu Glu Ser
    130                 135                 140

Ile Ala Asn His Tyr Asn Asn Gln Ile Arg Met Leu Met Glu Glu Asp
145                 150                 155                 160

Pro Glu Lys Tyr Glu Glu Leu Leu Gln Val Ile Lys Gln Phe Arg Asp
                165                 170                 175

Glu Glu Leu Glu His His Asp Thr Gly Leu Asp His Asp Ala Glu Leu
                180                 185                 190

Ala Pro Ala Tyr Ala Leu Leu Lys Arg Ile Ile Gln Ala Gly Cys Ser
            195                 200                 205

Ala Ala Ile Tyr Leu Ser Glu Arg Phe
        210                 215

<210> SEQ ID NO 3
<211> LENGTH: 2642
<212> TYPE: DNA
<213> ORGANISM: Homo sapiens
<220> FEATURE:
<221> NAME/KEY: CDS
<222> LOCATION: (52)..(705)

<400> SEQUENCE: 3
actattggcc agttccgttc aacgaagtgg ttgcttttttt tagttccggc a atg agt    57
                                                          Met Ser
                                                          1 tgc gcc ggg gcg gcg gcg gct ccc cgc ctt tgg cgg ctg cgc ccg ggg    105
Cys Ala Gly Ala Ala Ala Ala Pro Arg Leu Trp Arg Leu Arg Pro Gly
    5                   10                  15 gcc cgg cgg tcc ctc tca gct tat gga aga aga acc agt gtc aga ttt    153
Ala Arg Arg Ser Leu Ser Ala Tyr Gly Arg Arg Thr Ser Val Arg Phe
20                  25                  30 cgc agt tca gga atg act tta gac aat atc agt cgg gca gct gtg gat    201
Arg Ser Ser Gly Met Thr Leu Asp Asn Ile Ser Arg Ala Ala Val Asp
35                  40                  45                  50 cga ata atc cgg gtg gat cat gca ggc gaa tat gga gca aac cgc atc    249
Arg Ile Ile Arg Val Asp His Ala Gly Glu Tyr Gly Ala Asn Arg Ile
                55                  60                  65 tat gcc ggg cag atg gct gtc ctg ggt cgg acc agc gtc ggg cca gtc    297
Tyr Ala Gly Gln Met Ala Val Leu Gly Arg Thr Ser Val Gly Pro Val
            70                  75                  80 att cag aaa atg tgg gat caa gaa aag gac cat ttg aaa aag ttc aat    345
Ile Gln Lys Met Trp Asp Gln Glu Lys Asp His Leu Lys Lys Phe Asn
        85                  90                  95 gag ttg atg gtt acg ttc agg gtc cgg cca aca gtt ctg atg ccc ttg    393
Glu Leu Met Val Thr Phe Arg Val Arg Pro Thr Val Leu Met Pro Leu
    100                 105                 110 tgg aac gtg ctg ggg ttt gca ctg ggg gcg ggg acc gcc ttg ctc ggg    441
Trp Asn Val Leu Gly Phe Ala Leu Gly Ala Gly Thr Ala Leu Leu Gly
115                 120                 125                 130 aag gaa ggt gcc atg gcc tgc acc gtg gcg gtg gaa gag agc ata gca    489
Lys Glu Gly Ala Met Ala Cys Thr Val Ala Val Glu Glu Ser Ile Ala
                135                 140                 145
```

```
cat cac tac aac aac cag atc agg acg ctg atg gag gag gac cct gaa      537
His His Tyr Asn Asn Gln Ile Arg Thr Leu Met Glu Glu Asp Pro Glu
            150                 155                 160 aaa tac gag gaa ctt ctt cag ctg ata aag aaa ttt cgg gat gaa gag      585
Lys Tyr Glu Glu Leu Leu Gln Leu Ile Lys Lys Phe Arg Asp Glu Glu
        165                 170                 175 ctt gag cac cat gac ata ggc ctc gac cat gat gca gaa ttg gct cca      633
Leu Glu His His Asp Ile Gly Leu Asp His Asp Ala Glu Leu Ala Pro
    180                 185                 190 gcc tat gcc gtc ctg aag agc att atc cag gcc gga tgc aga gtg gcg      681
Ala Tyr Ala Val Leu Lys Ser Ile Ile Gln Ala Gly Cys Arg Val Ala
195                 200                 205                 210 ata tat tta tca gaa aga tta taa agtgtgtcca gttttgcctg tctataaaag     735
Ile Tyr Leu Ser Glu Arg Leu
            215 atgatagtaa tttaccaagt gacatttgca gagaaacagg tgtacagtta tcgttgtact    795 tttgtacaat gtgaattttg ttaataaatt ataaggtttg ttttttttt tttaaactct     855 gcagtgttga ttttctctg ggttgttttt tctgccatga accaacagg tcaccagcct      915 tgttcaagtt acagcaaacg aagctgggcc ttgtttggtc tcatacttaa ttttctttta    975 tatacatgtt tttcttttac atgcatatat atatatttta ttttattta tgttttttgg     1035 agacagggcc tcgctctttt gtccaggccg ggtcacaact cactgcagcc tggacctcct    1095 agcctcaagc aatccaccca cctcagcctt ccaagtagct gggactacag gtgtgcacca    1155 ccacagctgg ctaattctat tttttttatag aggcgaagtc tcactatgtc gccaggctgg   1215 tctctaactc ctgggctcag tgatcctccc gtttcgactt cccaaagtgc tgggattaca    1275 ggtgtgagcc acttcaccag gcccattttc tcctaaaact tcaaggacaa atcattaata    1335 atgtaacagg aatctttagg agaaaaaaca atttggttta ctgataacaa agataattg     1395 gaaacatgag agtatttgag attggccaag cagaactatg aagtccatca agtaagtcaa    1455 agatcatcgt ttctgttttg aattgtgggt gataatgggt gggagagtgc tacagtctgt    1515 atgtctgtgt ctccctagaa ttcatacgat gaaatcttca ctctcaagtt gatagaaggt    1575 ggggcccttg ggaagtgtga ggtcatgaga gtggagccct catgaatggg atcagtgcct    1635 tatgaaaggc cctagagaga tacctcatcc tctccacagt gtgagacttc aaggggaagt    1695 atgagacttc tctgaggaag cagacccttc acaagcaaaa tcagccagca ctttgatcac    1755 ggacttccca gcctctagga ctgtgagcaa taaatgtttg atgtttataa gccacccaga    1815 ctgtggtatt tgttatagc agcctgaaca gactaagacg ggggtgttgc ttccatcaaa     1875 ggatgtacta agttgtggat tatttgtgaa attgaattac aaccttttcc ttaaggtctt    1935 ttaccacctc cccccaaaa aaatccccca aaactgattc agattttcat actttaatga    1995 aatatttat aatttgcaaa ttttaagta atttatgaaa aacctagatc agtggatctc      2055 ctctctggct gcccattaga atgtcctgtg gagattaaac ttttttttt cagtttatgg     2115 accaagagtt ttgatttatt tagggtggag ttcaggatca gaatggtttc agaagctccc    2175 aggtgattcc ggagtgagtt ggagctgcaa gcccctgagc tagattataa gatgcttctg    2235 ggaaagaacc acatttagg aatttgcttc ccacccagtg ccctgcattt aatcagcacc     2295 tgatgacttg gcaggacttg ccccaccagg gtctggcttt gaagggtagt ggacaccagg    2355 atcctttgga ttaatcctct gccacctctc tcttttcctc aaccgagagt gaatttatgt    2415 aattgagtga agtctacga atcataattg taataaaatta aggctgggca tttgtttgaa    2475 attagatagg ataaagccaa aggtttgaac aagttgtgga tggtttgtaa aaattaatct    2535
```

```
tacaaaataa atgctgtgtg tgaacacgtt gattaaattc aaaagggtat tatttggttt      2595
ttctgtaaat tgaaccttga aataaaagca caacaaggtt ttcttaa                    2642
```

<210> SEQ ID NO 4
<211> LENGTH: 217
<212> TYPE: PRT
<213> ORGANISM: Homo sapiens

<400> SEQUENCE: 4

```
Met Ser Cys Ala Gly Ala Ala Ala Pro Arg Leu Trp Arg Leu Arg
1               5                   10                  15

Pro Gly Ala Arg Arg Ser Leu Ser Ala Tyr Gly Arg Arg Thr Ser Val
            20                  25                  30

Arg Phe Arg Ser Ser Gly Met Thr Leu Asp Asn Ile Ser Arg Ala Ala
        35                  40                  45

Val Asp Arg Ile Ile Arg Val Asp His Ala Gly Glu Tyr Gly Ala Asn
    50                  55                  60

Arg Ile Tyr Ala Gly Gln Met Ala Val Leu Gly Arg Thr Ser Val Gly
65                  70                  75                  80

Pro Val Ile Gln Lys Met Trp Asp Gln Glu Lys Asp His Leu Lys Lys
                85                  90                  95

Phe Asn Glu Leu Met Val Thr Phe Arg Val Arg Pro Thr Val Leu Met
            100                 105                 110

Pro Leu Trp Asn Val Leu Gly Phe Ala Leu Gly Ala Gly Thr Ala Leu
        115                 120                 125

Leu Gly Lys Glu Gly Ala Met Ala Cys Thr Val Ala Val Glu Glu Ser
    130                 135                 140

Ile Ala His His Tyr Asn Asn Gln Ile Arg Thr Leu Met Glu Glu Asp
145                 150                 155                 160

Pro Glu Lys Tyr Glu Glu Leu Leu Gln Leu Ile Lys Lys Phe Arg Asp
                165                 170                 175

Glu Glu Leu Glu His His Asp Ile Gly Leu Asp His Asp Ala Glu Leu
            180                 185                 190

Ala Pro Ala Tyr Ala Val Leu Lys Ser Ile Ile Gln Ala Gly Cys Arg
        195                 200                 205

Val Ala Ile Tyr Leu Ser Glu Arg Leu
    210                 215
```

<210> SEQ ID NO 5
<211> LENGTH: 1581
<212> TYPE: DNA
<213> ORGANISM: Mus musculus
<220> FEATURE:
<221> NAME/KEY: CDS
<222> LOCATION: (277)..(1335)

<400> SEQUENCE: 5

```
atgcctccaa catggcgccc cccatgtagg cactggctgt ggttaccagc gcaggtatcc      60
agtgcagttc tgagcagccg ctggggttac gccagtctgc gctgcagaag cagcaaacgt     120
tattcctggt tacggctcca gaaagccata cttctctgag ggtttggaat cgccgtctcc     180
tgttagattc tgaaagtttc tcctcagccc ttgtttgctt cccgtgtcat ttctggccac     240
cttcctcagg tccccgaccc tctcagactc aaaact atg agc ctc cgg cag ctg       294
                                        Met Ser Leu Arg Gln Leu
                                        1               5 ctg ttg cgc ttg tcc ggt tac ctc ggg gct tca ggt ccc ccc agt cgc       342
```

| | | | |
|---|---|---|---|
| | Leu Leu Arg Leu Ser Gly Tyr Leu Ala Ser Gly Pro Ser Arg<br>10                15                20 | | |
| cac tgg tgg tac ttc aga tcc ctc gac agc atc tcc tcg gcg ggc tcc<br>His Trp Trp Tyr Phe Arg Ser Leu Asp Ser Ile Ser Ser Ala Gly Ser<br>      25                30                35 | | | 390 |
| tgg cgc ggg cgc tcc tcc agg tca ccg gcc cat tgg aac cag gtg gtg<br>Trp Arg Gly Arg Ser Ser Arg Ser Pro Ala His Trp Asn Gln Val Val<br>   40                45                50 | | | 438 |
| tcc gag gcg gag aag atc gtg ggc tac ccc gca tcc ttc atg agc ctg<br>Ser Glu Ala Glu Lys Ile Val Gly Tyr Pro Ala Ser Phe Met Ser Leu<br>55                60                65                70 | | | 486 |
| cgc tgc ctg ctg agc gac gag ctc agc aat atc gcc atg cag gtg cgg<br>Arg Cys Leu Leu Ser Asp Glu Leu Ser Asn Ile Ala Met Gln Val Arg<br>         75                80                85 | | | 534 |
| aag ctg gtg ggg acg gga cac cct ctg ctt acc act gcc agg gcc ctc<br>Lys Leu Val Gly Thr Gly His Pro Leu Leu Thr Thr Ala Arg Ala Leu<br>         90                95                100 | | | 582 |
| gtg cac gac agc cgg cat aac cta caa ctg cgg ggc ctg gtc gtg ctc<br>Val His Asp Ser Arg His Asn Leu Gln Leu Arg Gly Leu Val Val Leu<br>         105               110               115 | | | 630 |
| ctc ata tca aag gct gcg ggg ccc agc act cgg aac gct gcg tgt cag<br>Leu Ile Ser Lys Ala Ala Gly Pro Ser Thr Arg Asn Ala Ala Cys Gln<br>      120               125               130 | | | 678 |
| aac tac gac atg gtc agt ggg gta tac tca tgt caa aga agt ttg gca<br>Asn Tyr Asp Met Val Ser Gly Val Tyr Ser Cys Gln Arg Ser Leu Ala<br>135               140               145               150 | | | 726 |
| gag atc aca gaa ctt atc cat act gct ctc ctg gtg cat cgt ggg ata<br>Glu Ile Thr Glu Leu Ile His Thr Ala Leu Leu Val His Arg Gly Ile<br>         155               160               165 | | | 774 |
| gta aac tta agt gaa tta cag tca tct gat gga cca ctg aaa gac atg<br>Val Asn Leu Ser Glu Leu Gln Ser Ser Asp Gly Pro Leu Lys Asp Met<br>         170               175               180 | | | 822 |
| cag ttt gga aac aaa ata gct atc ctg agt gga gac ttc ctt cta gca<br>Gln Phe Gly Asn Lys Ile Ala Ile Leu Ser Gly Asp Phe Leu Leu Ala<br>      185               190               195 | | | 870 |
| aat gca tgc aat gga cta gct ctt cta cag aac acc aag gtt gtg gag<br>Asn Ala Cys Asn Gly Leu Ala Leu Leu Gln Asn Thr Lys Val Val Glu<br>      200               205               210 | | | 918 |
| ctt tta tca agt gct ctt atg gac ttg gtg cat gga gta tac cag gag<br>Leu Leu Ser Ser Ala Leu Met Asp Leu Val His Gly Val Tyr Gln Glu<br>215               220               225               230 | | | 966 |
| aac tct gct tcc acc aag gaa aat tct atc cca gat gat att gga atc<br>Asn Ser Ala Ser Thr Lys Glu Asn Ser Ile Pro Asp Asp Ile Gly Ile<br>         235               240               245 | | | 1014 |
| tcg acc tgg aag gag cag act ttc ctg tcc cat tgt gcc ttg cta gcg<br>Ser Thr Trp Lys Glu Gln Thr Phe Leu Ser His Cys Ala Leu Leu Ala<br>         250               255               260 | | | 1062 |
| aag agc tgc cag gct gca atg gag tta gca aag cat gat gct gcg gtc<br>Lys Ser Cys Gln Ala Ala Met Glu Leu Ala Lys His Asp Ala Ala Val<br>         265               270               275 | | | 1110 |
| caa gac atg gca ttc cag tat ggg aag cac atg gcc atg agt cac aag<br>Gln Asp Met Ala Phe Gln Tyr Gly Lys His Met Ala Met Ser His Lys<br>      280               285               290 | | | 1158 |
| atc aat gct gac ctc cag cct ttt att aaa gac aag gcc agt gac tct<br>Ile Asn Ala Asp Leu Gln Pro Phe Ile Lys Asp Lys Ala Ser Asp Ser<br>295               300               305               310 | | | 1206 |
| aag act ttt aac cta aac tca gca cct gta gtc tta cat cag gag ttt<br>Lys Thr Phe Asn Leu Asn Ser Ala Pro Val Val Leu His Gln Glu Phe<br>         315               320               325 | | | 1254 |

```
ctt gga aga gat ttg tgg att aag cag att gga gag gct caa gag aaa    1302
Leu Gly Arg Asp Leu Trp Ile Lys Gln Ile Gly Glu Ala Gln Glu Lys
            330                 335                 340 gga agc ttg aac tac agt aag gtc gtc tcc tga agtccacgct cttcttaaac    1355
Gly Ser Leu Asn Tyr Ser Lys Val Val Ser
        345                 350 ttgctatgga gaatgacctt gaactgcagg tcctcctgcc ttaagaggtg tgcataaccc    1415
tactgtgtta aaaactcatc acaccagcca ggcagtggtg gggcatggct ttaaacccag    1475
tactcggagg cagaggcaag tcgacgtctt gtgaatttga ggccaacctt atcaacaaag    1535
tgagtccagg acagcccagg ctggttactc tgagaaaccc tgtctc                   1581

<210> SEQ ID NO 6
<211> LENGTH: 352
<212> TYPE: PRT
<213> ORGANISM: Mus musculus

<400> SEQUENCE: 6
```

Met Ser Leu Arg Gln Leu Leu Arg Leu Ser Gly Tyr Leu Gly Ala
1               5                   10                  15

Ser Gly Pro Pro Ser Arg His Trp Trp Tyr Phe Arg Ser Leu Asp Ser
                20                  25                  30

Ile Ser Ser Ala Gly Ser Trp Arg Gly Arg Ser Ser Arg Ser Pro Ala
            35                  40                  45

His Trp Asn Gln Val Val Ser Glu Ala Glu Lys Ile Val Gly Tyr Pro
    50                  55                  60

Ala Ser Phe Met Ser Leu Arg Cys Leu Leu Ser Asp Glu Leu Ser Asn
65                  70                  75                  80

Ile Ala Met Gln Val Arg Lys Leu Val Gly Thr Gly His Pro Leu Leu
                85                  90                  95

Thr Thr Ala Arg Ala Leu Val His Asp Ser Arg His Asn Leu Gln Leu
                100                 105                 110

Arg Gly Leu Val Val Leu Leu Ile Ser Lys Ala Ala Gly Pro Ser Thr
            115                 120                 125

Arg Asn Ala Ala Cys Gln Asn Tyr Asp Met Val Ser Gly Val Tyr Ser
    130                 135                 140

Cys Gln Arg Ser Leu Ala Glu Ile Thr Glu Leu Ile His Thr Ala Leu
145                 150                 155                 160

Leu Val His Arg Gly Ile Val Asn Leu Ser Glu Leu Gln Ser Ser Asp
                165                 170                 175

Gly Pro Leu Lys Asp Met Gln Phe Gly Asn Lys Ile Ala Ile Leu Ser
            180                 185                 190

Gly Asp Phe Leu Leu Ala Asn Ala Cys Asn Gly Leu Ala Leu Leu Gln
    195                 200                 205

Asn Thr Lys Val Val Glu Leu Leu Ser Ser Ala Leu Met Asp Leu Val
210                 215                 220

His Gly Val Tyr Gln Glu Asn Ser Ala Ser Thr Lys Glu Asn Ser Ile
225                 230                 235                 240

Pro Asp Asp Ile Gly Ile Ser Thr Trp Lys Glu Gln Thr Phe Leu Ser
                245                 250                 255

His Cys Ala Leu Leu Ala Lys Ser Cys Gln Ala Ala Met Glu Leu Ala
            260                 265                 270

Lys His Asp Ala Ala Val Gln Asp Met Ala Phe Gln Tyr Gly Lys His
    275                 280                 285

Met Ala Met Ser His Lys Ile Asn Ala Asp Leu Gln Pro Phe Ile Lys

```
                    290                 295                 300
Asp Lys Ala Ser Asp Ser Lys Thr Phe Asn Leu Asn Ser Ala Pro Val
305                 310                 315                 320

Val Leu His Gln Glu Phe Leu Gly Arg Asp Leu Trp Ile Lys Gln Ile
                325                 330                 335

Gly Glu Ala Gln Glu Lys Gly Ser Leu Asn Tyr Ser Lys Val Val Ser
            340                 345                 350

<210> SEQ ID NO 7
<211> LENGTH: 3568
<212> TYPE: DNA
<213> ORGANISM: Homo sapiens
<220> FEATURE:
<221> NAME/KEY: CDS
<222> LOCATION: (291)..(1490)

<400> SEQUENCE: 7
ggccgcattc catgcctcca atatggcgtc ctccacatag gcagtggctg tggtttctac      60
cccgggtggc cggggggcagt gctgagctgg gactgttgtt tgcccagcct gggctgcaga    120
aagcagcagt taaagttcgt ttctggtcac tgctccagga agccaccttta ctctgagggt    180 caagaattgc cgcttccttt tagttactgt aagttcctcc tctgccctg gtttgtttcc      240 cgcggcactt ctggataccc ccaggtccca gaccttcca gactcaaacc atg aac          296
                                                       Met Asn
                                                        1 ttt cgg cag ctg ctg ttg cac ttg cca cgt tat ctt gga gcc tcg ggt        344
Phe Arg Gln Leu Leu Leu His Leu Pro Arg Tyr Leu Gly Ala Ser Gly
         5                  10                  15 tcc ccg cgt cgc ctg tgg tgg tcc ccg tcc ctc gac acc atc tcc tcg        392
Ser Pro Arg Arg Leu Trp Trp Ser Pro Ser Leu Asp Thr Ile Ser Ser
     20                  25                  30 gtg ggc tct tgg cgt ggt cgg tcc tcc aag tcc ccg gcc cac tgg aat        440
Val Gly Ser Trp Arg Gly Arg Ser Ser Lys Ser Pro Ala His Trp Asn
35                  40                  45                  50 cag gta gtg tca gag gcg gag aag atc gtg ggg tac ccc acg tcc ttc        488
Gln Val Val Ser Glu Ala Glu Lys Ile Val Gly Tyr Pro Thr Ser Phe
                 55                  60                  65 atg agc ctt cgc tgc ctg ctg agc gac gag ctc agc aac atc gct atg        536
Met Ser Leu Arg Cys Leu Leu Ser Asp Glu Leu Ser Asn Ile Ala Met
             70                  75                  80 cag gtg cgg aag ctg gtg ggc act cag cac cct ctg ctt acc aca gcc        584
Gln Val Arg Lys Leu Val Gly Thr Gln His Pro Leu Leu Thr Thr Ala
         85                  90                  95 agg ggg ctt gta cat gac agc tgg aat agc ctc cag ttg agg ggc ttg        632
Arg Gly Leu Val His Asp Ser Trp Asn Ser Leu Gln Leu Arg Gly Leu
     100                 105                 110 gtg gtg ctc ctt atc tct aaa gca gct ggg ccc agc agc gtg aac act        680
Val Val Leu Leu Ile Ser Lys Ala Ala Gly Pro Ser Ser Val Asn Thr
115                 120                 125                 130 tca tgt cag aac tat gac atg gtc agt ggg atc tac tca tgt caa aga        728
Ser Cys Gln Asn Tyr Asp Met Val Ser Gly Ile Tyr Ser Cys Gln Arg
                 135                 140                 145 agt ttg gca gag atc acg gag cta att cat att gct ctc ctt gta cat        776
Ser Leu Ala Glu Ile Thr Glu Leu Ile His Ile Ala Leu Leu Val His
             150                 155                 160 cgt ggg ata gta aat tta aat gag ttg caa tca tct gat ggt cca ctg        824
Arg Gly Ile Val Asn Leu Asn Glu Leu Gln Ser Ser Asp Gly Pro Leu
         165                 170                 175 aaa gac atg caa ttt gga aat aaa att gct atc ctg agt gga gac ttt        872
```

```
Lys Asp Met Gln Phe Gly Asn Lys Ile Ala Ile Leu Ser Gly Asp Phe
    180                 185                 190 ctt cta gca aat gcc tgc aat gga cta gct ctg cta cag aac acc aag    920
Leu Leu Ala Asn Ala Cys Asn Gly Leu Ala Leu Leu Gln Asn Thr Lys
195                 200                 205                 210 gtt gtg gaa ctt tta gca agt gct ctt atg gac ttg gta caa gga gta    968
Val Val Glu Leu Leu Ala Ser Ala Leu Met Asp Leu Val Gln Gly Val
                    215                 220                 225 tat cat gaa aat tct act tca aag gaa agt tat atc aca gat gat att   1016
Tyr His Glu Asn Ser Thr Ser Lys Glu Ser Tyr Ile Thr Asp Asp Ile
                230                 235                 240 gga ata tcg act tgg aag gag cag act ttt ctc tcc cat ggt gcc tta   1064
Gly Ile Ser Thr Trp Lys Glu Gln Thr Phe Leu Ser His Gly Ala Leu
            245                 250                 255 cta gca aag agc tgc caa gct gca atg gaa tta gca aag cat gat gct   1112
Leu Ala Lys Ser Cys Gln Ala Ala Met Glu Leu Ala Lys His Asp Ala
        260                 265                 270 gag gtt cag aat atg gca ttt cag tat ggg aag cac atg gcc atg agt   1160
Glu Val Gln Asn Met Ala Phe Gln Tyr Gly Lys His Met Ala Met Ser
275                 280                 285                 290 cat aag ata aat tct gat gtc cag cct ttt att aaa gaa aag acc agt   1208
His Lys Ile Asn Ser Asp Val Gln Pro Phe Ile Lys Glu Lys Thr Ser
                295                 300                 305 gac tcc atg act ttt aat cta aac tca gct cct gta gtc tta cat cag   1256
Asp Ser Met Thr Phe Asn Leu Asn Ser Ala Pro Val Val Leu His Gln
            310                 315                 320 gaa ttt ctt gga aga gat ttg tgg att aaa cag atc gga gag gct caa   1304
Glu Phe Leu Gly Arg Asp Leu Trp Ile Lys Gln Ile Gly Glu Ala Gln
        325                 330                 335 gaa aaa gga aga ttg gac tat gct aag ttg cga gaa aga atc aaa gct   1352
Glu Lys Gly Arg Leu Asp Tyr Ala Lys Leu Arg Glu Arg Ile Lys Ala
340                 345                 350 ggc aaa ggt gtg act tca gct att gac ctg tgt cgt tac cat gga aac   1400
Gly Lys Gly Val Thr Ser Ala Ile Asp Leu Cys Arg Tyr His Gly Asn
                355                 360                 365                 370 aag gca ctg gag gcc ctg gag agc ttt cct ccc tcg gag gcc aga tct   1448
Lys Ala Leu Glu Ala Leu Glu Ser Phe Pro Pro Ser Glu Ala Arg Ser
            375                 380                 385 gct tta gaa aac att gtg ttt gct gtg acc aga ttt tca tga           1490
Ala Leu Glu Asn Ile Val Phe Ala Val Thr Arg Phe Ser
        390                 395 catcaaatta aaaagacact attgttagtt agctgaaaat cctagggaat gaggttgatt   1550
gggagcgctt tcacgatgcg ttaatgactt ttaaaacata tgcatttttc cttccttta    1610 tcacattgct aaatgagttc tgctttcttt ttggaactgc tacaaacaaa attagaagaa   1670 aaaaggtca agcagttttc acttgtcacg ccagaagcac acttgaggct gcagtcgcag    1730
aaataattaa tgagattcgc tcctgtgacc tcagcaaatg acaggaaat aagtccttat    1790 tgattggacc gagccaggga tggcgccagg gcggtggcct gtggttttc ctgctagaga    1850 ggacaaagca agttggaagc tgcaggtgtc aagagaaatg ctctcaatac caaccaggga   1910
ggattgtcta atcaaaaact agtgaccaat ttgtcataat ggagagtagt tcaatggatt   1970
gagaaaaata tgtttatt gttggcttgt aattatgtct ctggattatt attatttttt    2030
ttttagatgt agttttgctc ttgttgccca ggctggagtg caatggtgca gttttgactc   2090
actgcaacct ccgcctcctg ggttcaagtg attctcctgc ctcagcctcc cgagtagctg   2150
gaattacagg cacctgccac cacgcctggc taattttgta ttttagtag agatggggtt    2210
```

```
tcactatgtt ggtcaggcta gtctcgaact cctgacctca ggtgatccgc ctgcctcggc    2270
ctcccaaagt gctgggatta gaggcttgag ccactgcacc tggcctcatg tctctggatt    2330
tataatgcag tatgaatata ctttgtgctt tatggttttt ataatgtctt tttggagaaa    2390
ttgccgaaaa gttgccaaat acttgaagta ggagattaaa atgttatcaa atgttaaatt    2450
ggttatatta ggaatagtct gttttctttt cctgaagatc agttttttta ttcaaacaca    2510
tttcaaagaa ccaaattttt tttttcttta aggaaaaagg agcttttttt caagtgaaat    2570
gtattcattt gtaatacttt ggtttaaggc atactttaat ttttacgagt ttcagaaaca    2630 gaattttttgt actagggaat tcattggtga gagtgttctt ttaacctcag aatgtcaaat    2690
tttggtcttg aaccacagac atccaattac agaaagaata taagcaatct cacaggcctg    2750
caatcggaca ctgtctctgt gtggttcata ggagatgatt tttgaggttt gcactcatgc    2810
aatttgagaa caccgttgac aagaaggctg agtttacata aatgatctag attgaaactc    2870
agctaccttt cttcctcatg tggtgtaatt acagccctat ctggagacag cgaatacagc    2930
aaacagattt tattacctag ttcgctcaaa cactacatga agttatttta gttaaagccc    2990
tcccccaaaa gttataaaac cattttatca gggcccaaca tgtggcatgc aatgaagaga    3050
aaatgtaaag ctacagaggt taatgtattg tattataaaa tattttaagt gtactcaaaa    3110
tatcataatt gtacagttta tgccaccata atttgaggcc tatagattta gcttaagaga    3170
acactgttct gtttgaaatg ctttctgtca ctgaaattgg cttaattagt aaccatggat    3230
aagatgcttt agatcagact aggttttaat cattaacttc cacaaagaag tcatactttg    3290
cgttaggtgt gctggttgga tgtgcaggaa cttcagcaag cagtaggttt tactaagcag    3350
atggtcgggc actgcagggc accaggcagg atcctagggc gcctcttatt ctgcgttagc    3410
atctggtttg ctgtatgacc ttgcacaagt cacttccttc tgagcctcaa ttttctcatc    3470
tgtacaatga gattcaaaag ttgacctgaa agtcaagtgt gaaaaaaaaa aagagattaa    3530
acaagataat tatgaaattc ttaaaaaaaa aaaaaaaa                            3568
```

<210> SEQ ID NO 8
<211> LENGTH: 399
<212> TYPE: PRT
<213> ORGANISM: Homo sapiens

<400> SEQUENCE: 8

```
Met Asn Phe Arg Gln Leu Leu His Leu Pro Arg Tyr Leu Gly Ala
1               5                   10                  15

Ser Gly Ser Pro Arg Arg Leu Trp Trp Ser Pro Ser Leu Asp Thr Ile
            20                  25                  30

Ser Ser Val Gly Ser Trp Arg Gly Arg Ser Ser Lys Ser Pro Ala His
        35                  40                  45

Trp Asn Gln Val Val Ser Glu Ala Glu Lys Ile Val Gly Tyr Pro Thr
    50                  55                  60

Ser Phe Met Ser Leu Arg Cys Leu Leu Ser Asp Glu Leu Ser Asn Ile
65                  70                  75                  80

Ala Met Gln Val Arg Lys Leu Val Gly Thr Gln His Pro Leu Leu Thr
                85                  90                  95

Thr Ala Arg Gly Leu Val His Asp Ser Trp Asn Ser Leu Gln Leu Arg
            100                 105                 110

Gly Leu Val Val Leu Leu Ile Ser Lys Ala Ala Gly Pro Ser Ser Val
        115                 120                 125

Asn Thr Ser Cys Gln Asn Tyr Asp Met Val Ser Gly Ile Tyr Ser Cys
```

```
            130                 135                 140
Gln Arg Ser Leu Ala Glu Ile Thr Glu Leu Ile His Ile Ala Leu Leu
145                 150                 155                 160

Val His Arg Gly Ile Val Asn Leu Asn Glu Leu Gln Ser Ser Asp Gly
                165                 170                 175

Pro Leu Lys Asp Met Gln Phe Gly Asn Lys Ile Ala Ile Leu Ser Gly
            180                 185                 190

Asp Phe Leu Leu Ala Asn Ala Cys Asn Gly Leu Ala Leu Leu Gln Asn
                195                 200                 205

Thr Lys Val Val Glu Leu Leu Ala Ser Ala Leu Met Asp Leu Val Gln
        210                 215                 220

Gly Val Tyr His Glu Asn Ser Thr Ser Lys Glu Ser Tyr Ile Thr Asp
225                 230                 235                 240

Asp Ile Gly Ile Ser Thr Trp Lys Glu Gln Thr Phe Leu Ser His Gly
                245                 250                 255

Ala Leu Leu Ala Lys Ser Cys Gln Ala Ala Met Glu Leu Ala Lys His
                260                 265                 270

Asp Ala Glu Val Gln Asn Met Ala Phe Gln Tyr Gly Lys His Met Ala
            275                 280                 285

Met Ser His Lys Ile Asn Ser Asp Val Gln Pro Phe Ile Lys Glu Lys
        290                 295                 300

Thr Ser Asp Ser Met Thr Phe Asn Leu Asn Ser Ala Pro Val Val Leu
305                 310                 315                 320

His Gln Glu Phe Leu Gly Arg Asp Leu Trp Ile Lys Gln Ile Gly Glu
                325                 330                 335

Ala Gln Glu Lys Gly Arg Leu Asp Tyr Ala Lys Leu Arg Glu Arg Ile
            340                 345                 350

Lys Ala Gly Lys Gly Val Thr Ser Ala Ile Asp Leu Cys Arg Tyr His
            355                 360                 365

Gly Asn Lys Ala Leu Glu Ala Leu Glu Ser Phe Pro Pro Ser Glu Ala
        370                 375                 380

Arg Ser Ala Leu Glu Asn Ile Val Phe Ala Val Thr Arg Phe Ser
385                 390                 395
```